US011864958B2

(12) United States Patent
Sauer

(10) Patent No.: US 11,864,958 B2
(45) Date of Patent: Jan. 9, 2024

(54) SURGICAL EQUIPMENT HOLDER

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 796 days.

(21) Appl. No.: 16/610,352

(22) PCT Filed: May 17, 2018

(86) PCT No.: PCT/US2018/033288
§ 371 (c)(1),
(2) Date: Nov. 1, 2019

(87) PCT Pub. No.: WO2018/204937
PCT Pub. Date: Nov. 8, 2018

(65) Prior Publication Data
US 2020/0085530 A1    Mar. 19, 2020

Related U.S. Application Data

(63) Continuation-in-part of application No. PCT/US2018/030846, filed on May 3, 2018.
(Continued)

(51) Int. Cl.
*A61B 90/50* (2016.01)
*A61B 90/57* (2016.01)
(Continued)

(52) U.S. Cl.
CPC .......... *A61B 90/50* (2016.02); *A61B 1/00149* (2013.01); *A61B 17/0206* (2013.01);
(Continued)

(58) Field of Classification Search
CPC .............. A61B 90/50; A61B 2090/508; A61B 2090/571; A61B 34/30; A61B 1/00147;
(Continued)

(56) References Cited

U.S. PATENT DOCUMENTS 3,910,538 A    10/1975    Baitella
5,609,565 A    3/1997    Nakamura
(Continued)

FOREIGN PATENT DOCUMENTS

WO    2016160272    10/2016

OTHER PUBLICATIONS

Jul. 6, 2018 International Search Report; Copenheaver, Blaine R., International Search Report for PCT/US2018030846.
(Continued)

*Primary Examiner* — Sarah W Aleman
(74) *Attorney, Agent, or Firm* — Michael E. Coyne

(57) ABSTRACT

A surgical equipment holder is disclosed. The surgical equipment holder includes a first arm pivotable relative to a base, a second arm pivotably coupled to the first arm and an end effector pivotable relative to the second arm. The surgical equipment holder may also include features on the first arm and the second arm configured to allow enhanced cleanability of the surgical instrument holder. The surgical equipment holder also includes a lever configured to actuate between a locked and unlocked position by use of a single hand by an operator. The end effector of the surgical equipment holder is configured to support and finely adjust the position of any number of surgical accessories during surgical procedures.

24 Claims, 76 Drawing Sheets

FIG. 13B

Related U.S. Application Data

(60) Provisional application No. 62/500,972, filed on May 3, 2017, provisional application No. 62/507,724, filed on May 17, 2017, provisional application No. 62/526,329, filed on Jun. 28, 2017.

(51) Int. Cl.
  *A61B 1/00* (2006.01)
  *A61B 17/02* (2006.01)
  *A61B 17/00* (2006.01)

(52) U.S. Cl.
  CPC ..... *A61B 90/57* (2016.02); *A61B 2017/00115* (2013.01); *A61B 2017/00477* (2013.01); *A61B 2090/508* (2016.02); *A61B 2090/571* (2016.02)

(58) Field of Classification Search
  CPC .. A61B 1/00149; A61B 17/02; A61B 17/0206
  See application file for complete search history.

(56) References Cited

U.S. PATENT DOCUMENTS

| | | | |
|---|---|---|---|
| 5,779,209 A * | 7/1998 | Rello | F16M 11/10 248/278.1 |
| 6,471,165 B2 | 10/2002 | Twisselman | |
| 8,132,769 B2 | 3/2012 | Metelski | |
| 8,424,823 B2 | 4/2013 | Fadler et al. | |
| 9,437,469 B2 | 9/2016 | DiBella et al. | |
| D800,814 S | 10/2017 | Matuschek et al. | |
| 10,352,497 B2 | 7/2019 | Yokiel et al. | |
| 10,788,160 B2 | 9/2020 | Elias | |
| 11,103,126 B2 | 8/2021 | Sauer | |
| 2002/0077531 A1 | 6/2002 | Puchovsky et al. | |
| 2007/0213597 A1* | 9/2007 | Wooster | A61B 17/0206 600/234 |
| 2009/0247819 A1* | 10/2009 | Wilson | A61B 90/57 600/102 |
| 2011/0190592 A1 | 8/2011 | Kahle et al. | |
| 2014/0208514 A1* | 7/2014 | Schuerch, Jr. | A61G 13/1245 29/428 |
| 2016/0151120 A1* | 6/2016 | Kostrzewski | A61B 90/50 606/130 |
| 2019/0328475 A1 | 10/2019 | Arai et al. | |
| 2019/0328479 A1 | 10/2019 | Wada et al. | |

OTHER PUBLICATIONS

Aug. 13, 2018 International Search Report; Young, Lee W., International Search Report for PCT/US2018033288.

Extended European Search Report, Application No. 18794221.4, dated Dec. 2, 2020, 9 pages.

Japanese Office Action, for Japanese Application No. 2019-558765, dated May 7, 2021, 12 pages.

Australian Examination Report, Application No. 2018263972, dated Jul. 11, 2020, 5 pages.

* cited by examiner

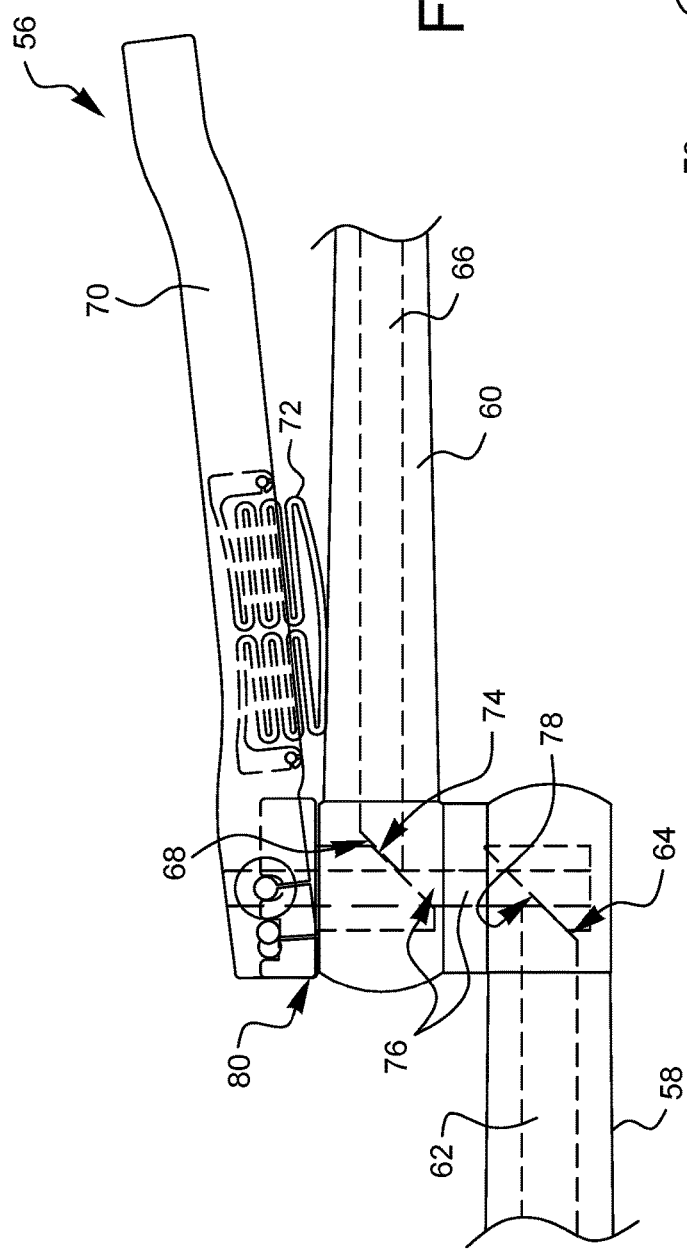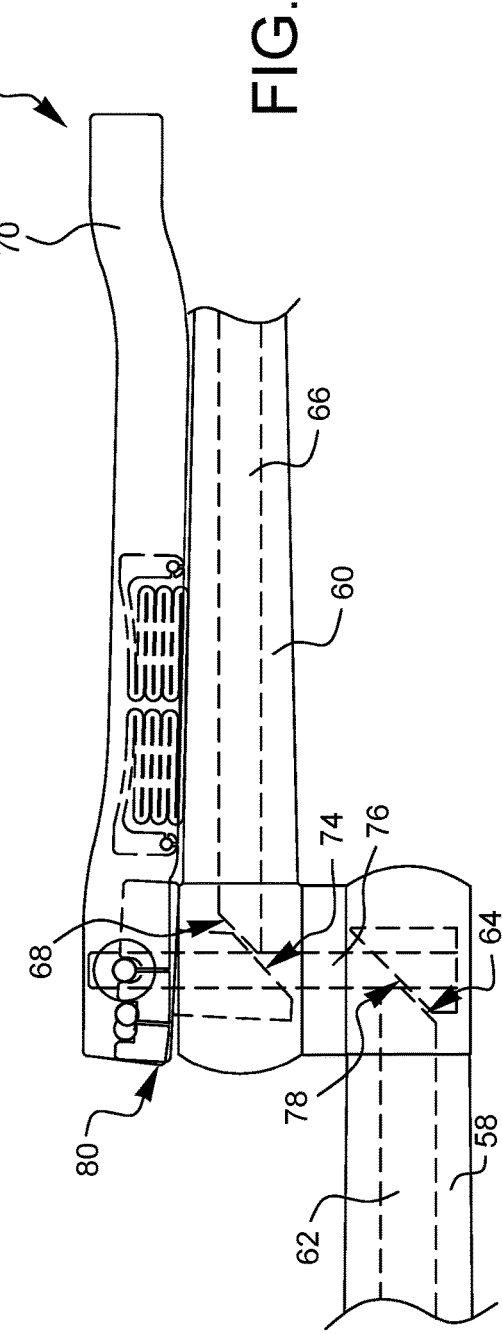

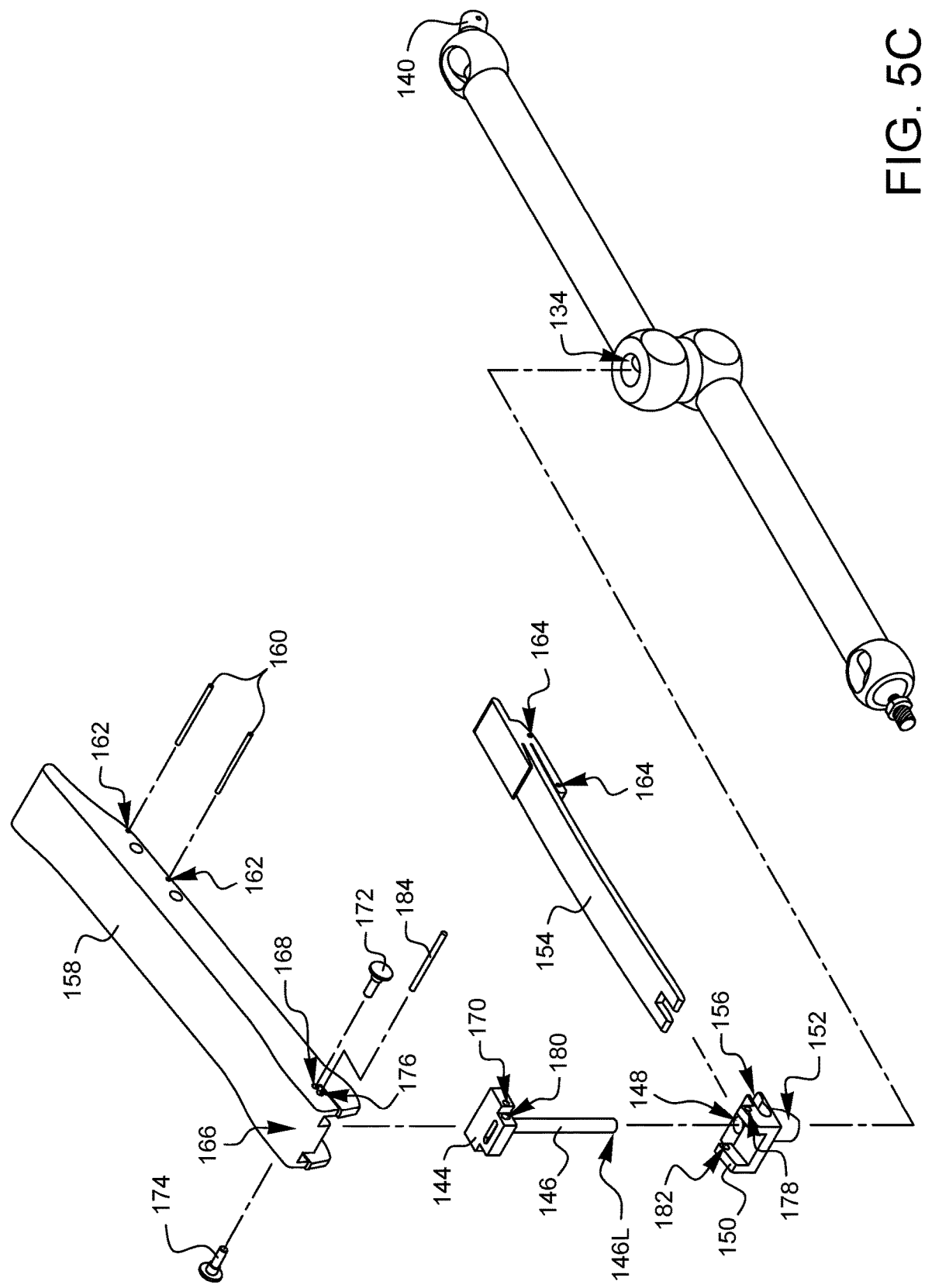

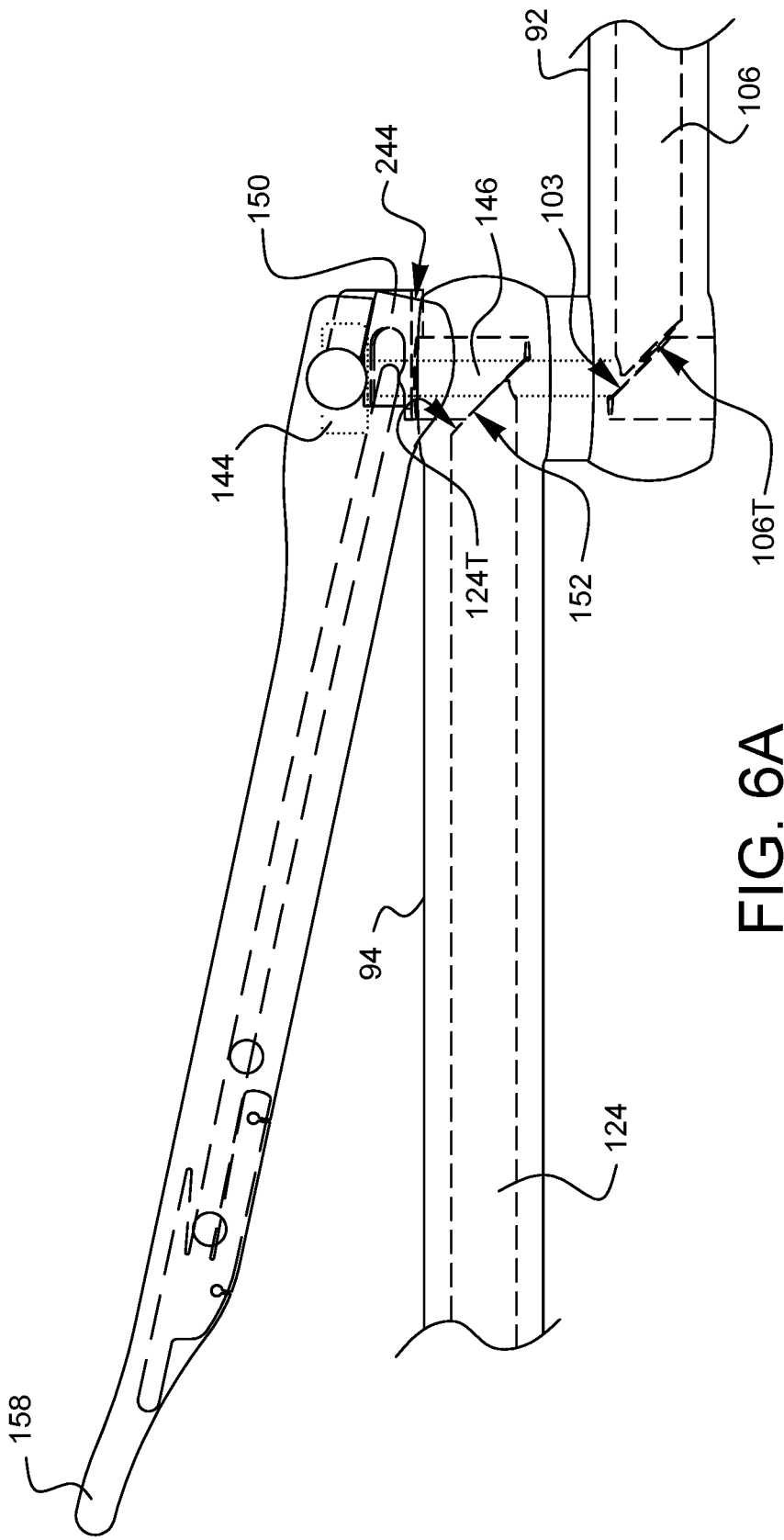

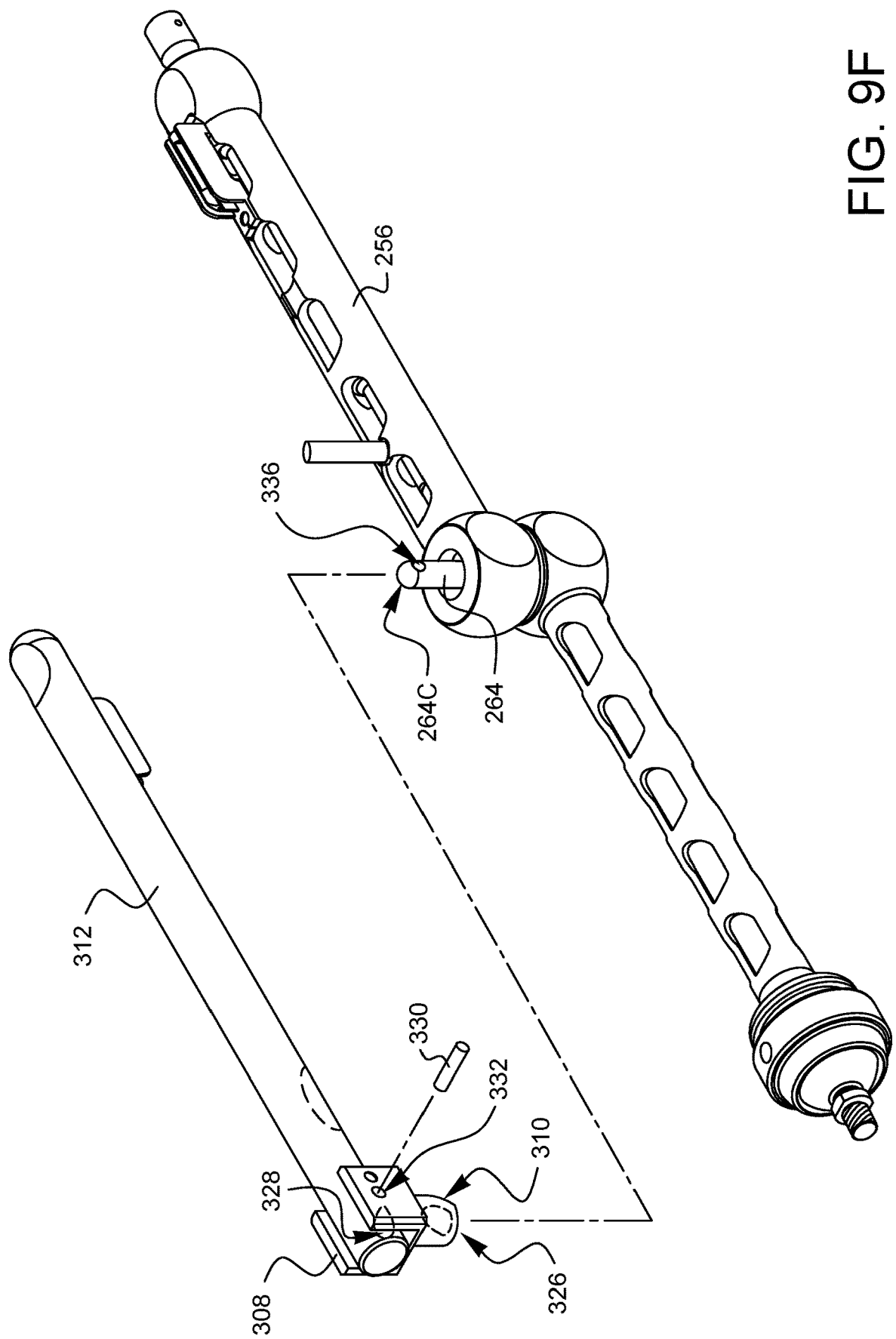

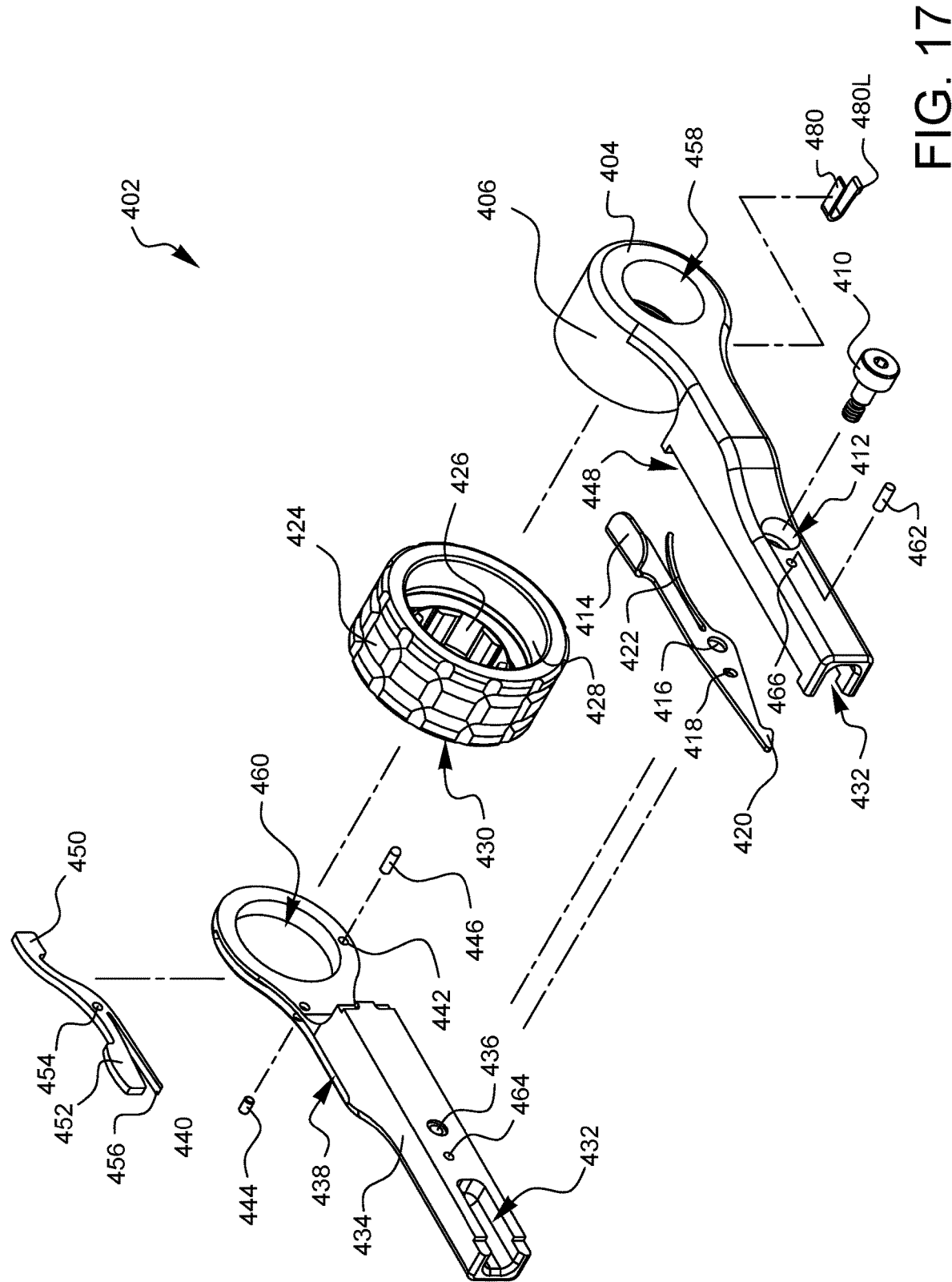

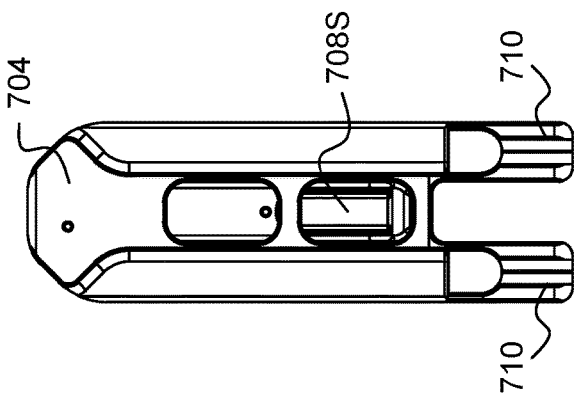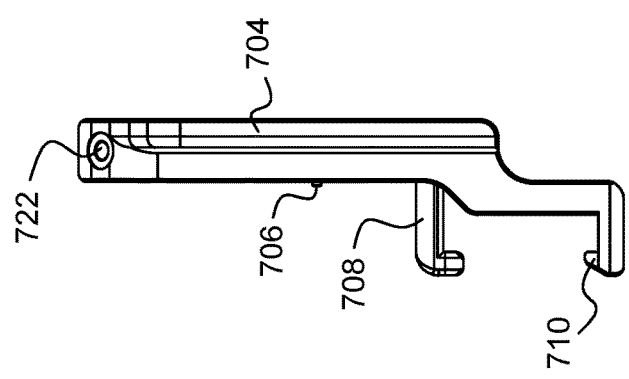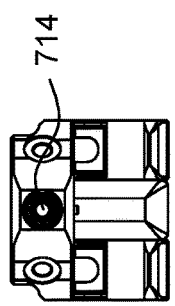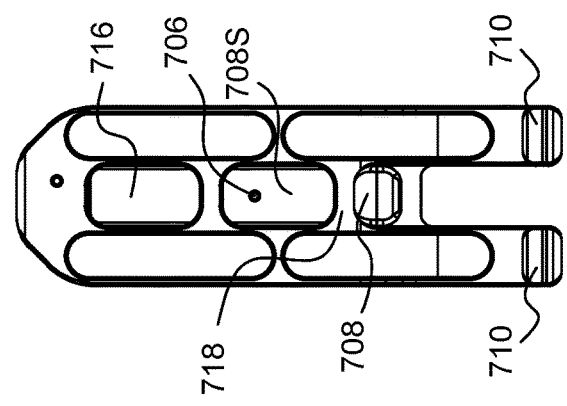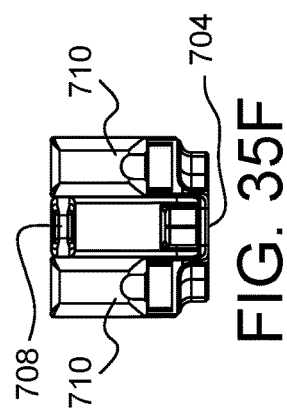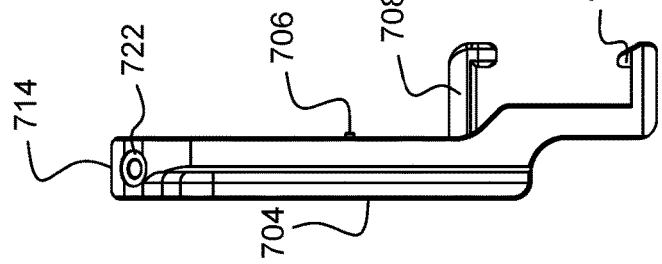

SURGICAL EQUIPMENT HOLDER

RELATED APPLICATIONS

This patent application claims priority to PCT Application PCT/US2018/033288 entitled "SURGICAL EQUIPMENT HOLDER" filed May 17, 2018, which is a continuation-in-part of International Application No. PCT/US2018/030846 filed May 3, 2018, which claims priority to U.S. Provisional Patent Application No. 62/500,972 filed May 3, 2017 and entitled, "SURGICAL EQUIPMENT HOLDER". PCT application PCT/US2018/033288 also claims priority to U.S. Provisional Patent Application No. 62/507,724 filed May 17, 2017, entitled, "SURGICAL EQUIPMENT HOLDER" and to U.S. Provisional Patent Application No. 62/526,329 filed Jun. 28, 2017 and entitled, "SURGICAL EQUIPMENT HOLDER". Applications PCT/US2018/033288, PCT/US2018/030846, 62/500,972, 62/507,724, and 62/526,329 are hereby incorporated by reference in their entirety.

FIELD

The claimed invention relates to surgical devices, and more specifically to an adjustable holder for surgical equipment.

BACKGROUND

Laparoscopic, endoscopic, and other types of minimally invasive surgical procedures often rely on percutaneous introduction of surgical instruments into an internal region of a patient where the surgical procedure is to be performed. Surgeons continue to find it desirable to utilize smaller and smaller access incisions in order to minimize trauma and reduce patient recovery times. Frequently, surgeons will make additional small incisions through which a viewing scope or other surgical equipment may be passed to assist in the operation. In the case of viewing scopes, an assistant may manipulate and/or hold the scope in a fixed position for the surgeon so that the surgeon may look at images, acquired by the scope, on a monitor screen in order to perform the minimally invasive operation. Holders, such as the one illustrated in FIG. 1, may be used in lieu of an assistant to position and hold surgical equipment such as, but not limited to, a viewing scope.

FIG. 1 is a schematic illustration of a prior art equipment holder 20. The equipment holder 20 has a base 22. The base 22 is illustrated schematically, but may be an object with substantial mass compared to what it will be holding so that the equipment holder 20 is stable. Alternately, the base 22 may be a clamp, suction device, magnet, or otherwise have an attachment mechanism for attaching or coupling the equipment holder 20 to a surgical operating table or some other equipment in an operating room. Such bases are known to those skilled in the art.

A ball connector 24 is coupled to the base 22. A first arm 26 is pivotably coupled to the ball connector 24 by a socket 28 on one end of the first arm 26. The socket 28 is sized so that it does not come off the ball connector 24, but otherwise is able to pivot freely in all directions around the ball connector 24. The other end of the first arm 26 terminates in a receiver 30 which has a threaded opening (not visible in FIG. 1) sized to accept a screw (also not visible in FIG. 1) which is attached to control knob 32. The screw 34 attached to control knob 32 can be seen in FIG. 2. FIG. 2 is a partially exploded view of the prior art equipment holder 20 of FIG. 1. When assembled, the screw 34 passes through a clearance hole 36 in the first end 38 of a second arm 40 and is screwed into the threaded opening 42 of receiver 30. A rod 44 is slideable within the first arm 26. The rod 44 may have a cupped end 46 which is designed to help create friction against the ball connector 24 when the rod 44 is pushed towards the ball connector 24. The rod 44 also has a tapered end 48 opposite the cupped end 46. When the screw 34 is not tightened all the way into the threaded opening 42 of the receiver 30, the end of the screw 50 does not exert enough force on the tapered end 48 of the rod 44 to push the rod 44 against the ball connector 24. Furthermore, when the screw 34 is not tightened all the way into the threaded opening 42 of the receiver 30, the second arm 40 is free to rotate around an axis defined by the screw 34. Thus, while the screw 34 is not tightened, a surgeon may use one hand to position the second arm 40 as well as the first arm 26 coupled to it. Then, while using that one hand to maintain the desired position of the arms, the surgeon may use his/her other hand to tighten the control knob 32 to lock the first and second arms of the equipment holder 20 in place. As the control knob 32 is tightened, the end of the screw 50 interferes with the tapered end 48 of the rod 44, pushing the rod 44 axially against the ball connector 24 and fixing the orientation of the first arm 26. Additionally, the tightening of the control knob 32 grips the first end 38 of the second arm 40 between the control knob 32 and the receiver 30, thereby fixing the orientation of the second arm 40 as illustrated in FIG. 1. Unfortunately, this positioning and locking into a desired position takes two hands.

Furthermore, this two-handed adjustment does nothing to adjust an end effector 52 coupled to a second end 54 of the second arm 40. Many prior art equipment holders 20 have an adapter or end effector 52 configured to provide an interface with the surgical tool being held. In the case of a viewing scope, the end effector 52 would have some type of clamp or set screw, or other attachment features which actually hold the viewing scope. In FIGS. 1 and 2, the end effector 52 is simply shown as a generic block, but some end effectors may also have a separate control knob whereby the angle of the device being held by the end effector 52 can be changed relative to the second arm 40. Such an adjustment, while providing positioning flexibility, would also require a pair of hands to work and could not be done at the same time as the adjustment of the first and second arm 26, 40 positions unless two people were involved at the same time. Therefore, it would be desirable to have an improved surgical equipment holder, especially one which was simpler to adjust.

SUMMARY

A surgical equipment holder is disclosed. The surgical equipment holder has a first arm pivotable relative to a base, a second arm pivotably coupled to the first arm, an end effector pivotable relative to the second arm, and a lever movable between a locked position and an unlocked position. The lever is configured such that the first arm does not pivot relative to the base, the second arm does not pivot relative to the first arm, and the end effector does not pivot relative to the second arm when the lever is in the locked position; and the first arm may be pivoted relative to the base, the second arm may be pivoted relative to the first arm, and the end effector may be pivoted relative to the second arm when the lever is in the unlocked position.

Another surgical equipment holder is also disclosed. The surgical equipment holder includes a first arm pivotable relative to a base, a second arm pivotably coupled to the first arm, an end effector pivotable relative to the second arm, and a lever movable between a locked position and an unlocked position. The lever is configured such that the first arm does not pivot relative to the base, the second arm does not pivot relative to the first arm, and the end effector may be pivoted relative to the second arm when the lever is in the locked position. The lever is also configured such that the first arm may be pivoted relative to the base, the second arm may be pivoted relative to the first arm, and the end effector may be pivoted relative to the second arm when the lever is in the unlocked position.

Another surgical equipment holder is also disclosed. The surgical equipment holder has a first arm pivotable relative to a base, a second arm pivotably coupled to the first arm and an end effector pivotable relative to the second arm. The end effector is coupled to one of a group including an endoscope, a rib retractor, an apparatus for suture management as well as combinations thereof. The surgical instrument holder also includes a lever movable between a locked position and an unlocked position and configured such that the first arm does not pivot relative to the base, the second arm does not pivot relative to the first arm, and the end effector does not pivot relative to the second arm when the lever is in the locked position. The lever is also configured such that the first arm may be pivoted relative to the base, the second arm may be pivoted relative to the first arm, and the end effector may be pivoted relative to the second arm when the lever is in the unlocked position. The surgical equipment holder also includes a tension rod having a spherical stop end in communication with the first arm, the second arm and the lever; and a spacing washer having a convex outward surface configured such that the spacing washer shares an assembled center point which is approximately coincident with the center of the spherical stop end of the tension rod. The locking mechanism of the surgical instrument holder includes a latch coupled to the lever and a catch coupled to the second arm, configured such that the locking mechanism is engaged by moving the lever towards the second arm and the locking mechanism is disengaged by moving the lever towards the second arm when in the locked position.

BRIEF DESCRIPTION OF THE DRAWINGS

FIG. 3A is a side view of a portion of the improved embodiment of a surgical equipment holder in an unlocked position.

FIG. 3B is a side view of a portion of the surgical equipment holder from FIG. 3A in a locked position.

FIGS. 5A-5D are a series of exploded perspective views showing how the surgical equipment holder of FIG. 4, not including the base, is put together.

FIGS. 6A and 6B are side views illustrating the operation of the lever of the surgical equipment holder of FIG. 5E in locked and unlocked positions, respectively.

FIGS. 9A-9F are a series of exploded perspective views showing the assembly of the adjustable arms for the surgical equipment holder of FIG. 8.

Figure 13A:
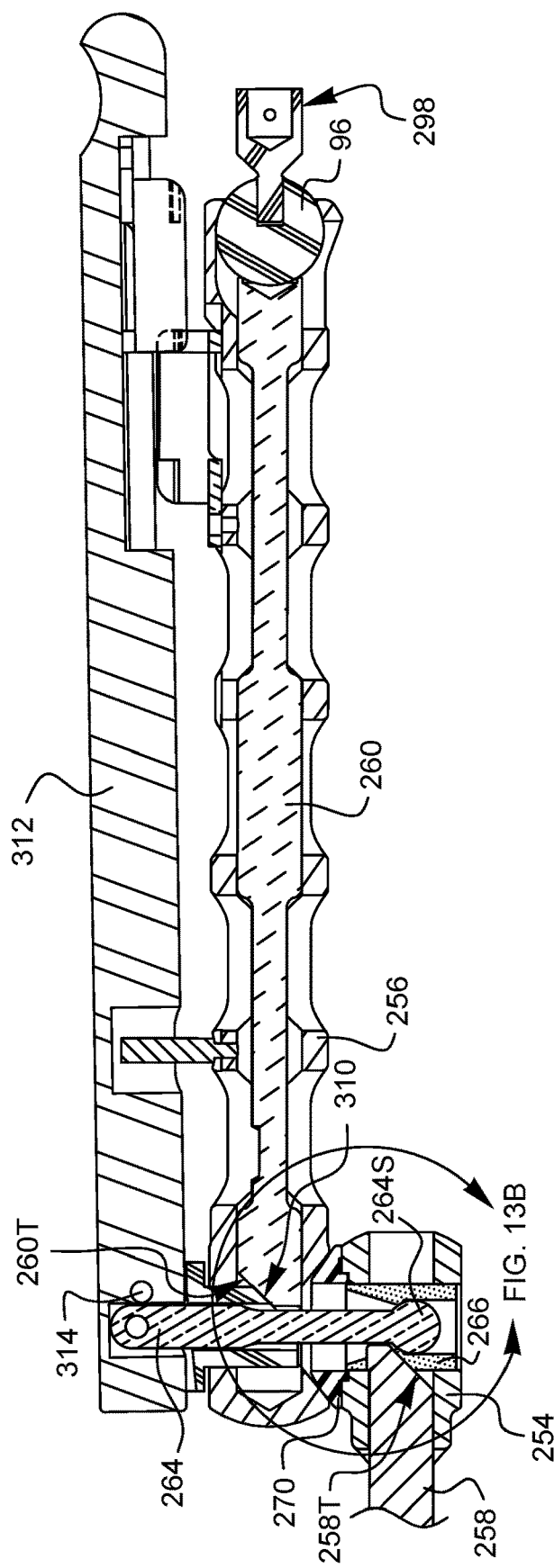
FIG. 13A is a side cross-sectional view of a portion of the surgical equipment holder of FIG. 8 with the lever in a locked position.

13B is an enlarged side cross-sectional view of a portion of a middle joint interface between the first and second arms of the surgical equipment holder of FIG. 13A a locked state.

Figure 14:
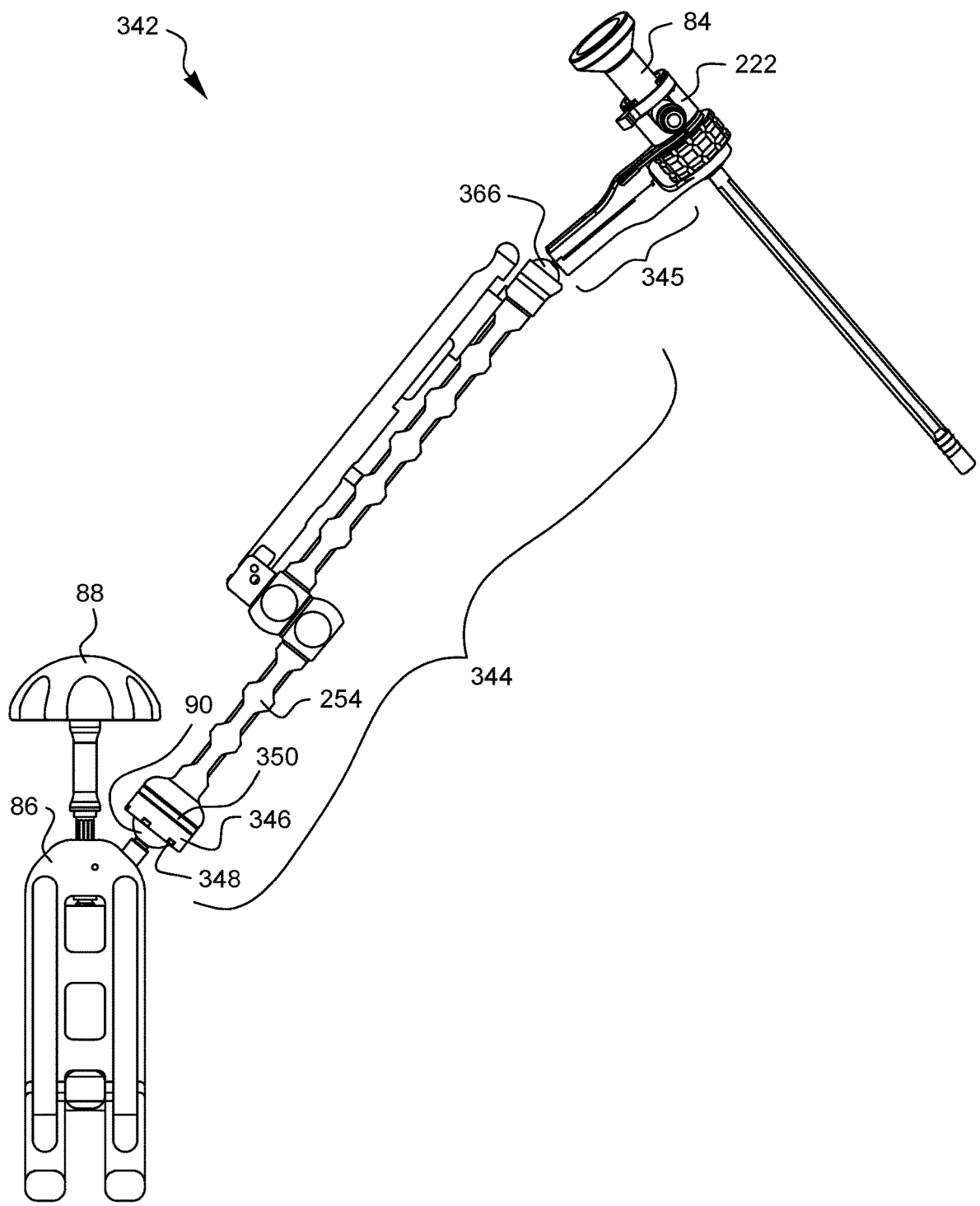

FIG. 14 is a side view of a further improved embodiment of a surgical equipment holder, also shown holding an endoscope.

FIGS. 15A-15E are a series of exploded perspective views showing the assembly of the adjustable arms for the surgical equipment holder of FIG. 14.

Figure 15A:
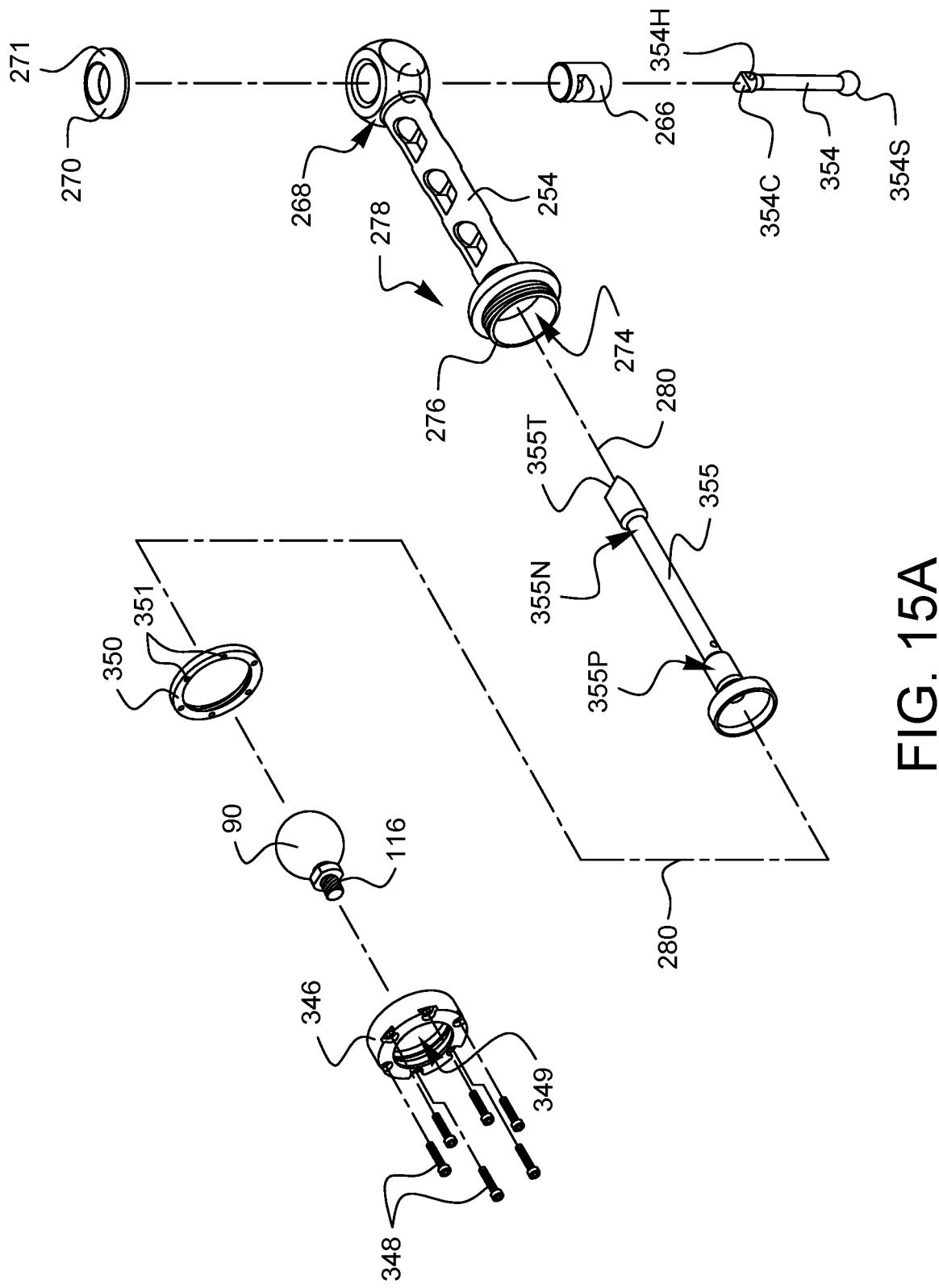
Figure 15B:
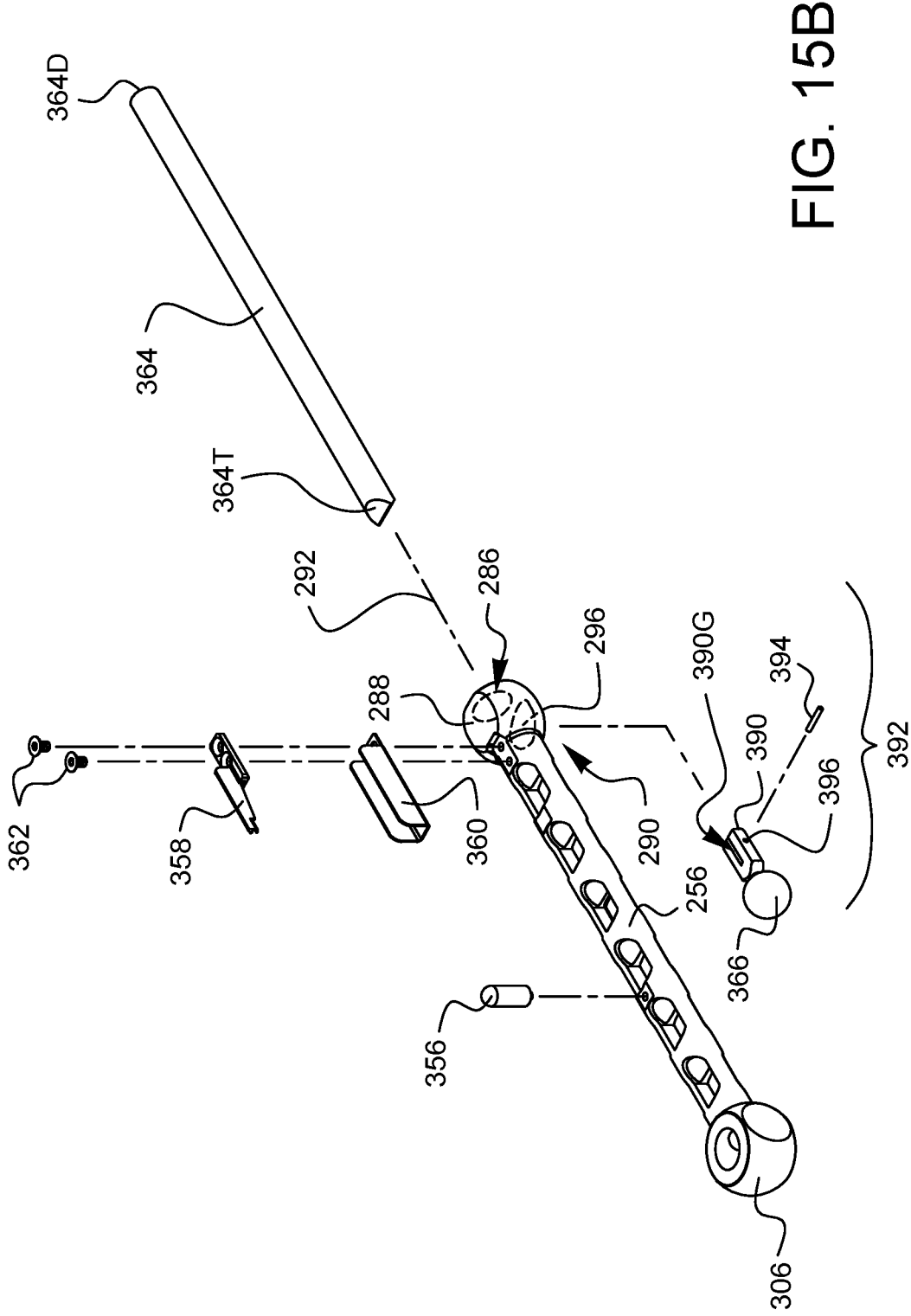
Figure 15C:
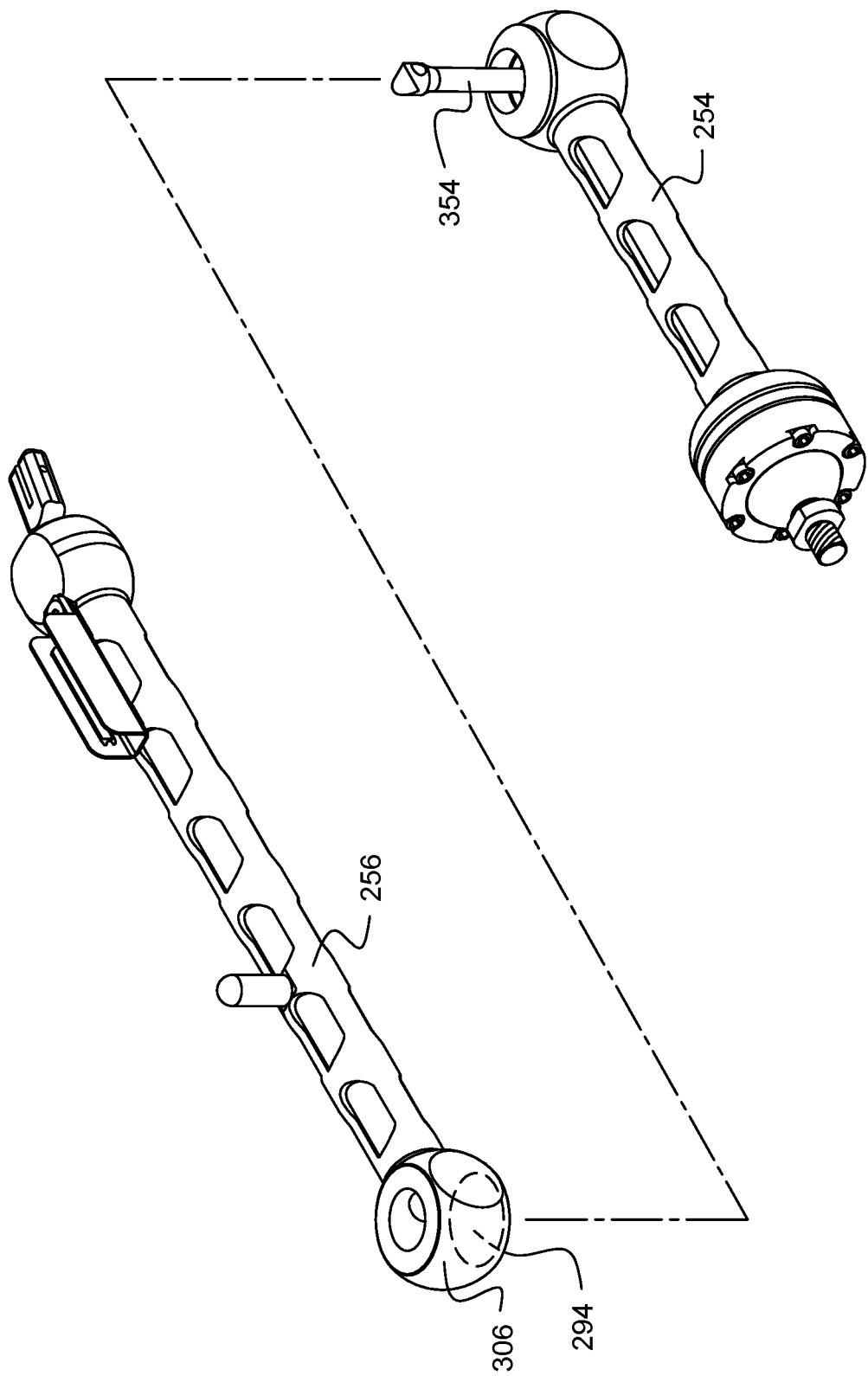
Figure 15D:
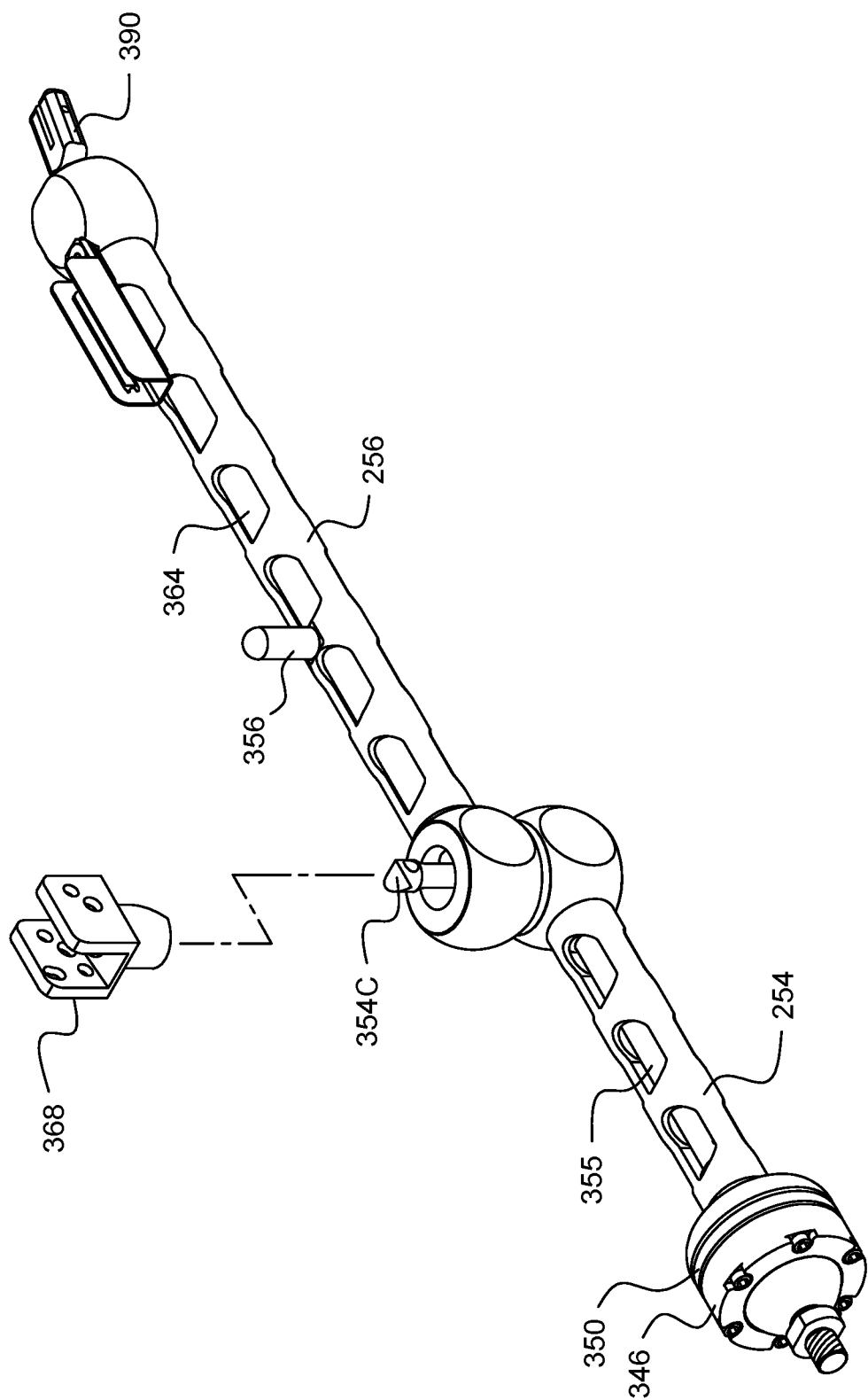
Figure 15E:
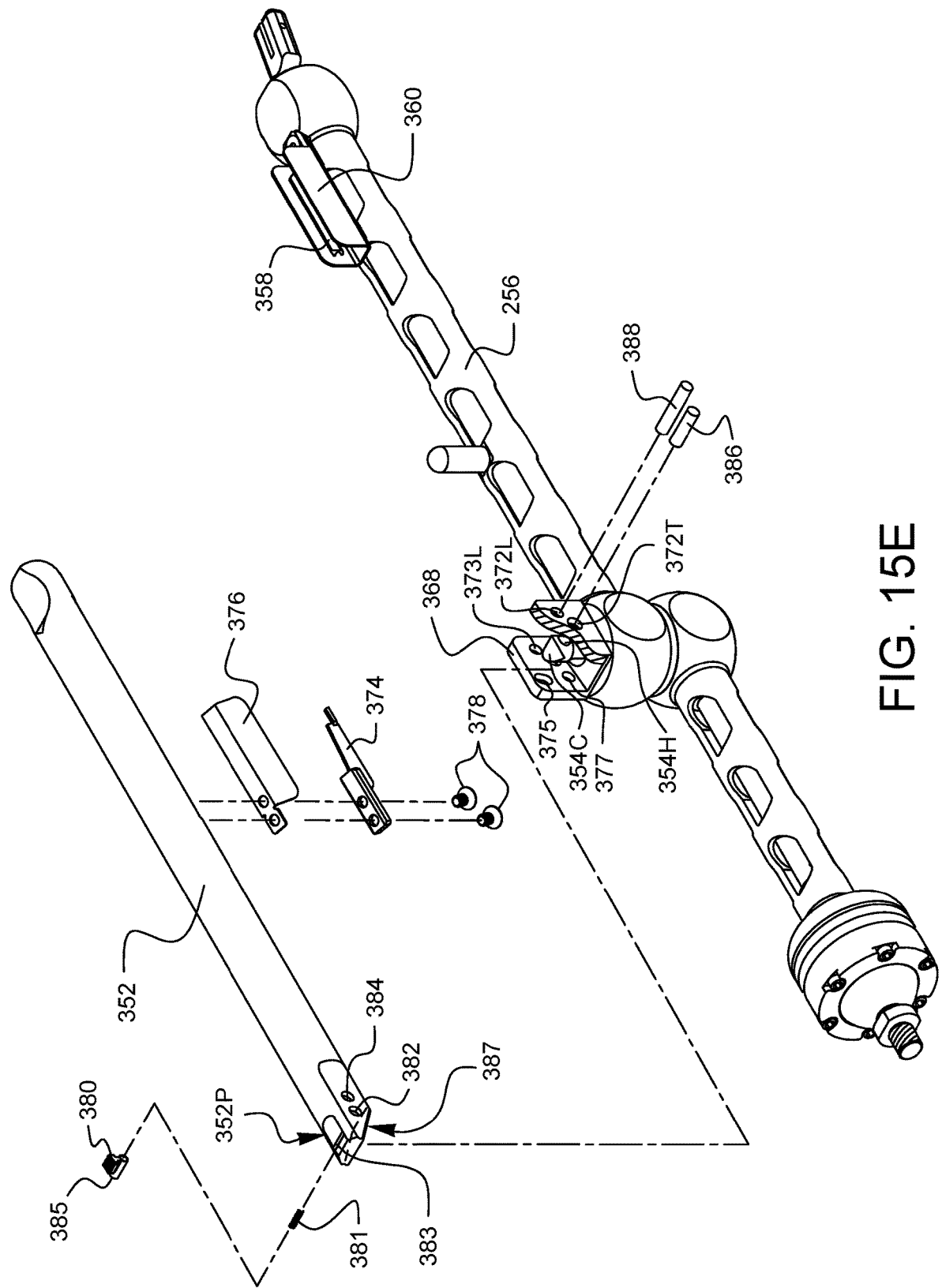
Figure 15F:
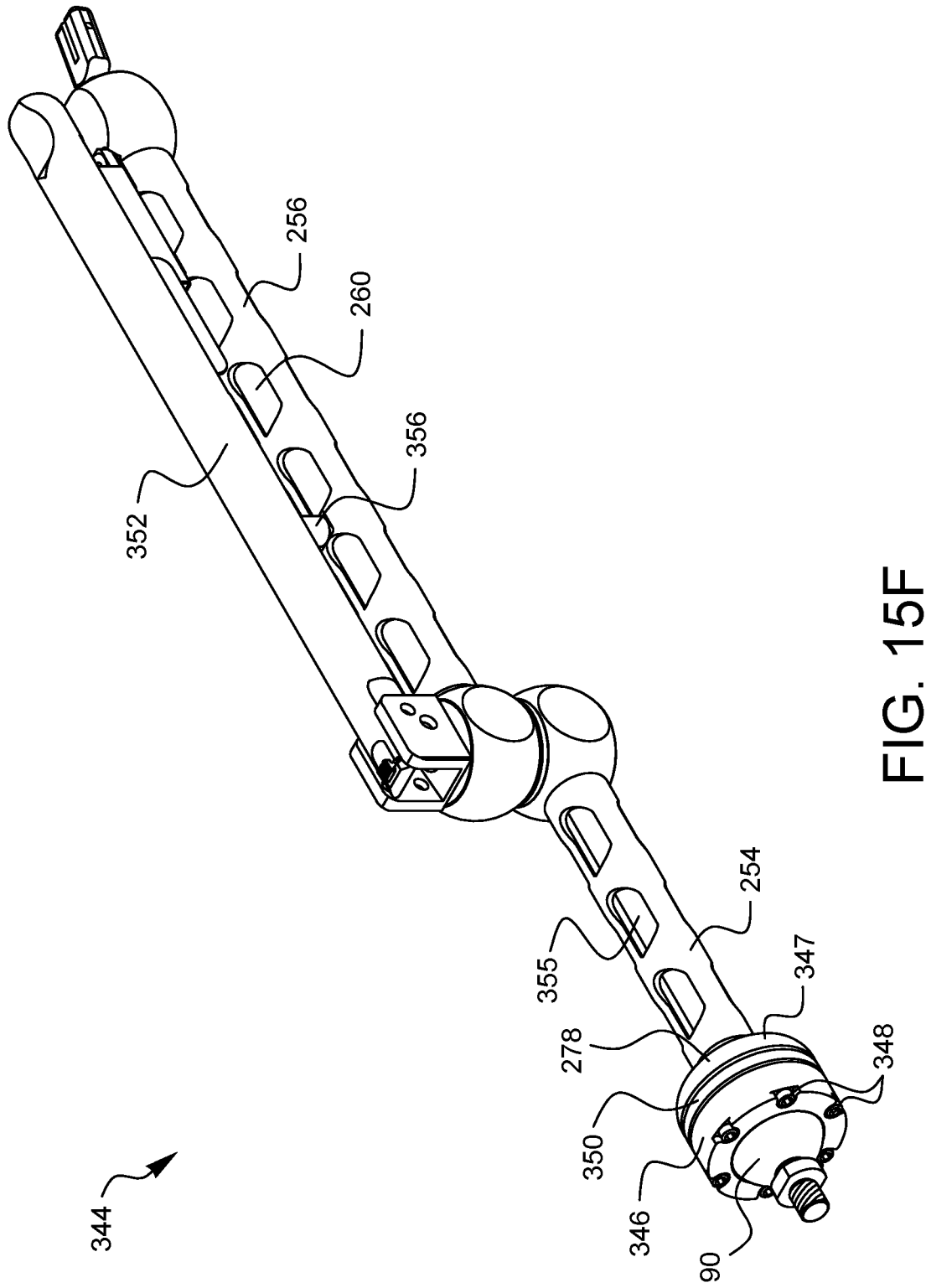

FIG. 15F is a perspective view of the adjustable arms of the surgical equipment holder of FIG. 14.

Figure 16A:
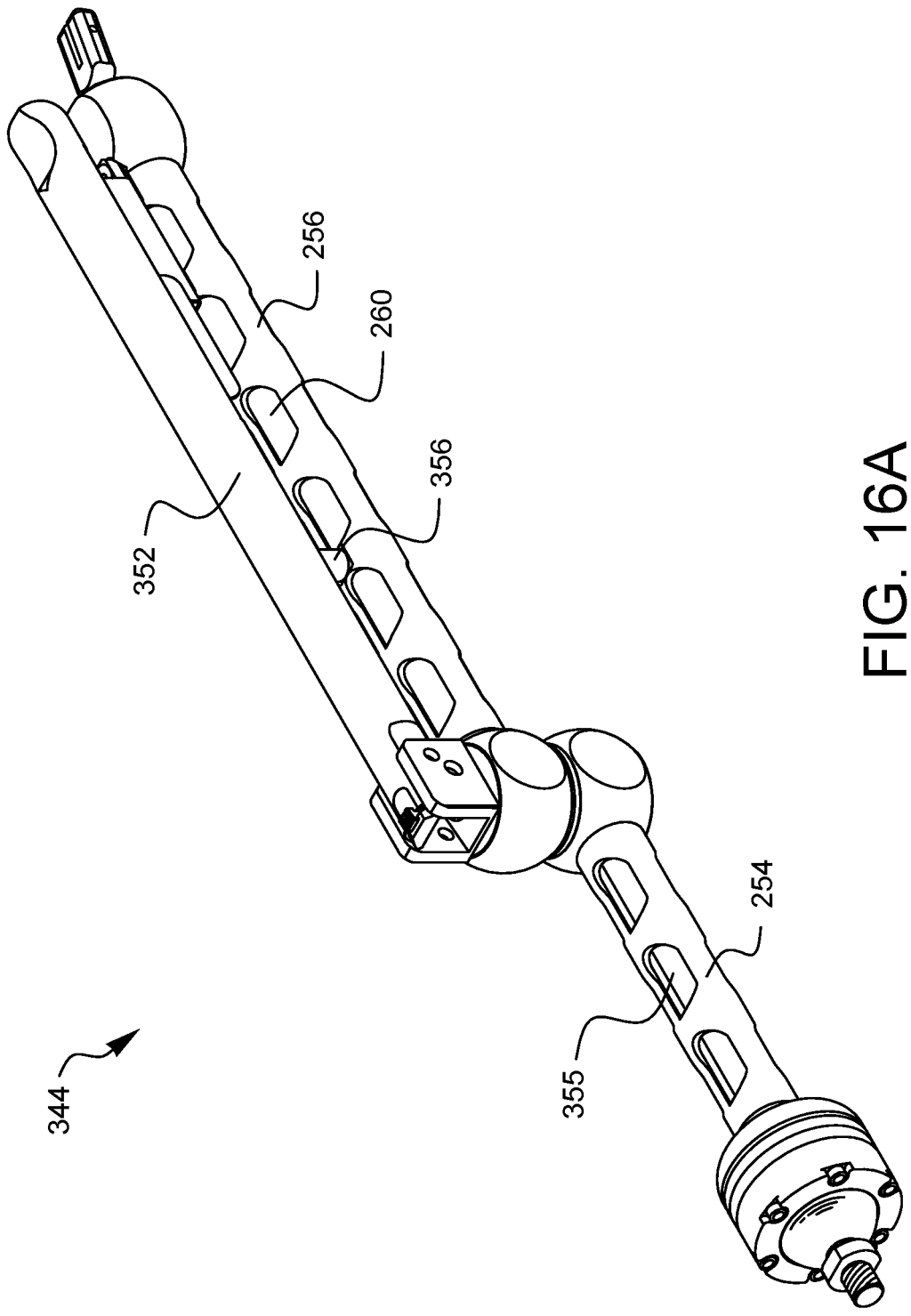
Figure 16B:
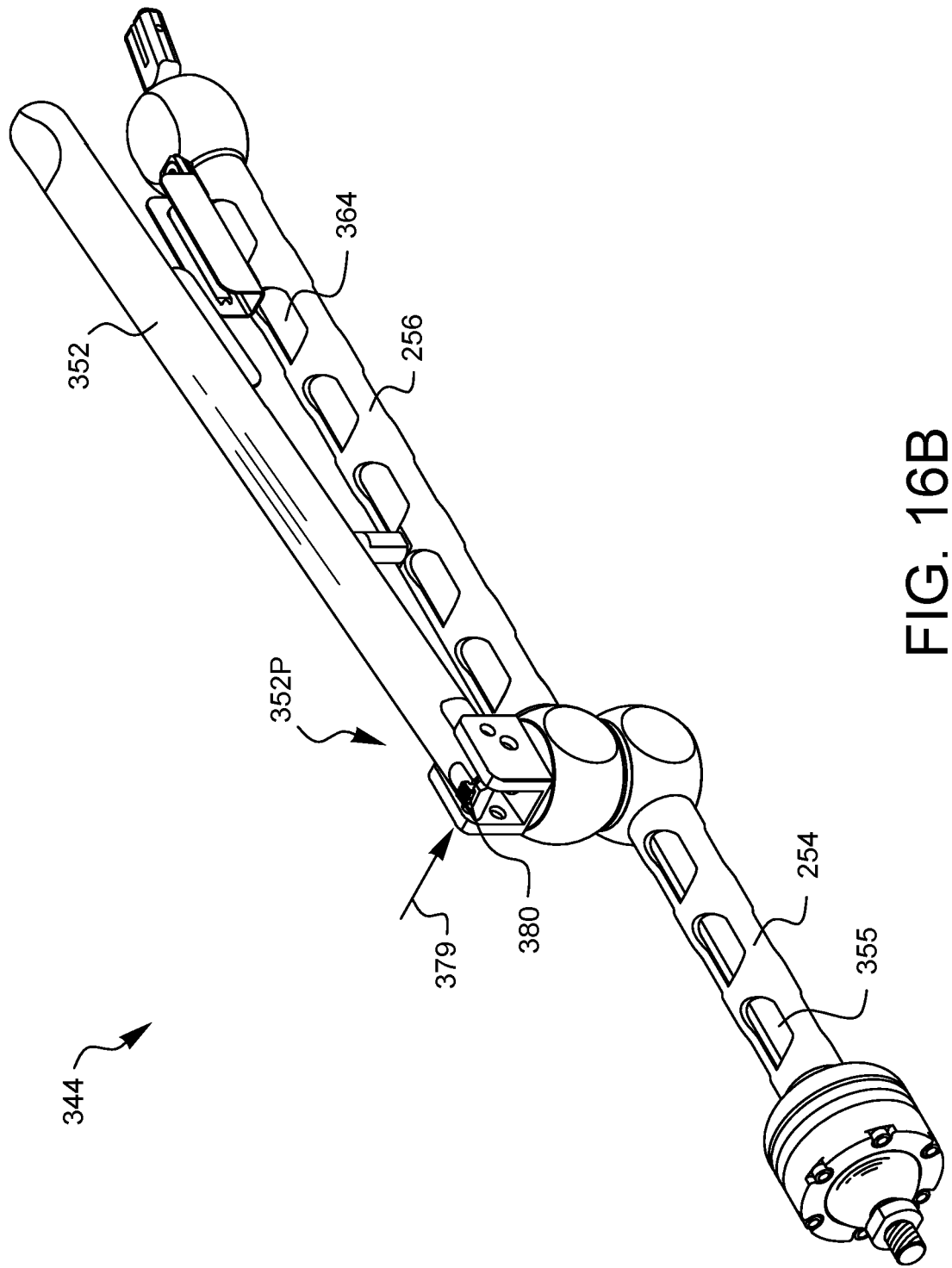
Figure 16C:
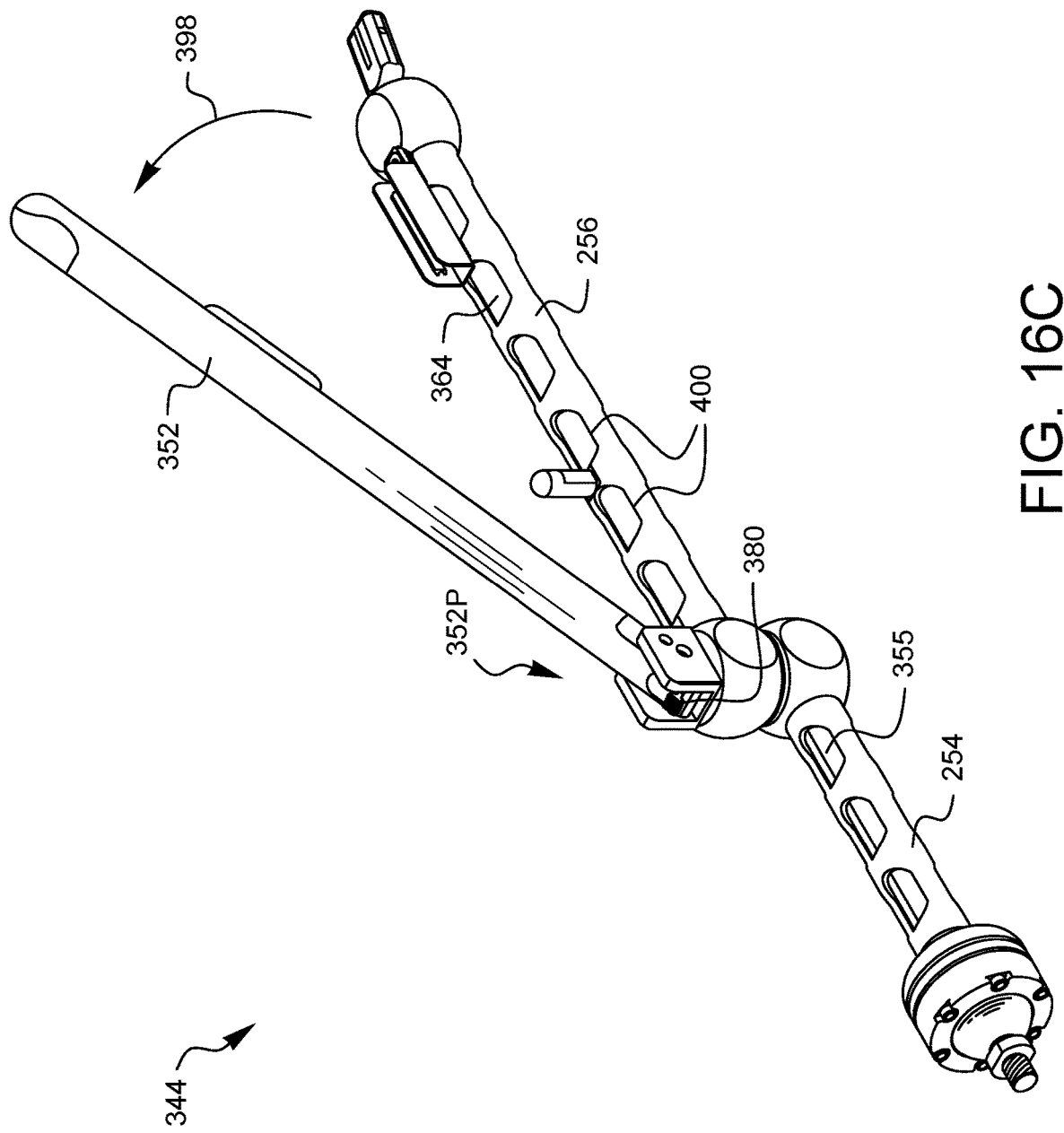

FIG. 16A-16C are perspective views of adjustable arms of the surgical equipment holder of FIG. 14 with the lever shown in locked, unlocked and cleaning positions, respectively.

FIG. 17 is an exploded view showing the assembly of one embodiment of an instrument adapter for a surgical equipment holder.

Figure 18A:
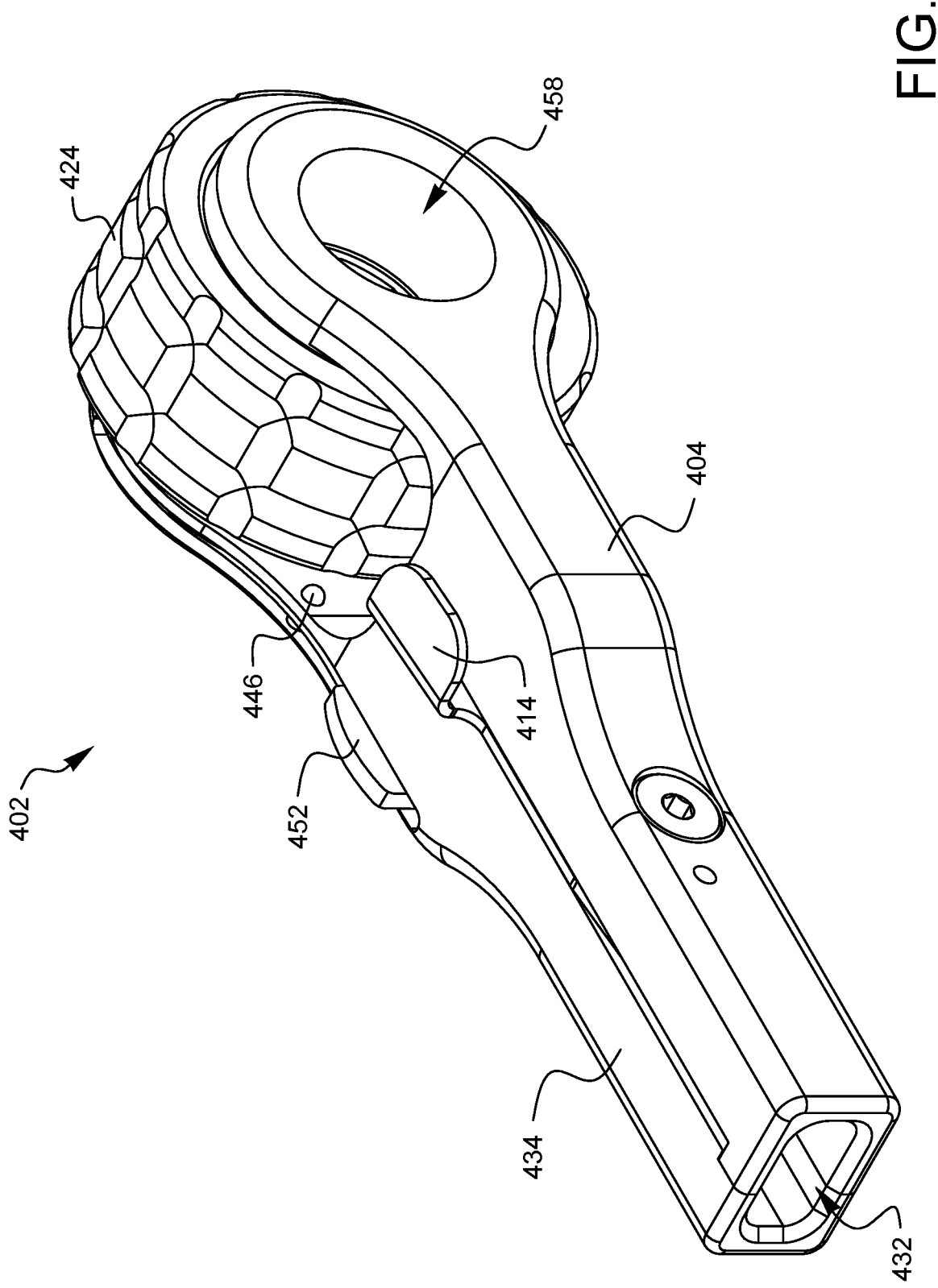

FIG. 18A is a perspective view of the assembled instrument adapter of FIG. 17.

Figure 18B:
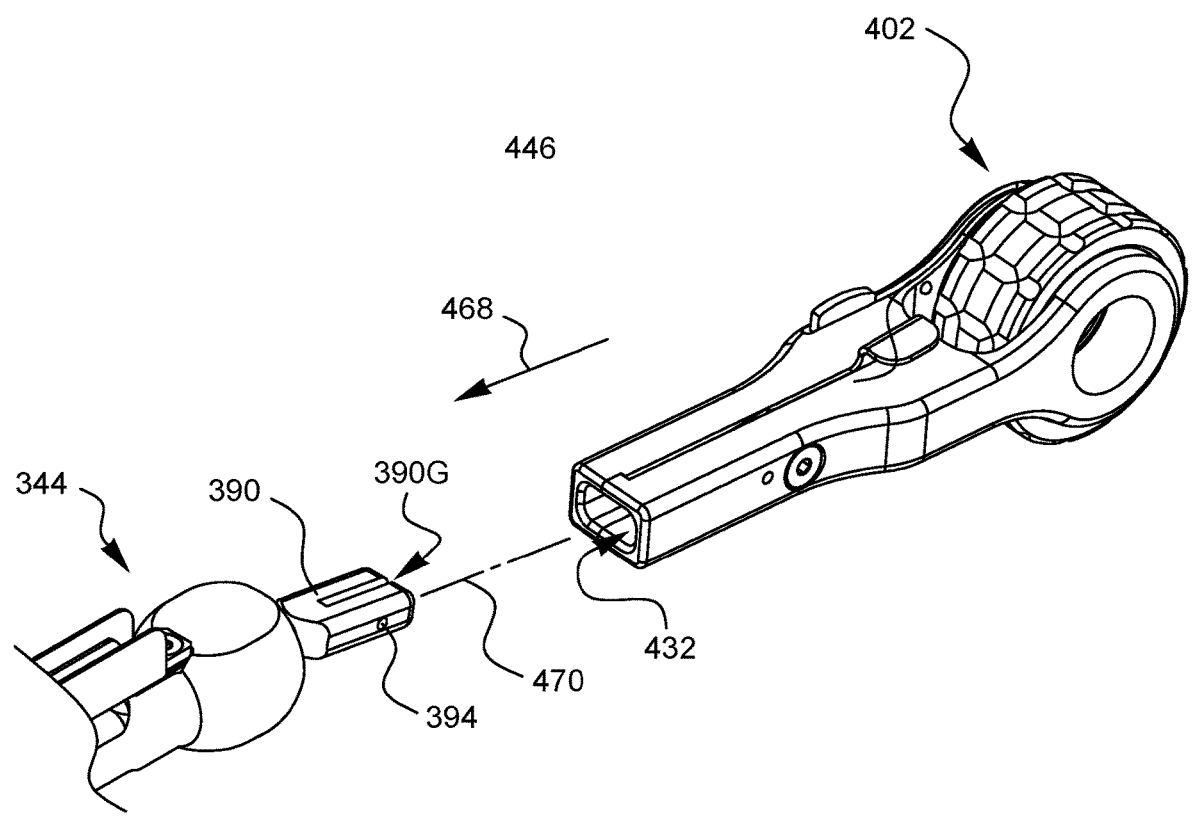

FIG. 18B is a cross-sectional view of the instrument adapter of FIG. 17, demonstrating the latching mechanism of the instrument adapter to the surgical equipment holder of FIG. 14.

Figure 19:
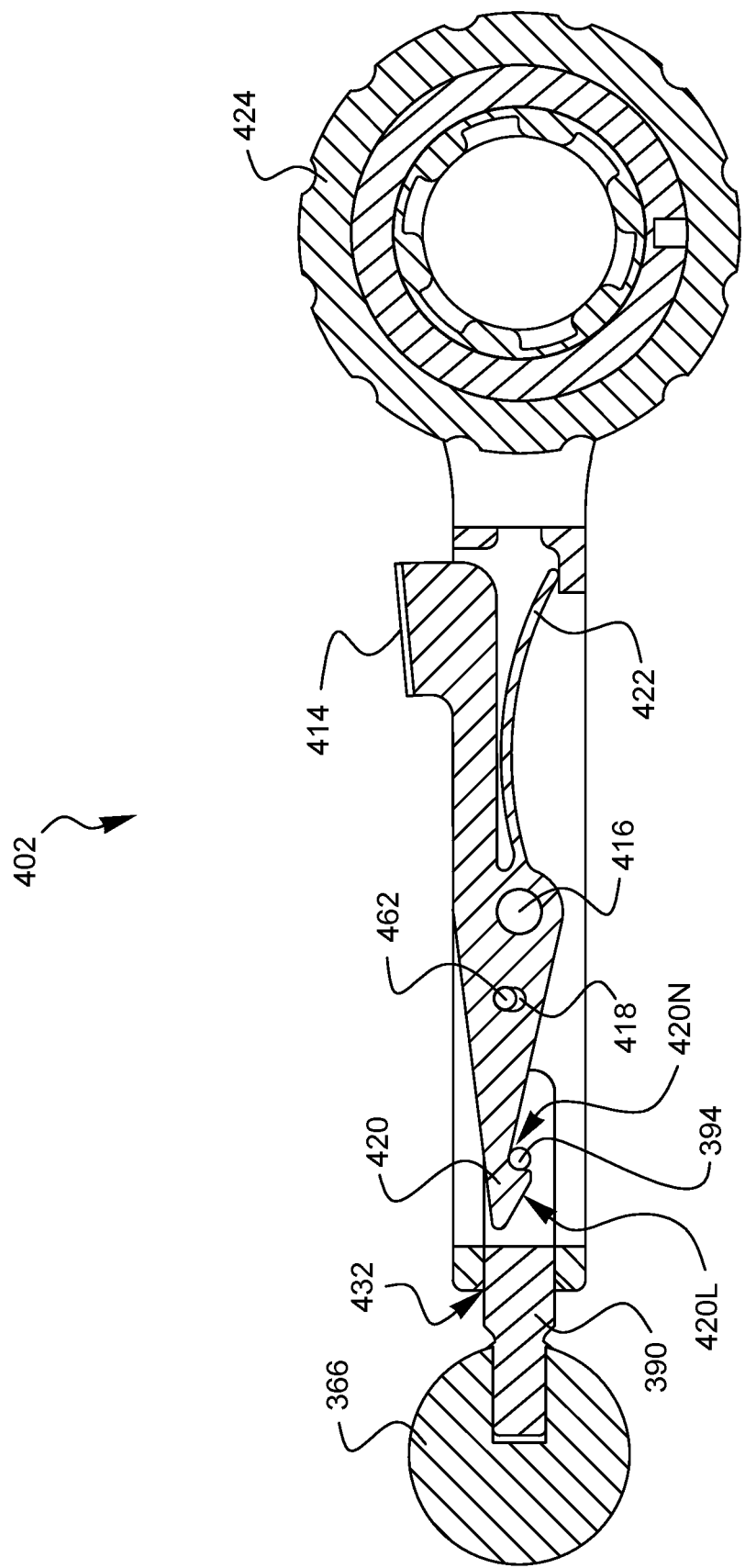

FIG. 19 is a focused perspective view of the end of the adjustable arms of FIG. 15F, illustrating how an embodiment of the instrument adapter of FIG. 18A connects to the surgical equipment holder of FIG. 14.

Figure 20:
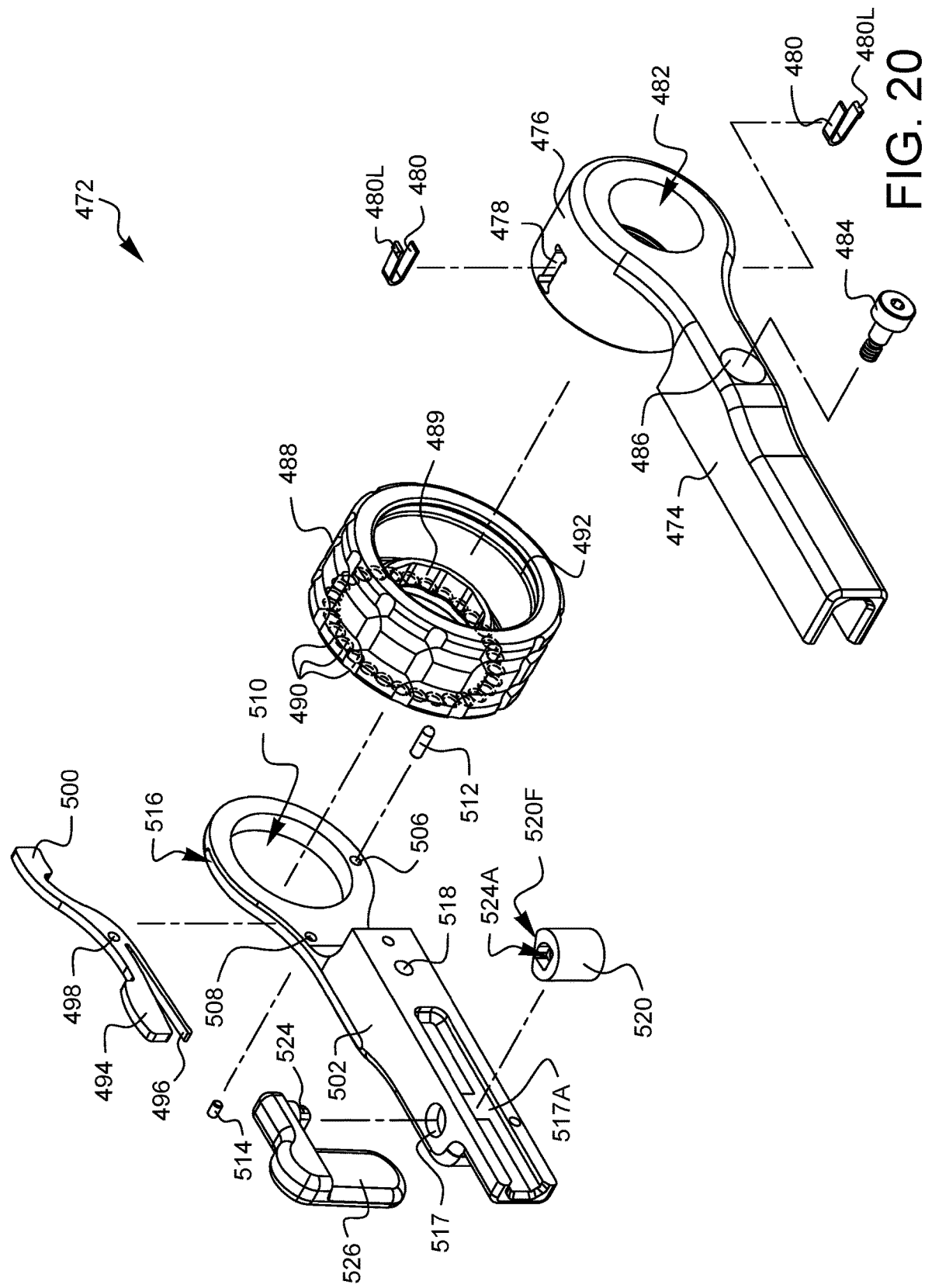

FIG. 20 is an exploded view of another embodiment of an instrument adapter for a surgical equipment holder.

Figure 21:
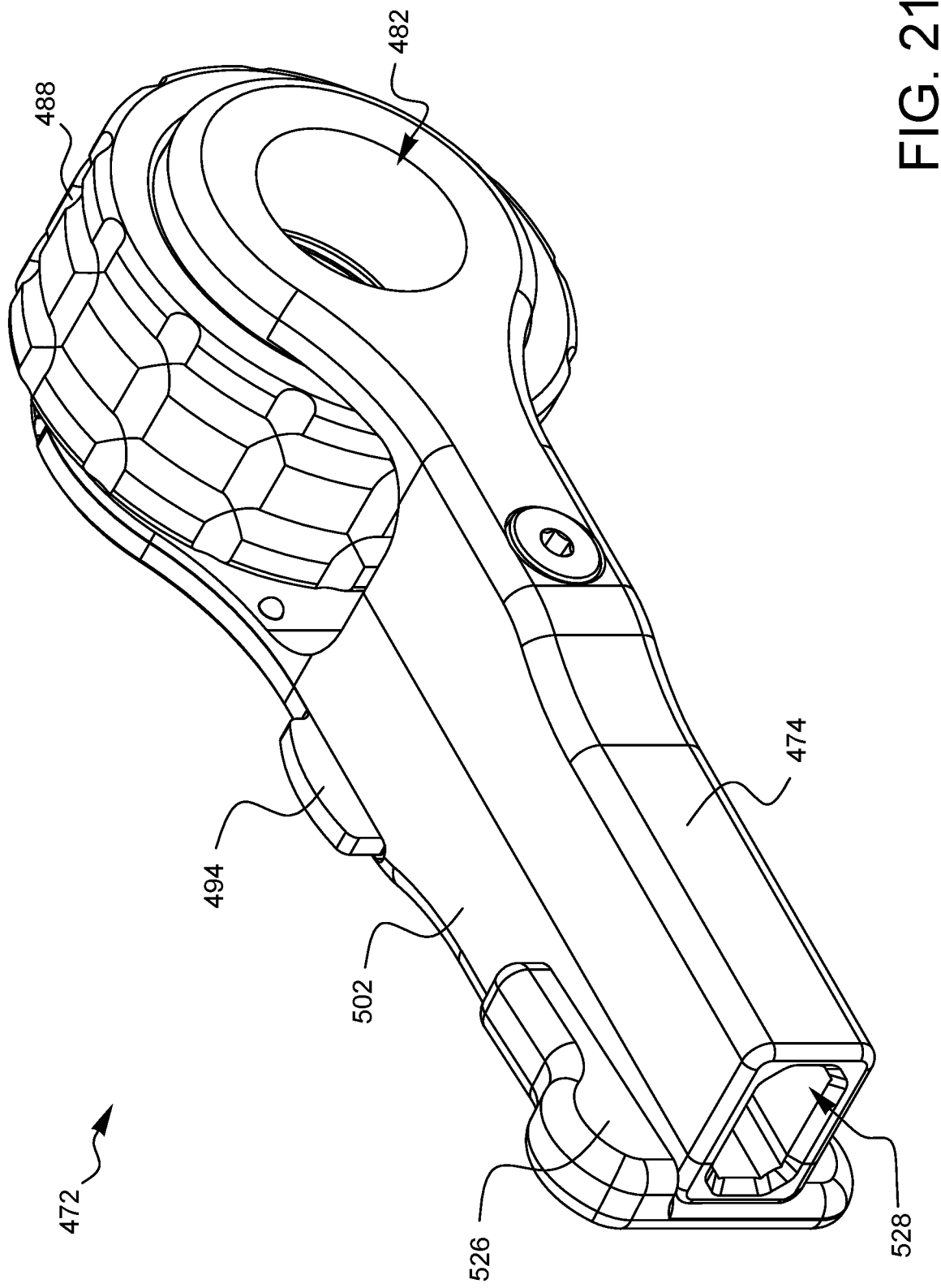

FIG. 21 is a perspective view of the assembled instrument adapter of FIG. 20.

Figure 22A:
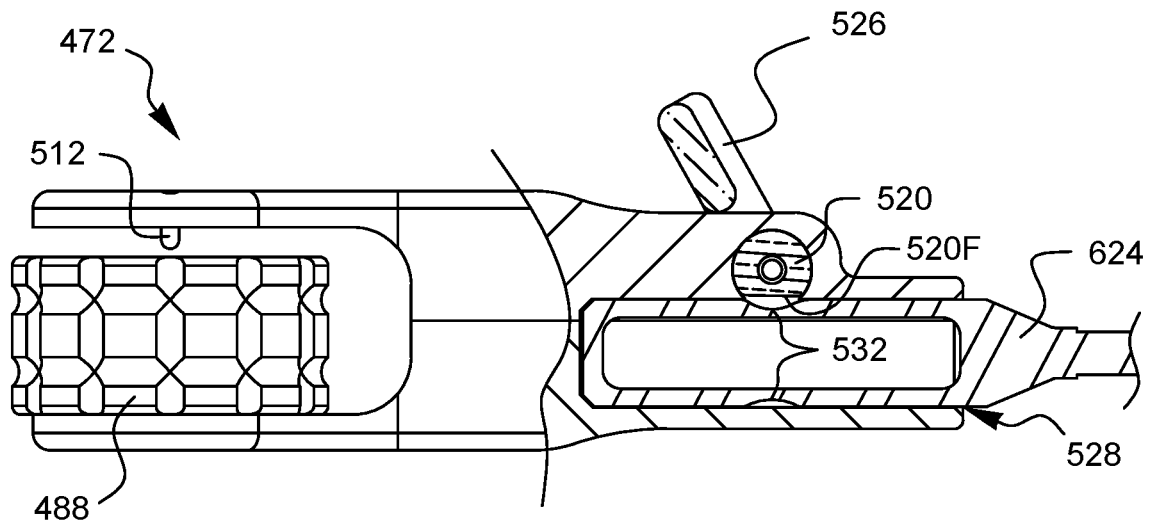
Figure 22B:
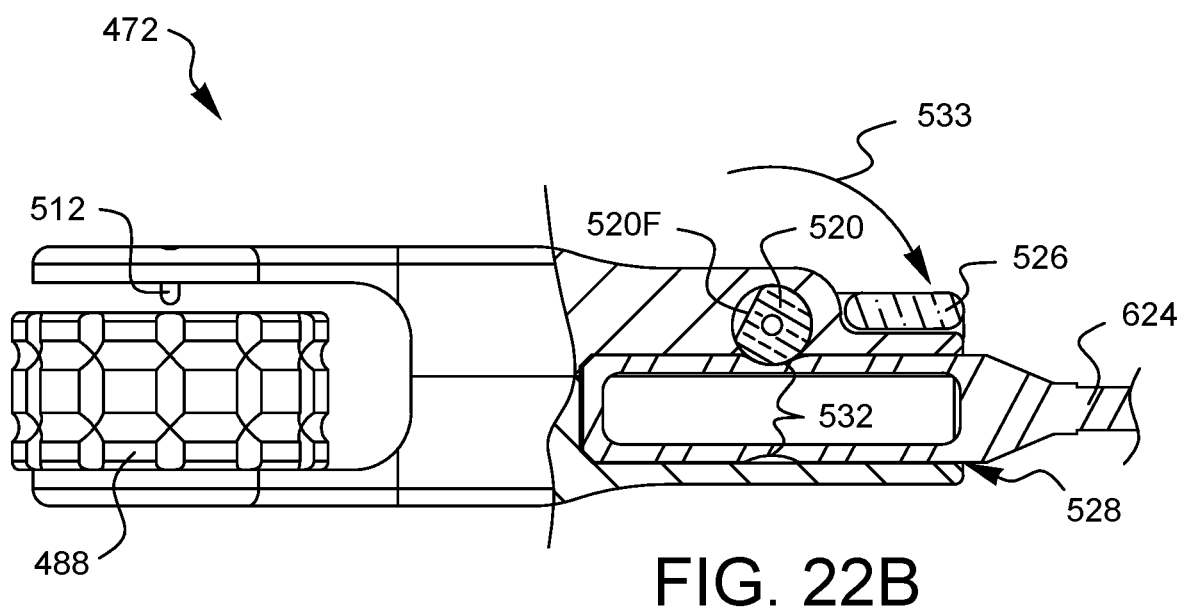

FIGS. 22A and 22B are partial cross-sectional views of the instrument adapter of FIG. 21 in an unlocked and locked state, respectively.

Figure 23:
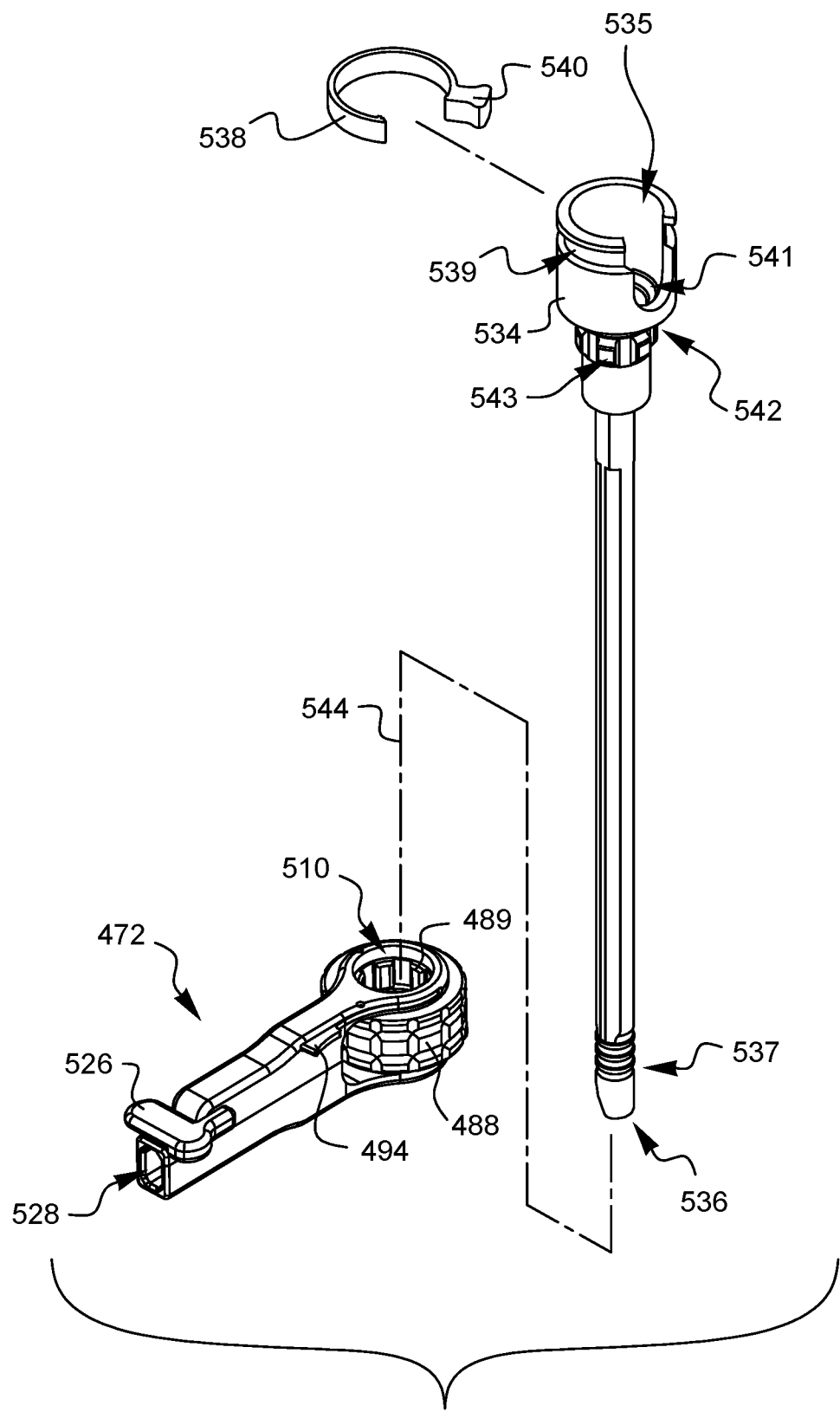

FIG. 23 is a perspective view detailing the insertion of a cannula into the instrument adapter of FIG. 20.

Figure 24A:
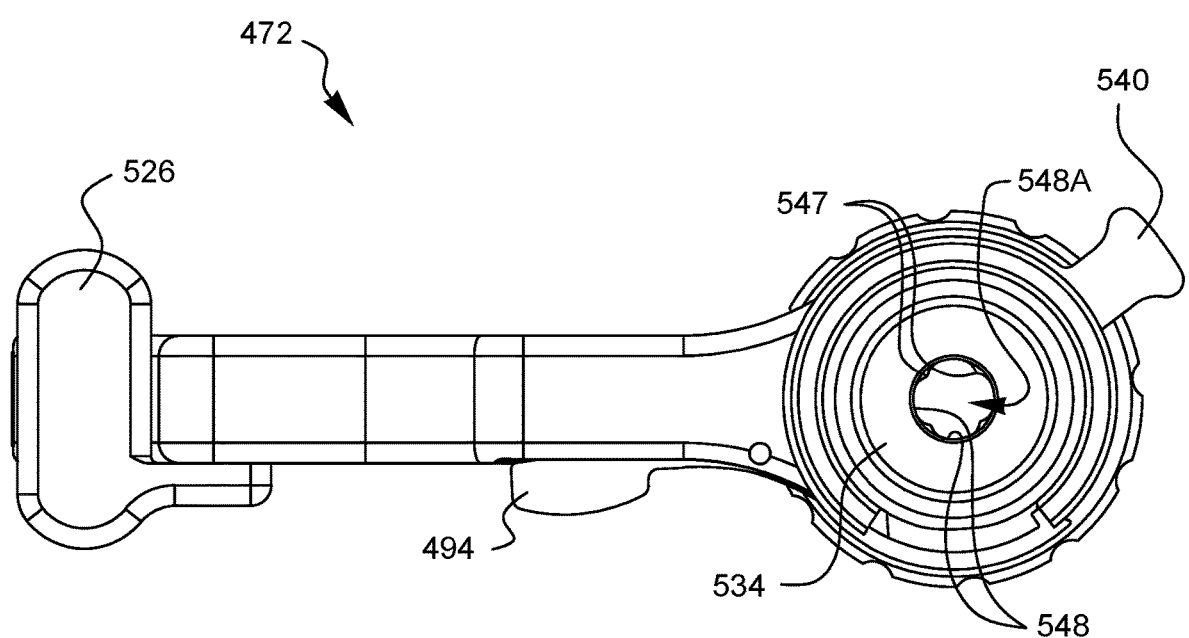

FIG. 24A is a top-end elevational view of the instrument adapter and cannula of FIG. 23.

Figure 24B:
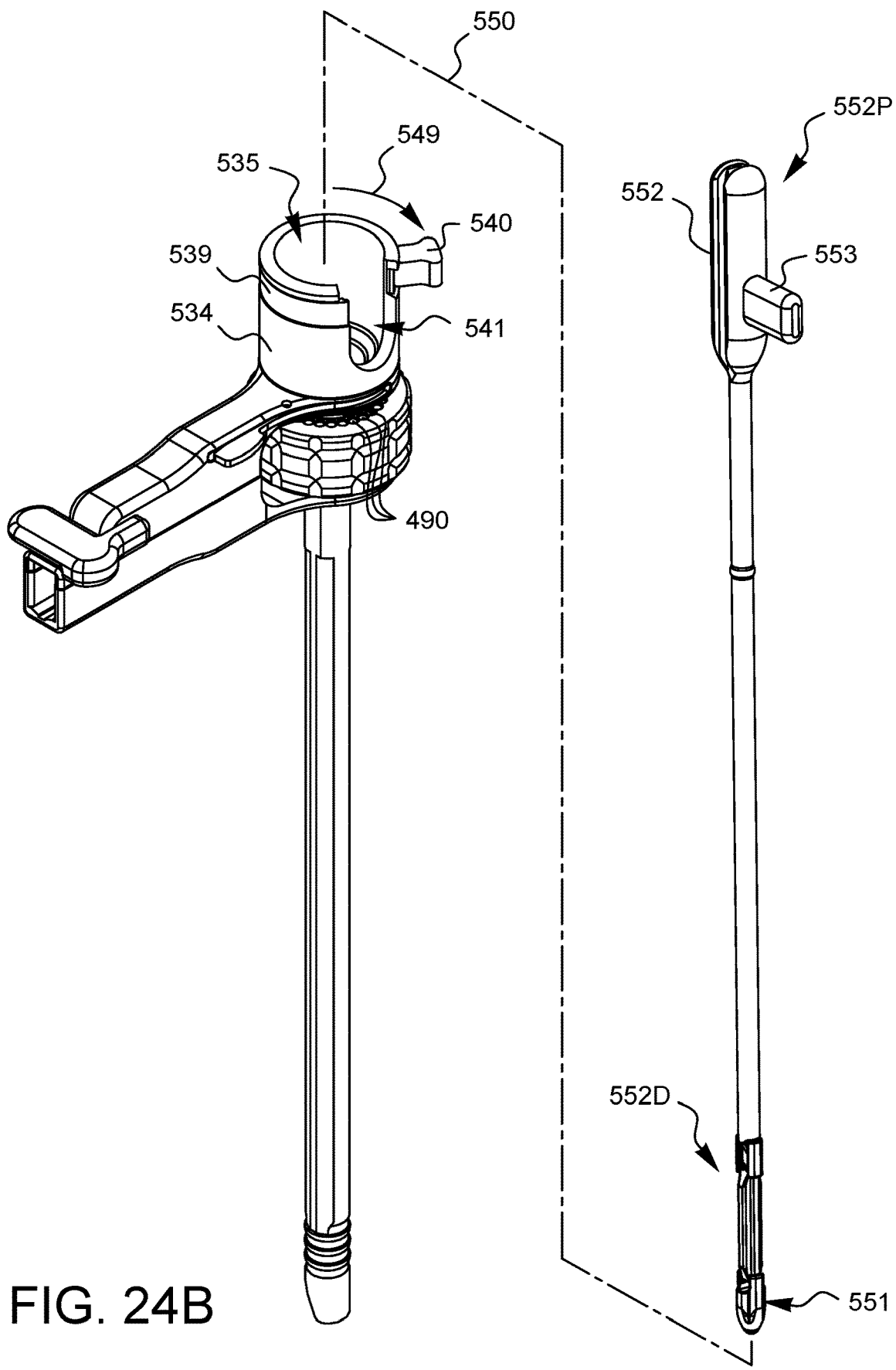

FIG. 24B is a perspective view detailing the insertion of an obturator into the cannula and instrument adapter of FIG. 23.

Figure 25:
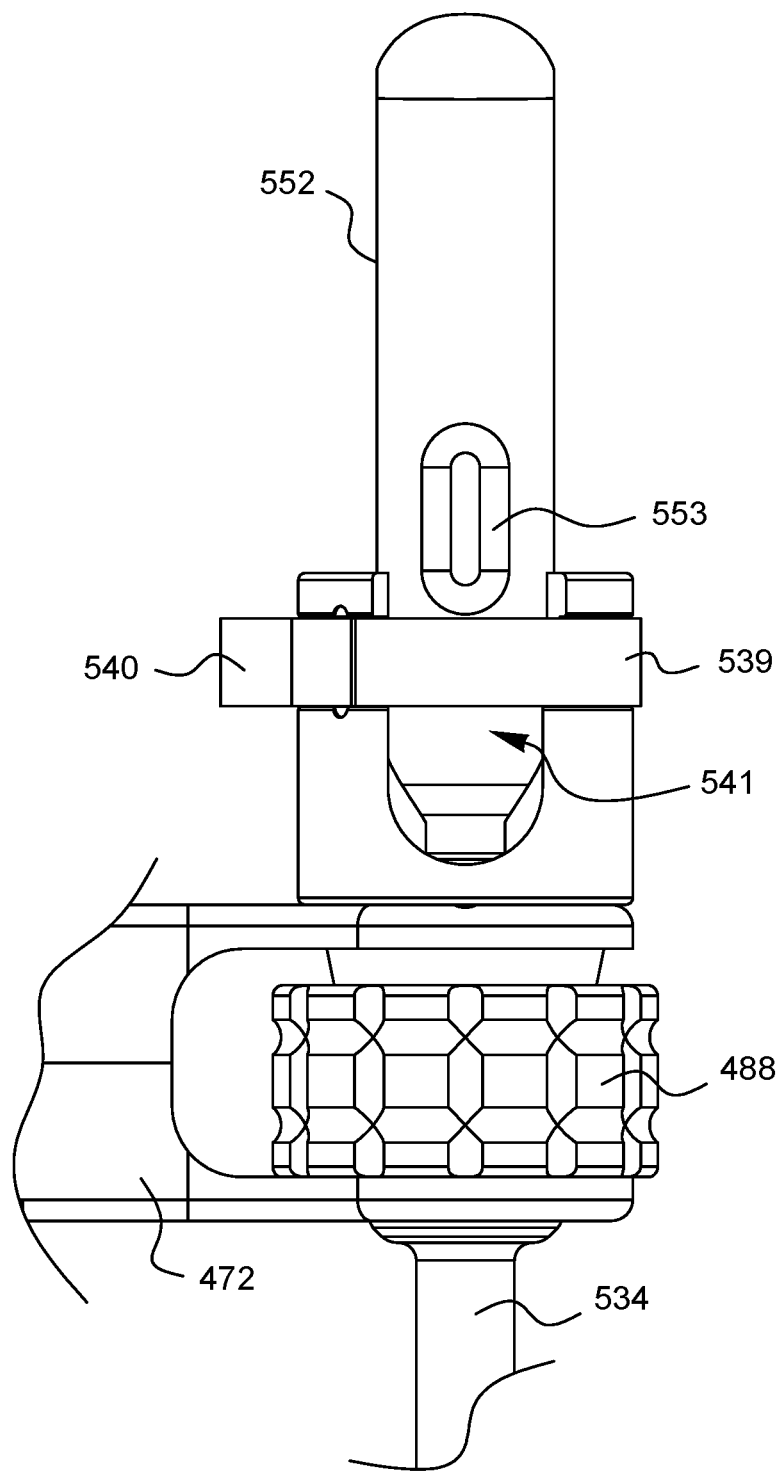

FIG. 25 is a side view of the top of the obturator of FIG. 24B inserted into the cannula and instrument adapter of FIG. 23.

Figure 26:
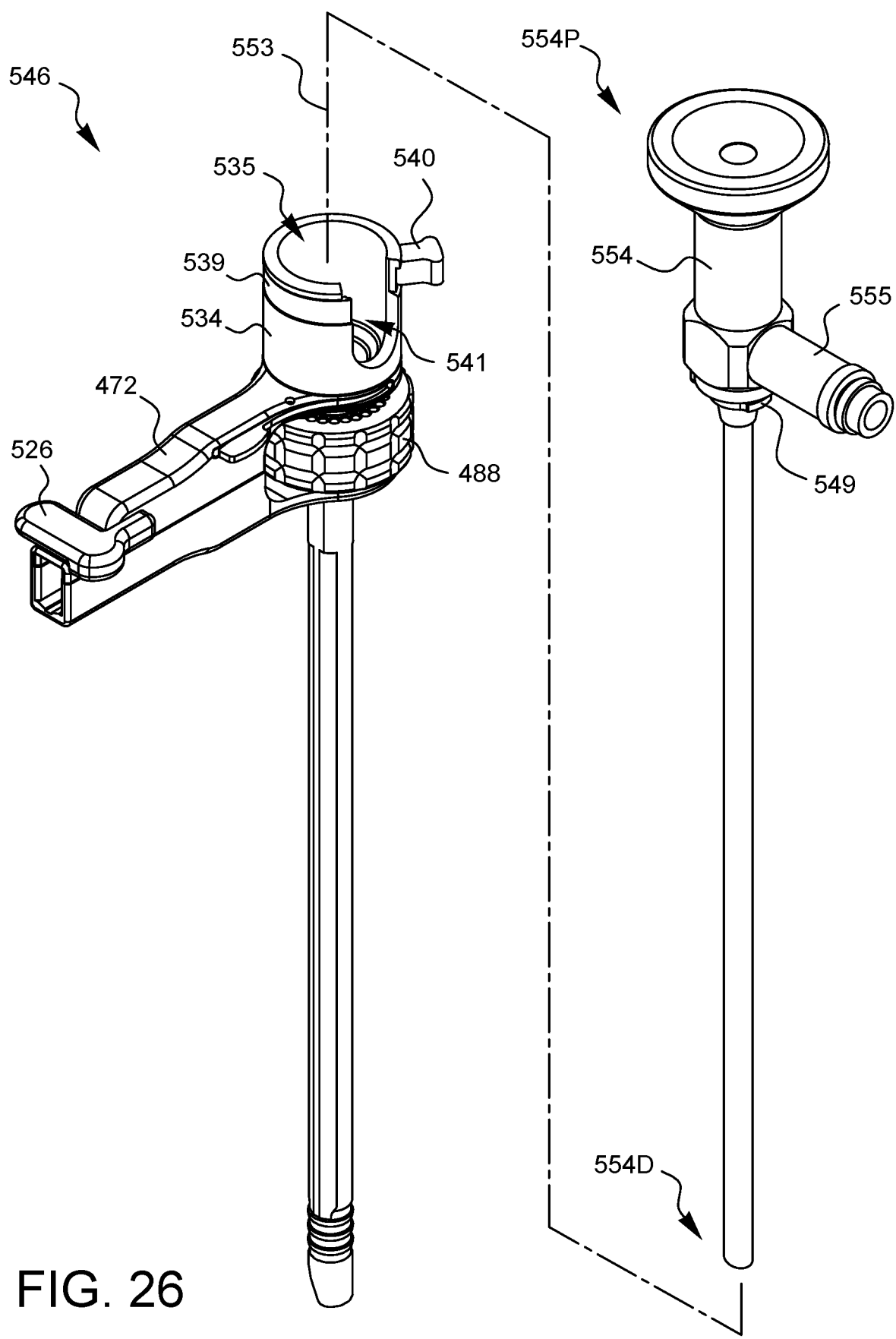

FIG. 26 is a perspective view detailing the insertion of an endoscope into the cannula and instrument adapter of FIG. 23.

Figure 27:
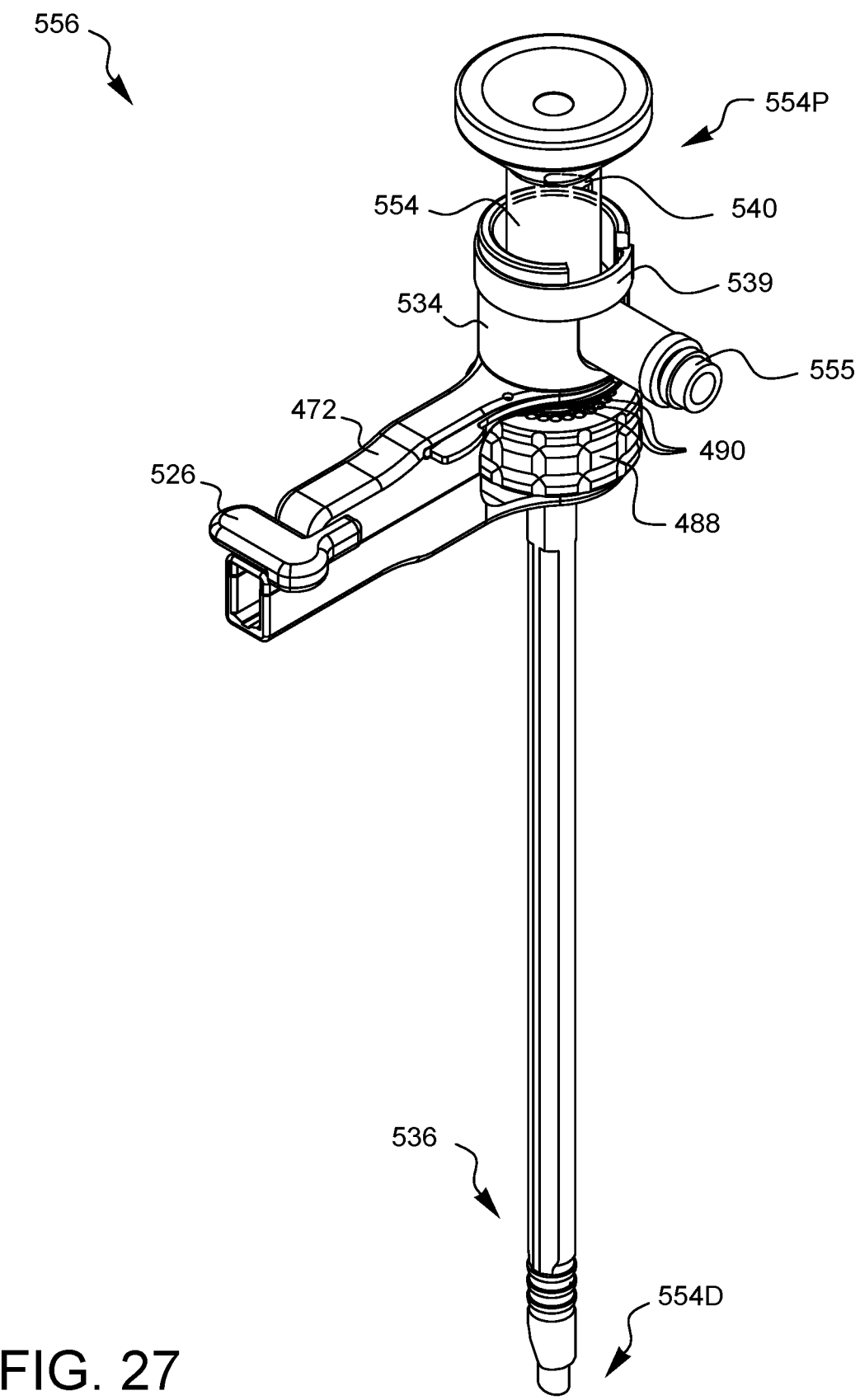

FIG. 27 is perspective view an endoscope inserted and locked into the cannula and instrument adapter of FIG. 23.

Figure 28A:
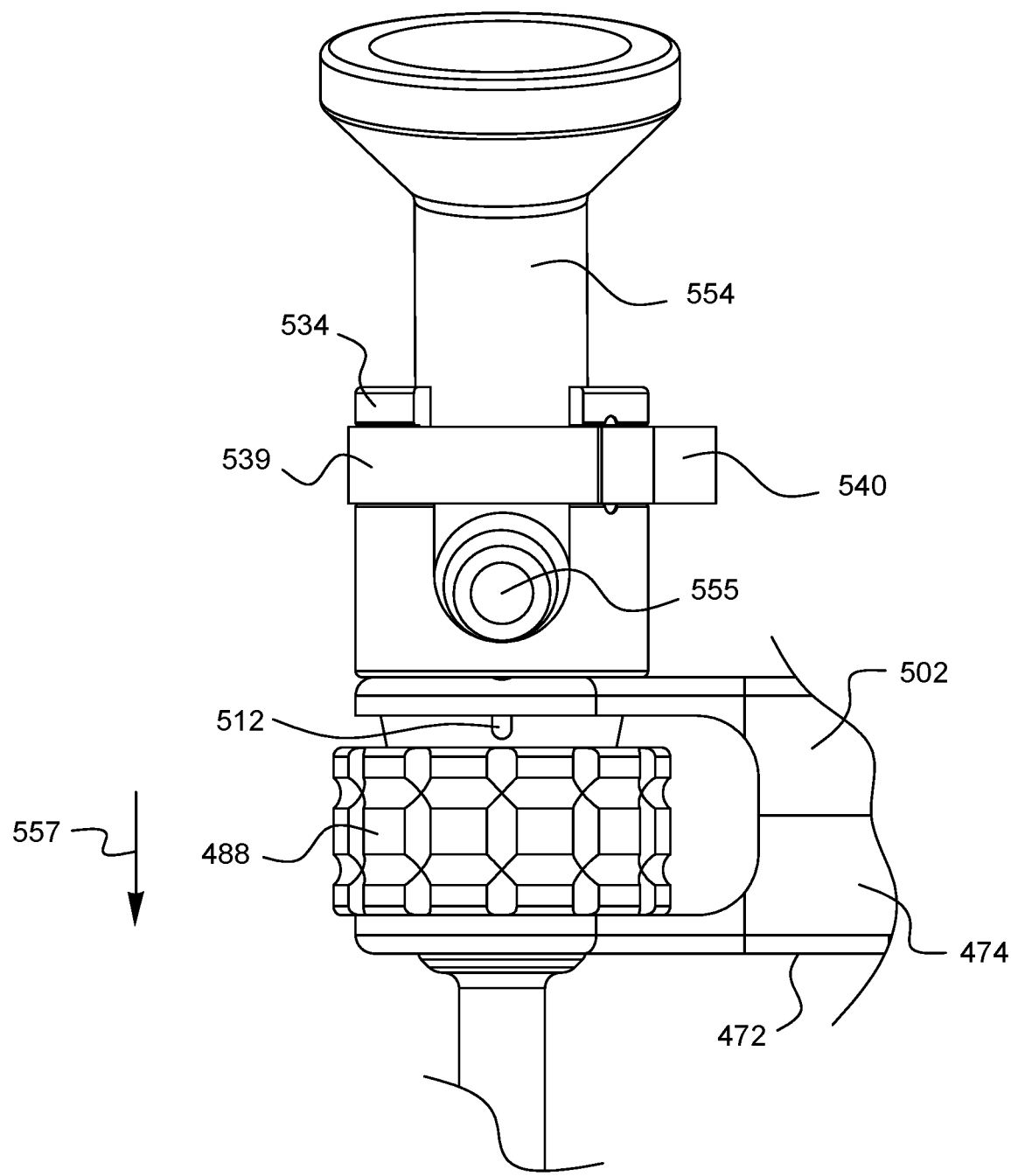
Figure 28B:
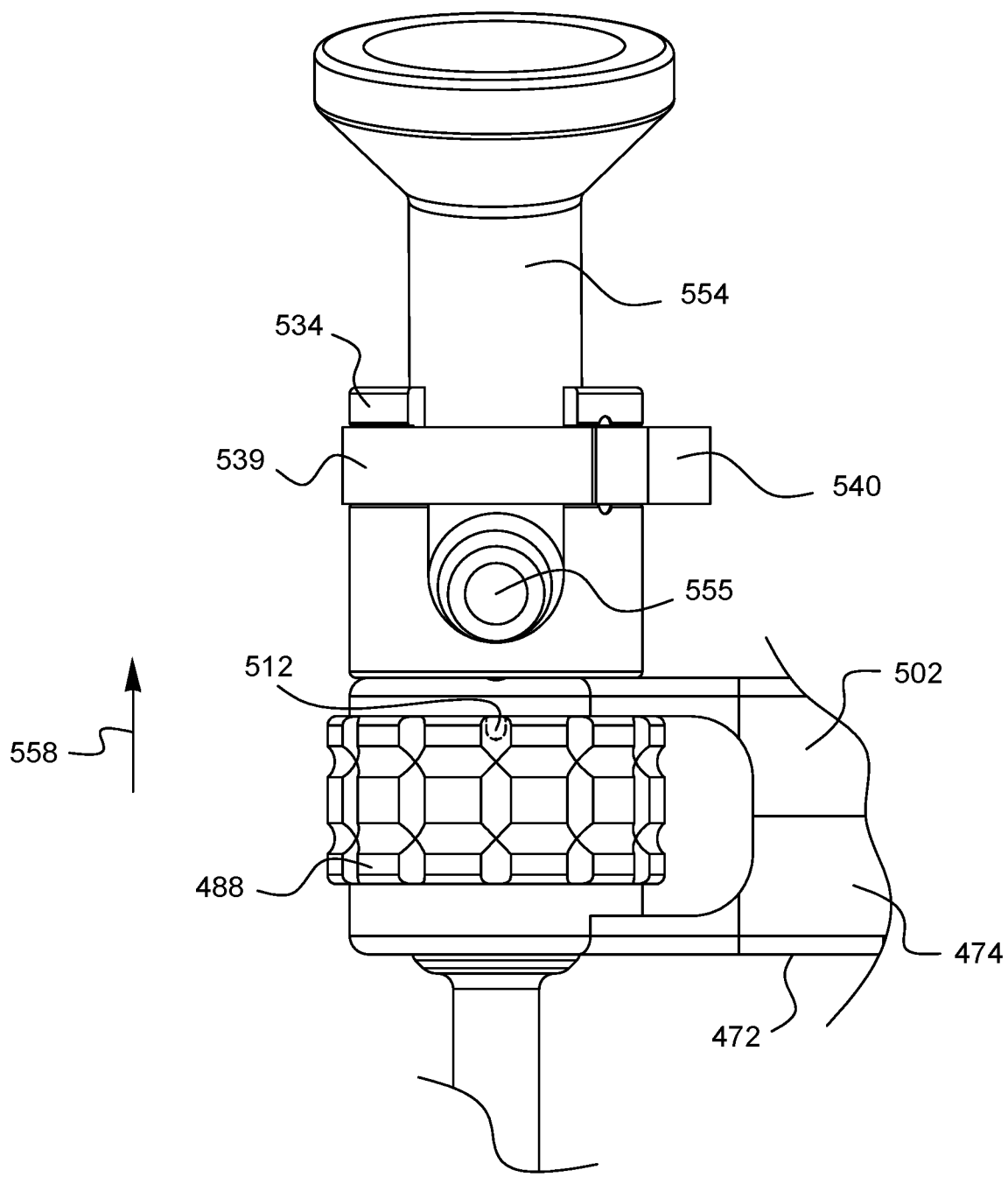

FIGS. 28A-28B are perspective views detailing the rotational dial function of the instrument adapter and endoscope of FIG. 27.

Figure 29:
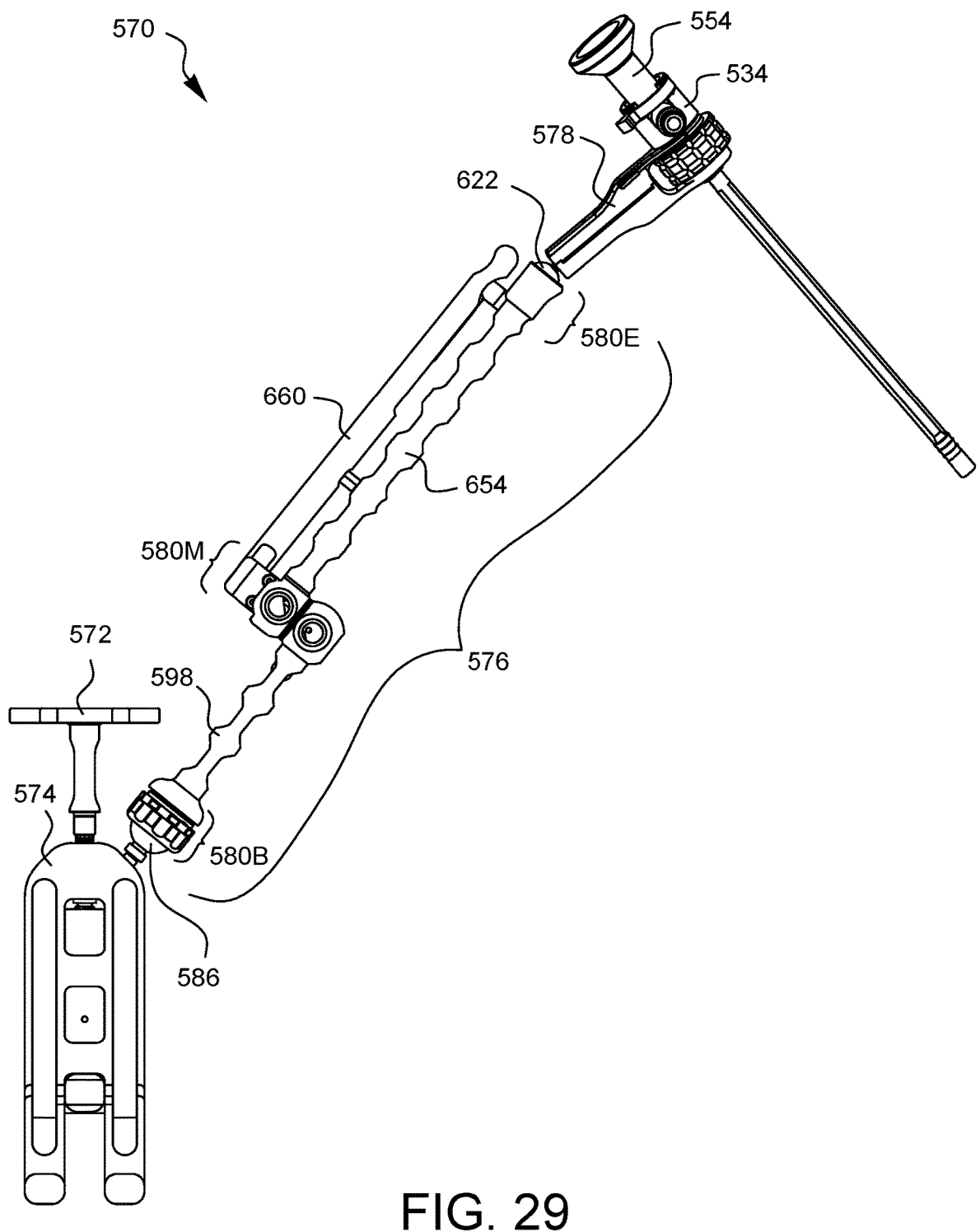

FIG. 29 is a side view of a further improved embodiment of a surgical equipment holder, also shown holding an endoscope.

FIGS. 30A-30E are a series of exploded perspective views showing the assembly of the adjustable arms for the surgical equipment holder of FIG. 29.

Figure 30A:
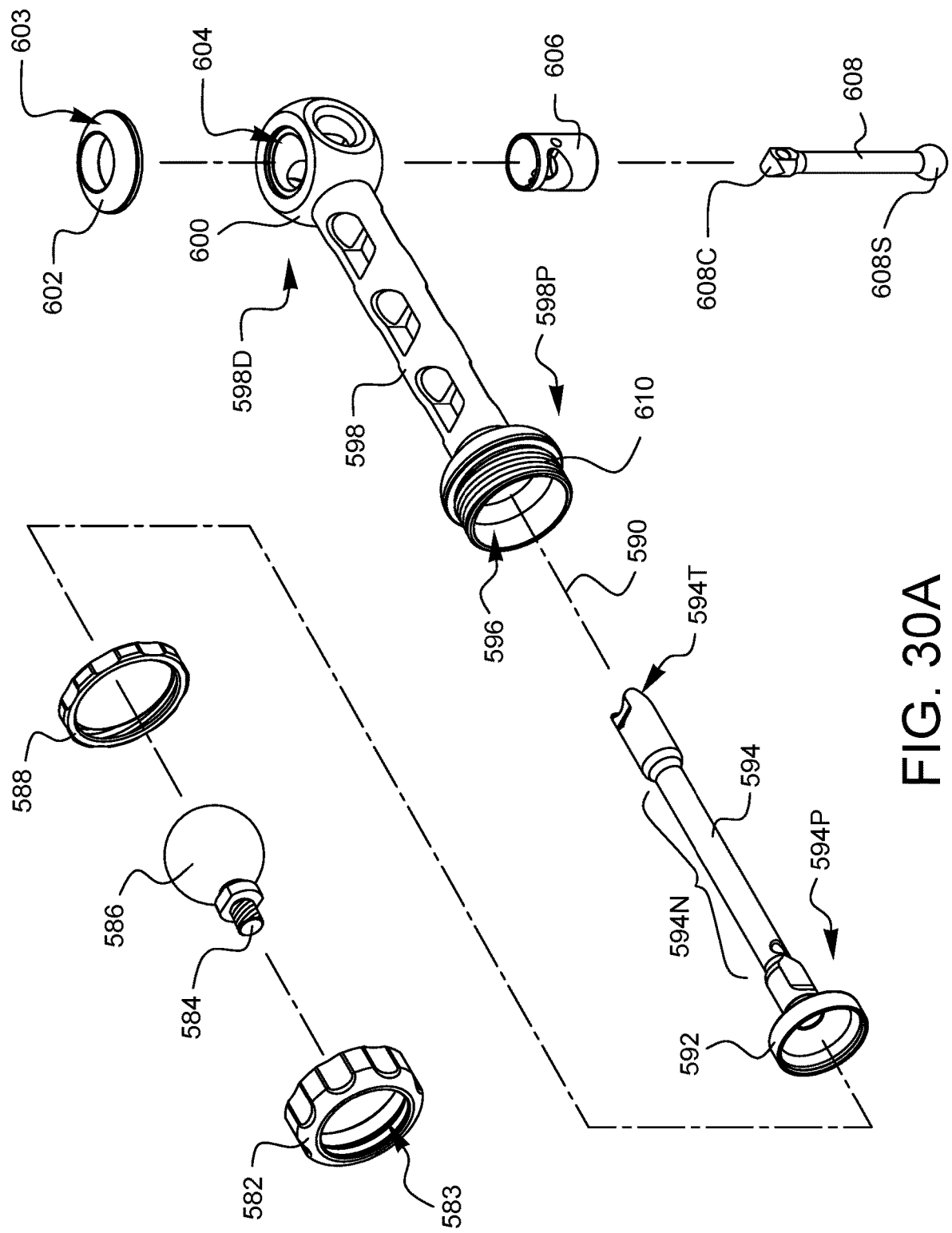
Figure 30B:
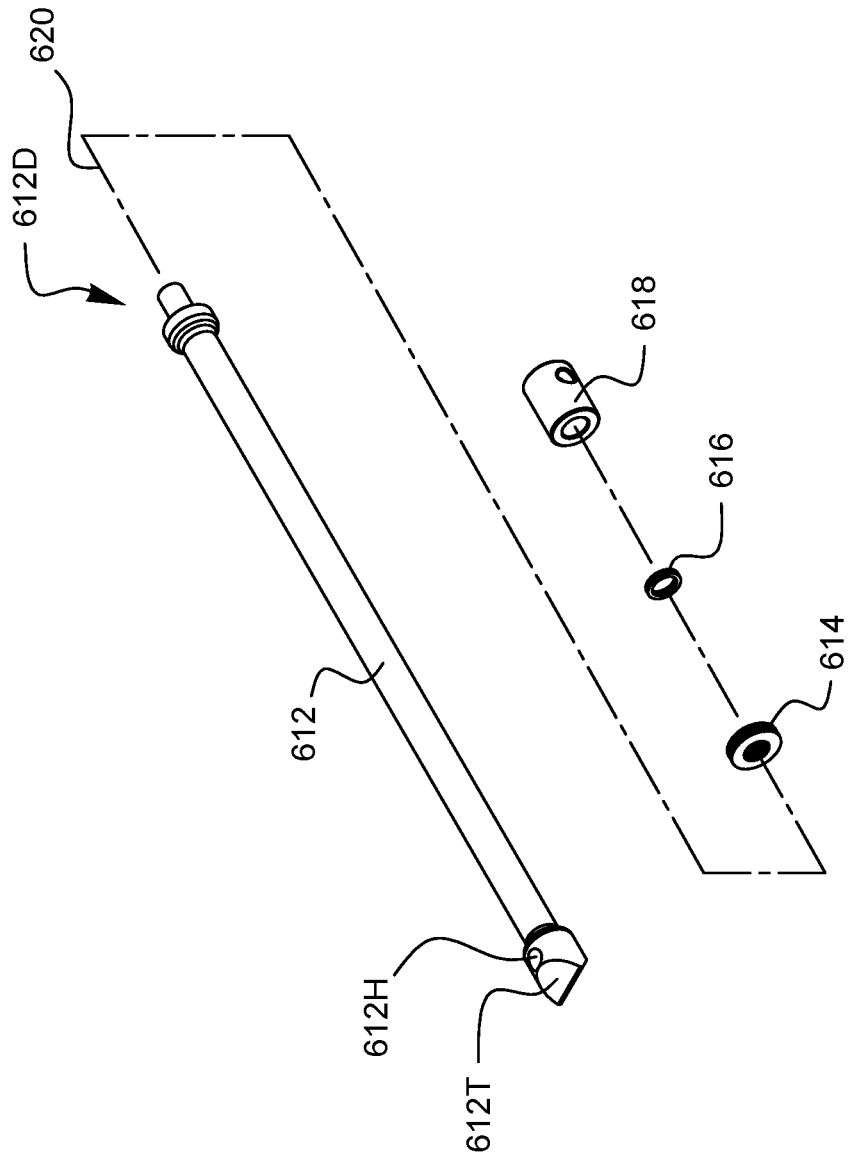
Figure 30C:
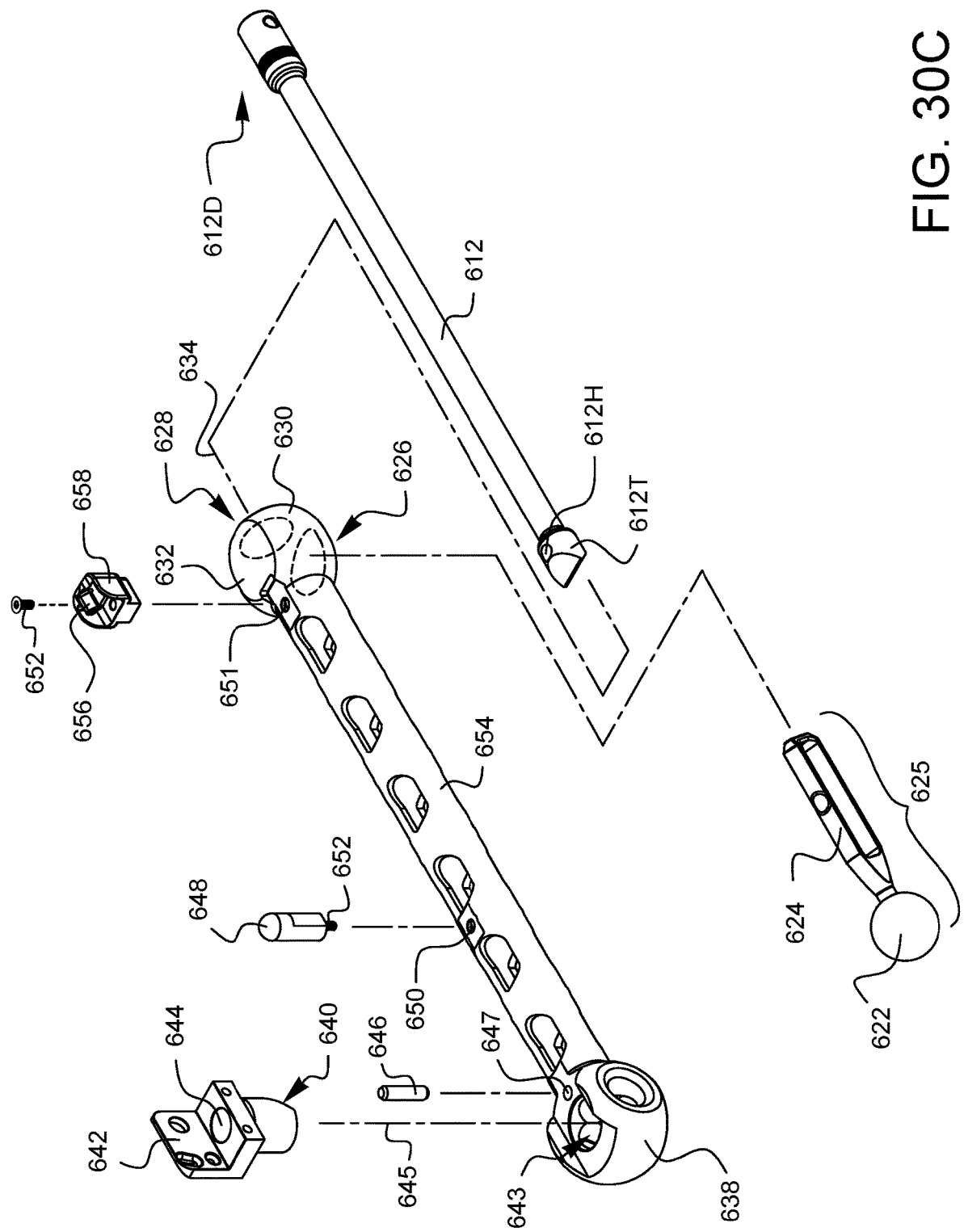
Figure 30D:
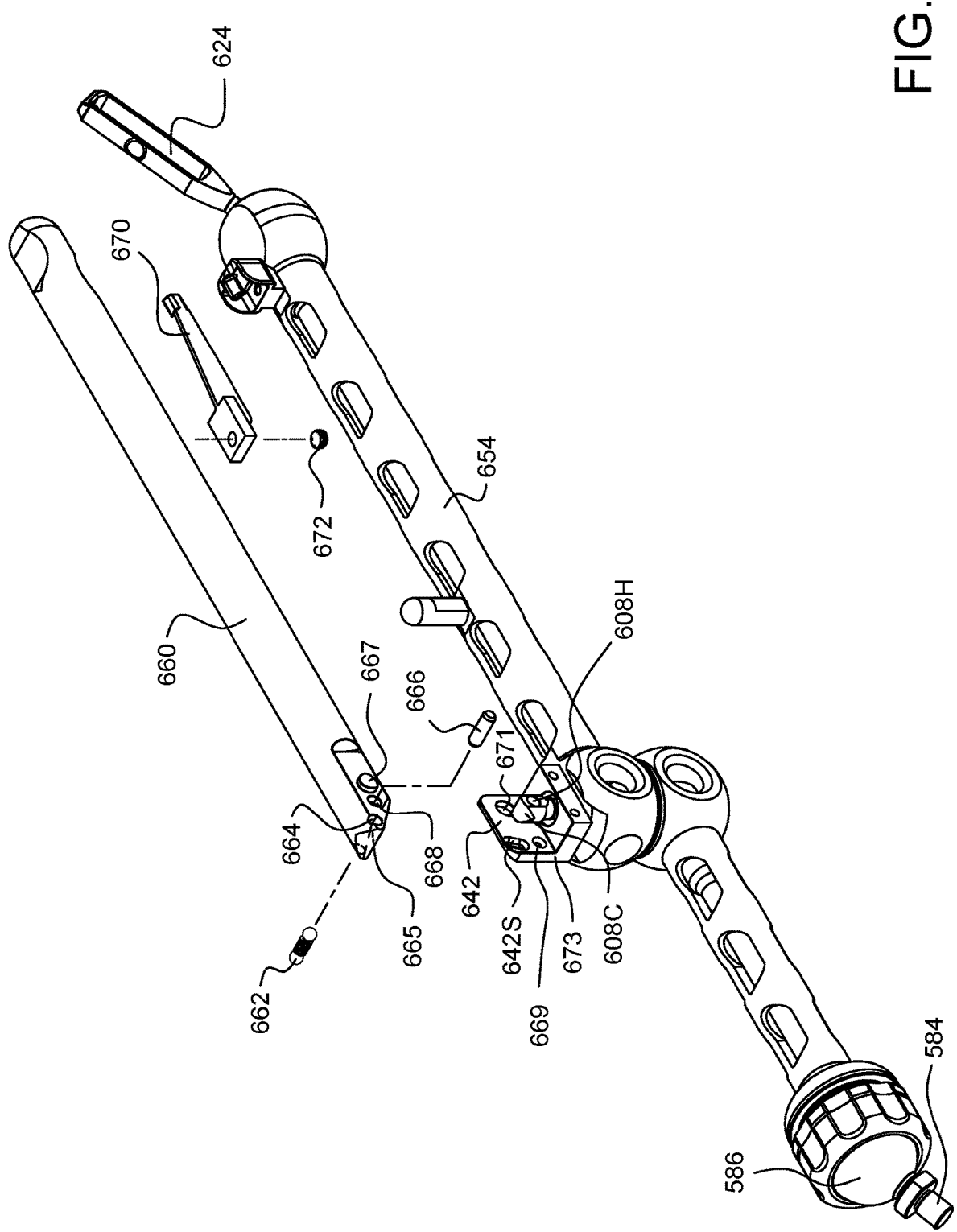
Figure 30E:
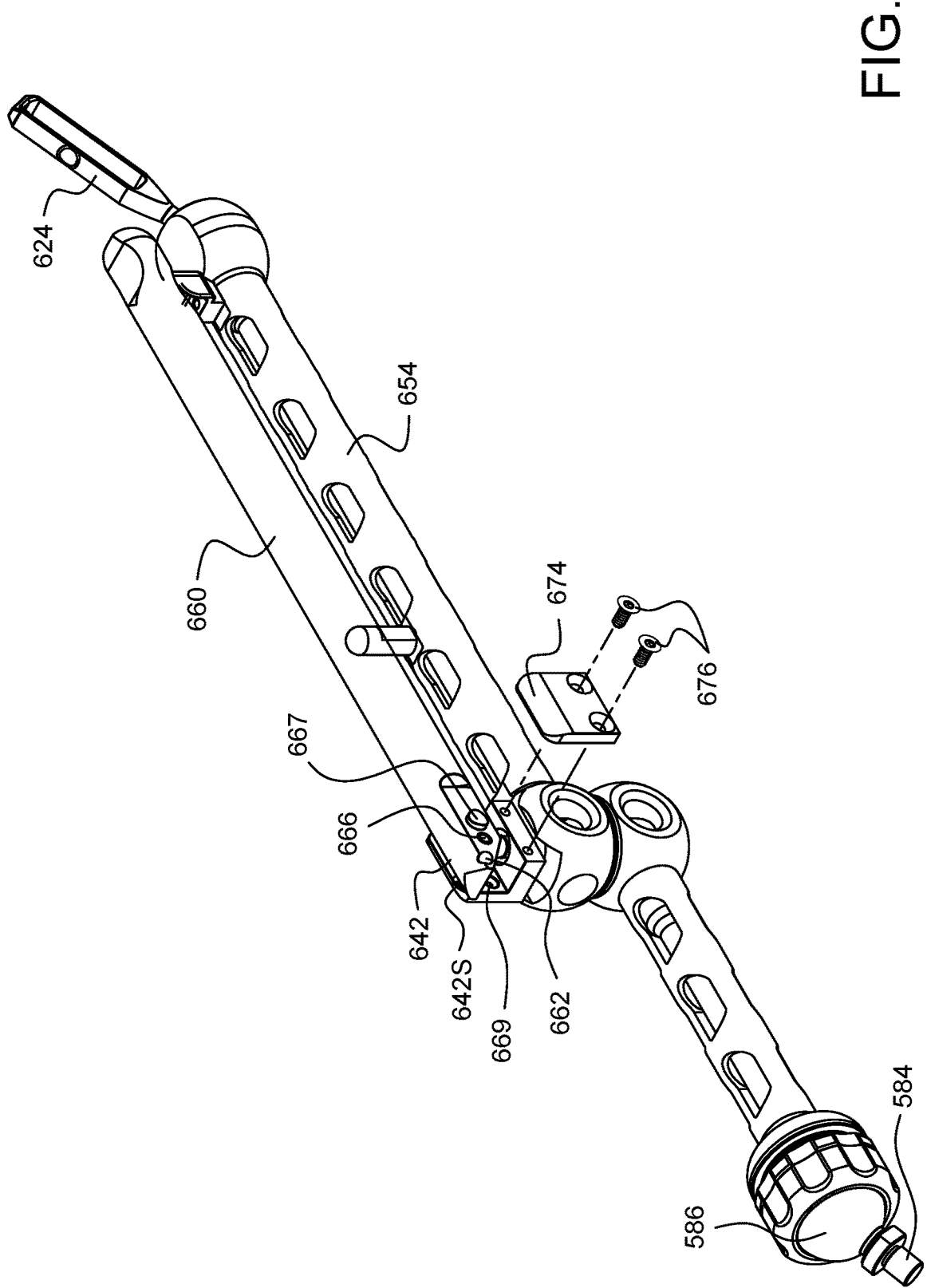
Figure 30F:
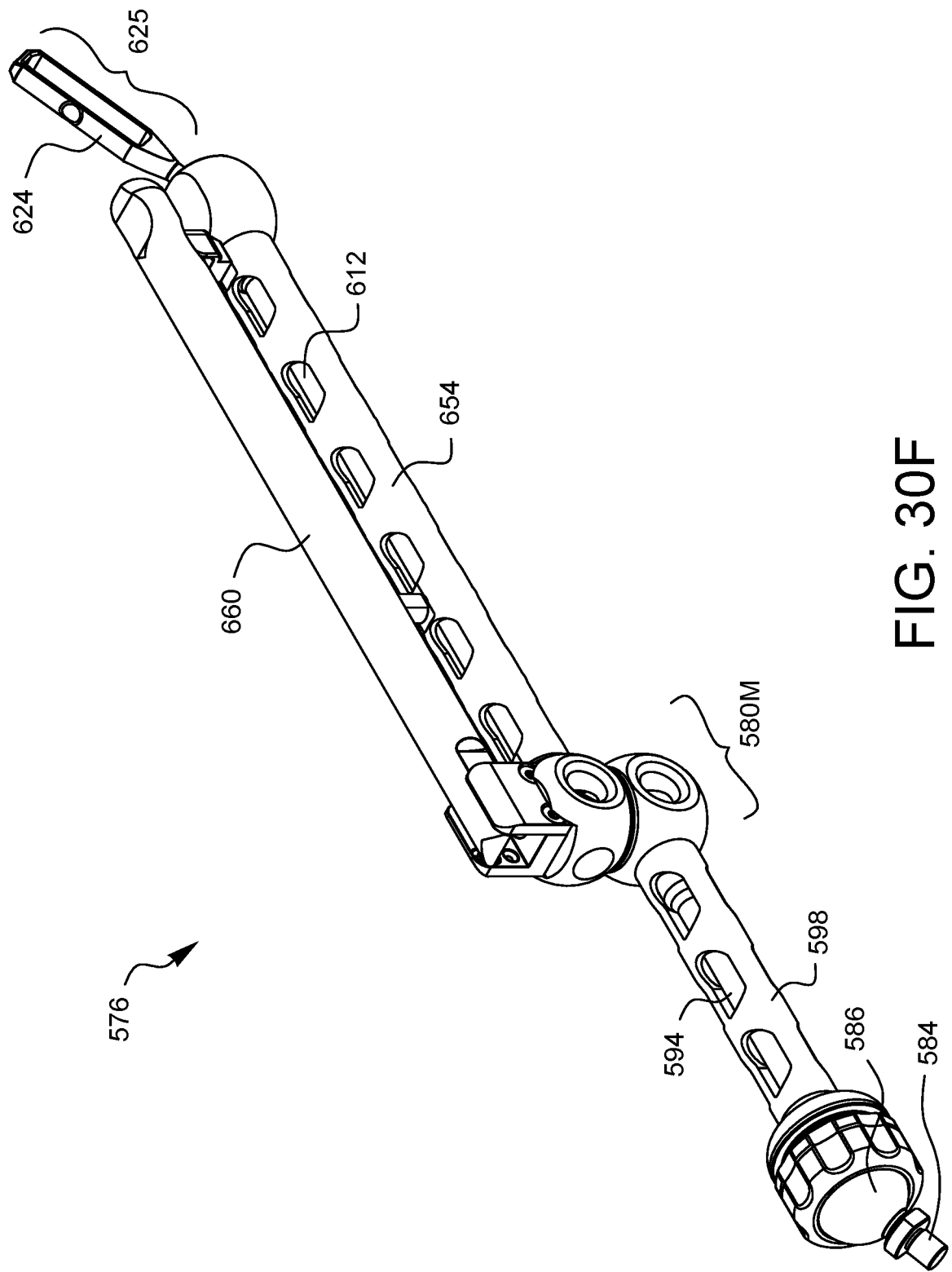

FIG. 30F is a perspective view of the adjustable arms of the surgical equipment holder of FIG. 29.

Figure 31A:
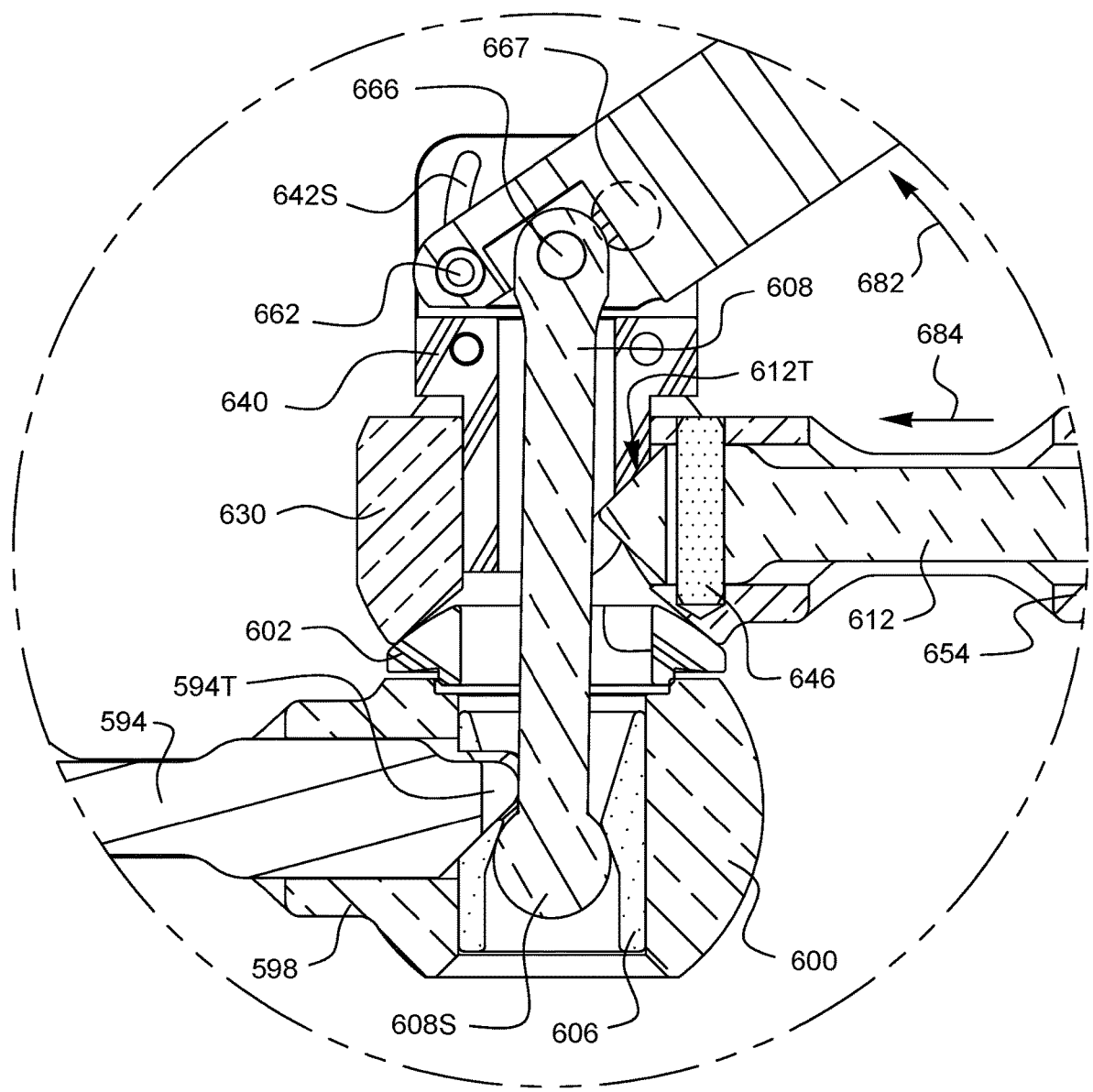
Figure 31B:
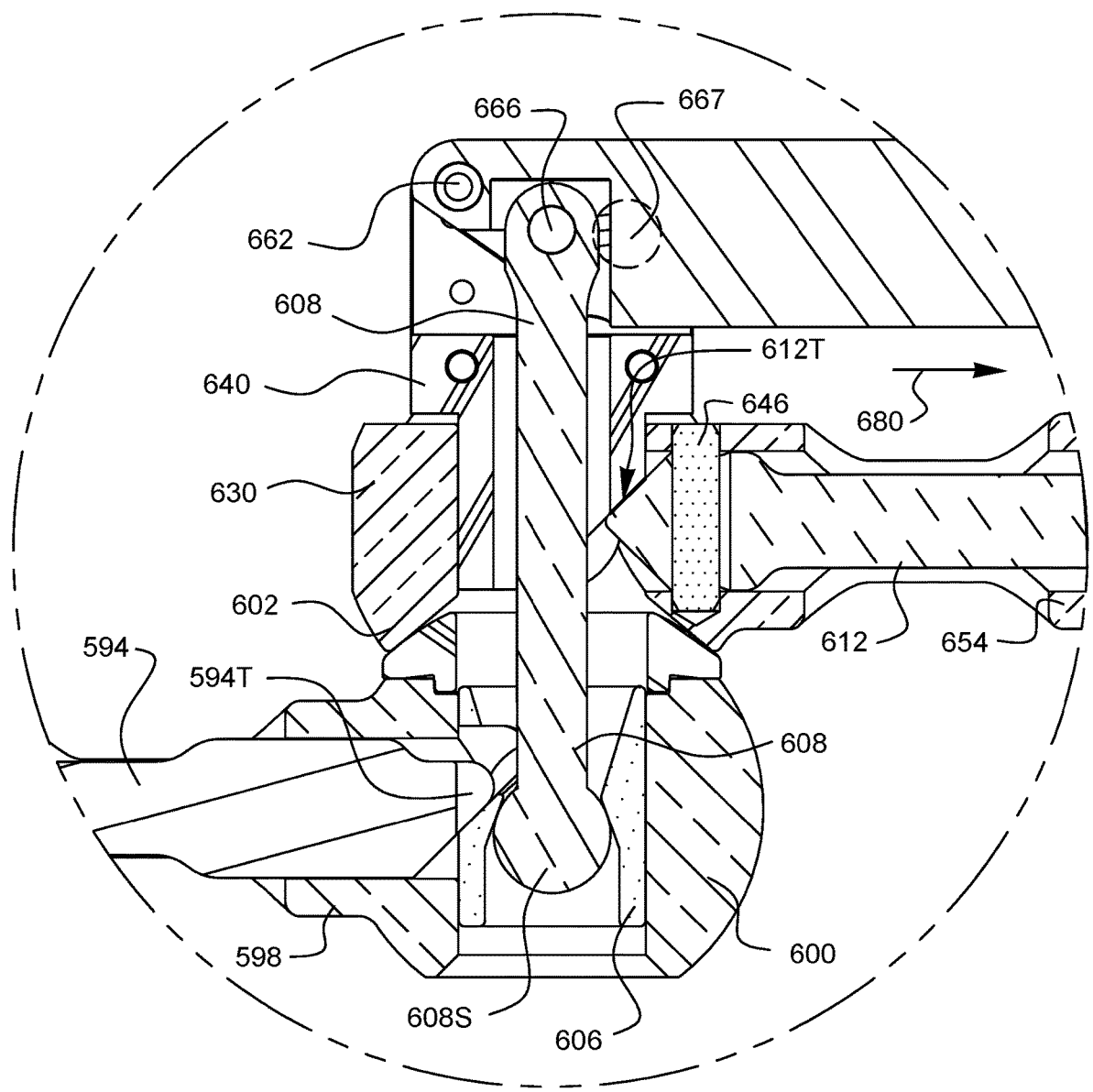

FIGS. 31A-31B are enlarged side cross-sectional views of a portion of a middle joint interface between the first and second arms of the surgical equipment holder of FIG. 29 in an unlocked and locked state, respectively.

Figure 32A:
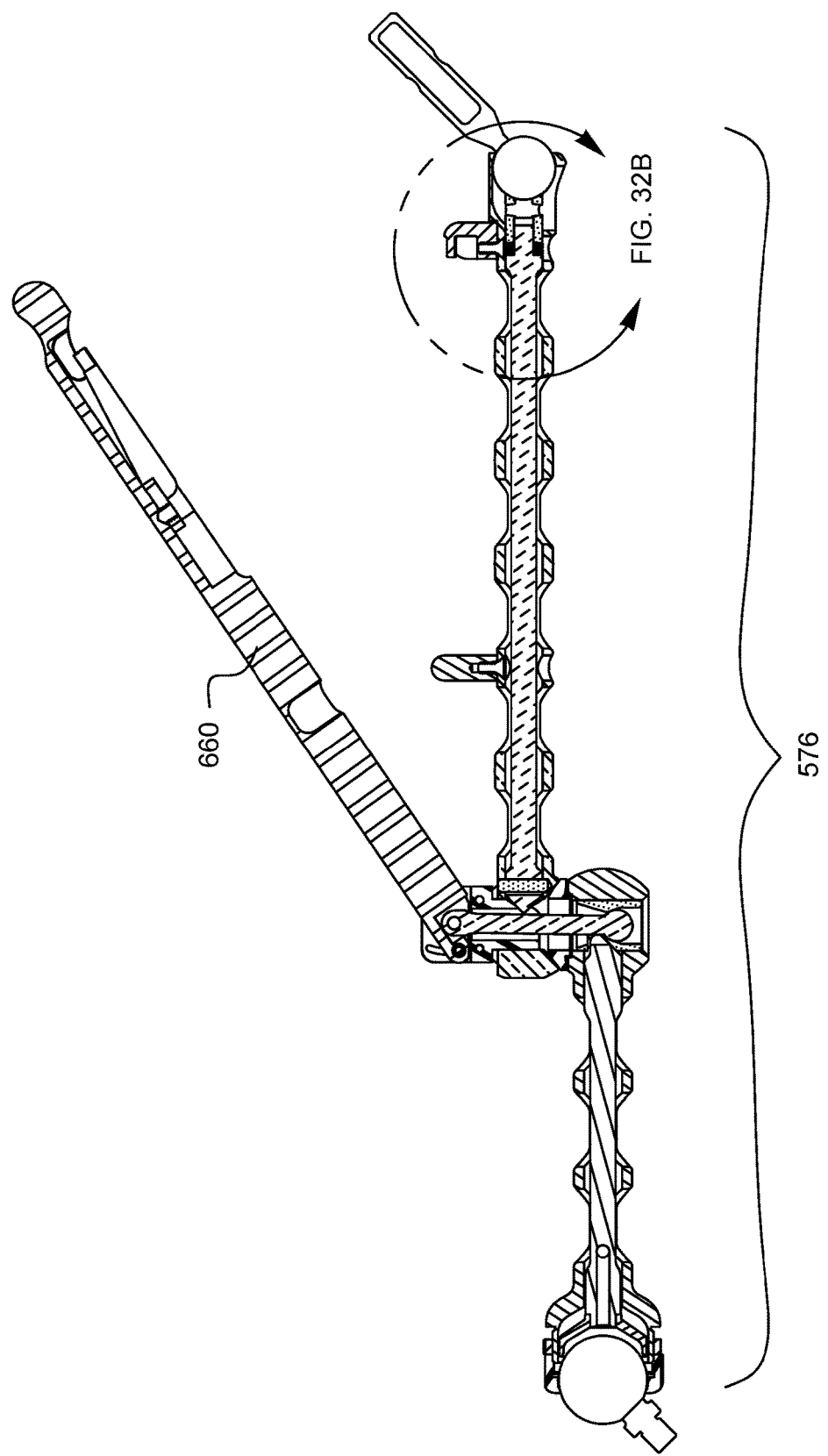

FIG. 32A is a side view of a partial cross-sectional view of the surgical equipment holder of FIG. 29, not including the base, in an unlocked position.

Figure 32B:
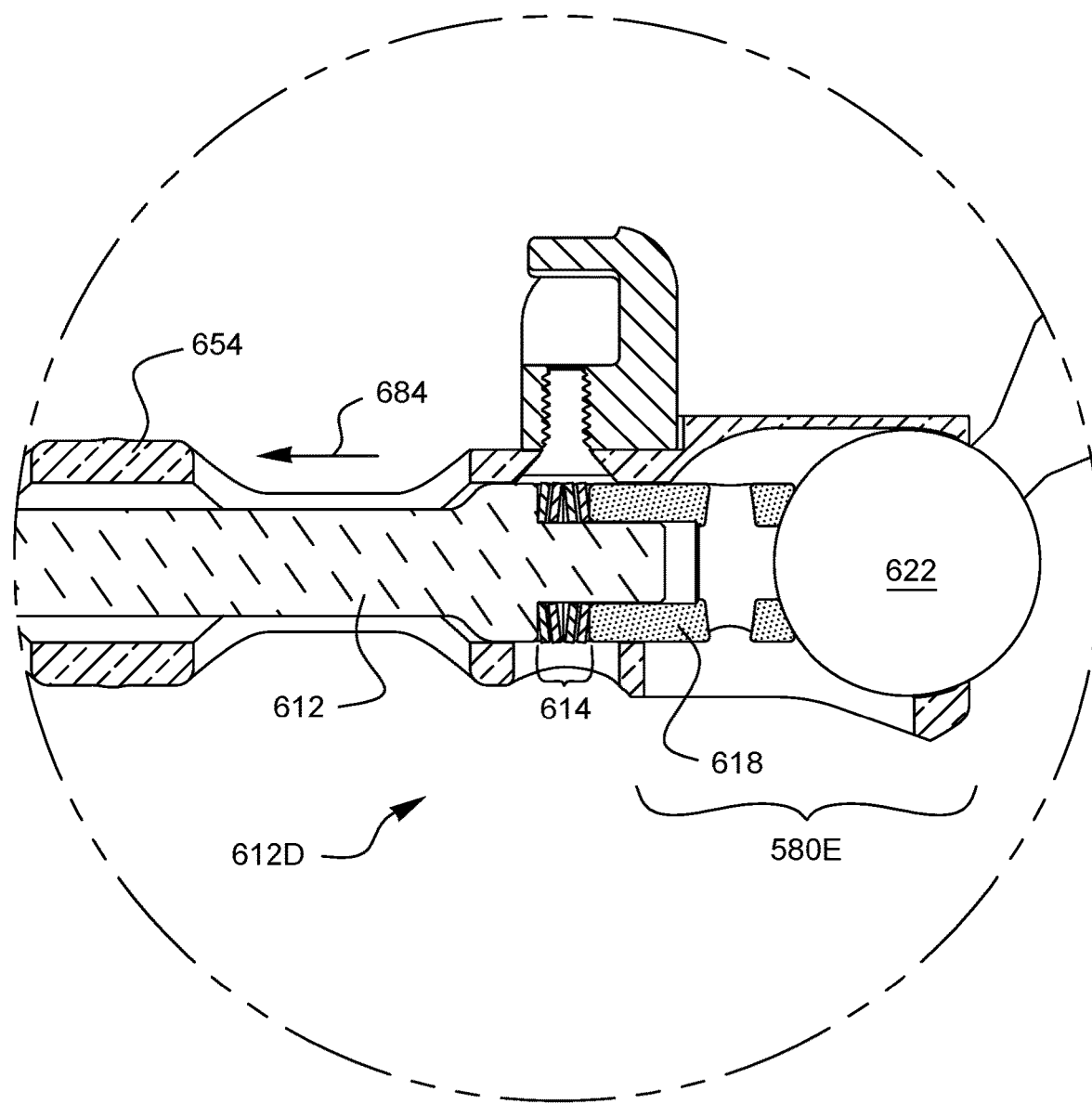

FIG. 32B is an enlarged side view of a partial cross-sectional view of a portion of a base joint interface between the second arm and a ball on a quick connect post of the surgical equipment holder of FIG. 29 in an unlocked state.

Figures 33A, 33B:
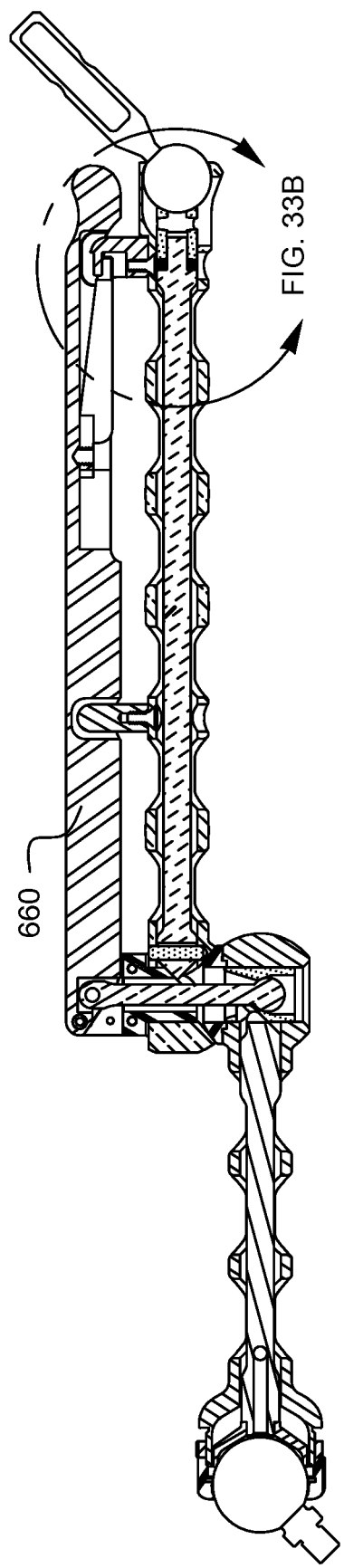
Figure 33B:
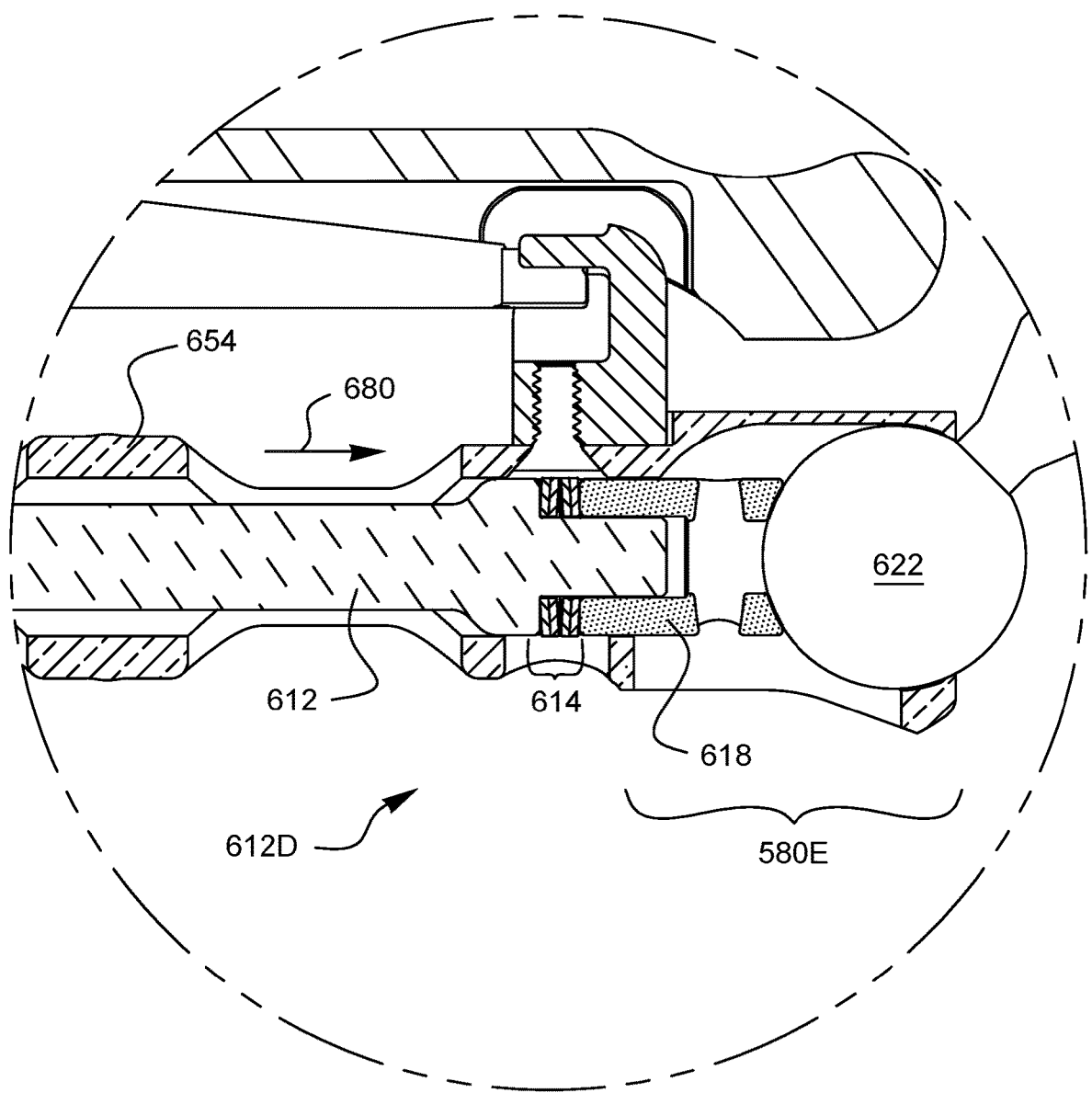

FIG. 33A is a side view of a partial cross-sectional view of the surgical equipment holder of FIG. 29, not including the base, in a locked position.

FIG. 33B is an enlarged side view of a partial cross-sectional view of a portion of a base joint interface between the second arm and a ball on a quick connect post of the surgical equipment holder of FIG. 29 in a locked state.

Figure 34:
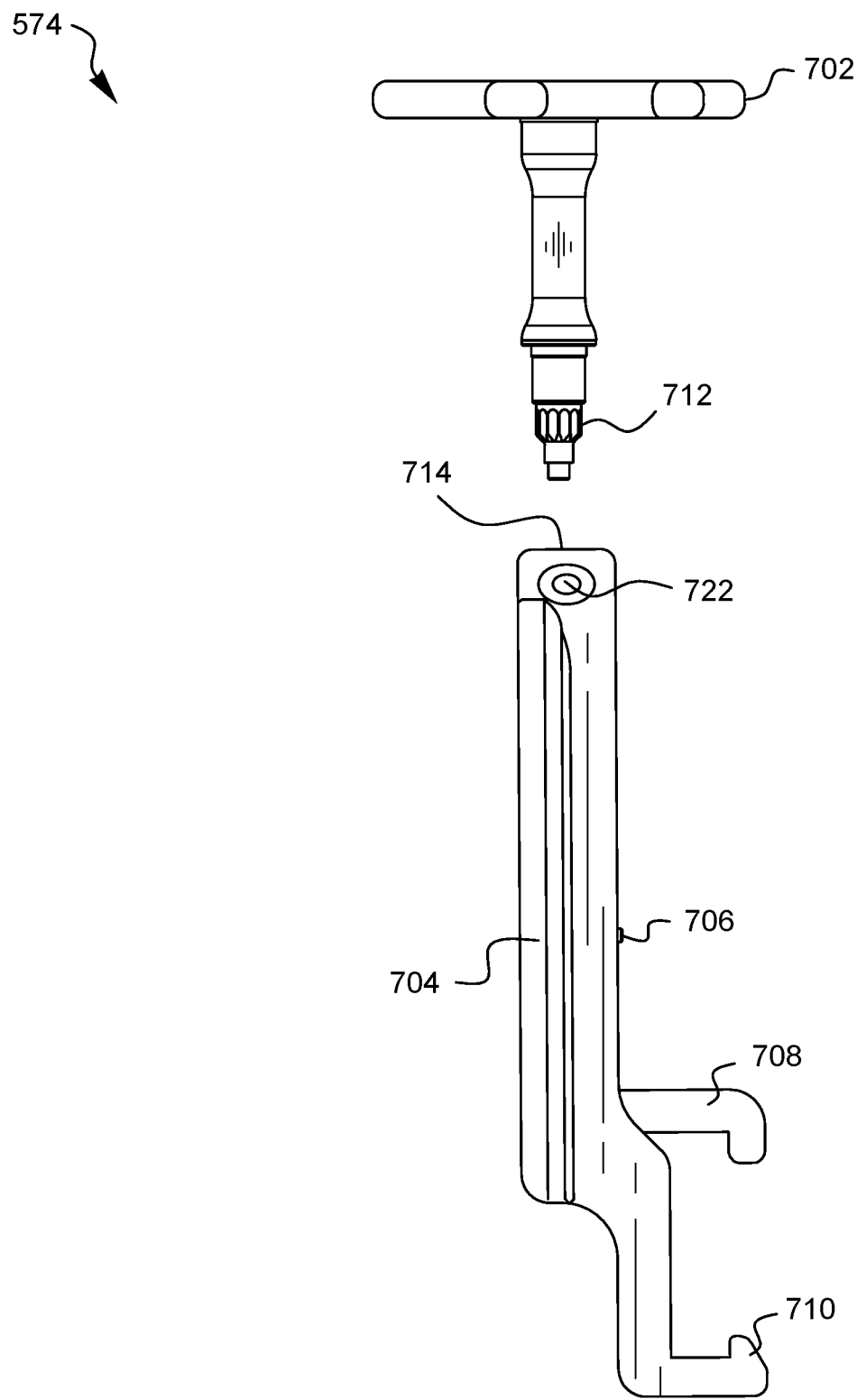

FIG. 34 is a right side view of an embodiment of a base for use with the surgical equipment holders of FIG. 4, FIG. 8, FIG. 14, FIG. 18, and FIG. 29.

FIG. 35A-F show front, right side, left side, rear, top, and bottom views, respectively, of the base of FIG. 34.

Figure 36A:
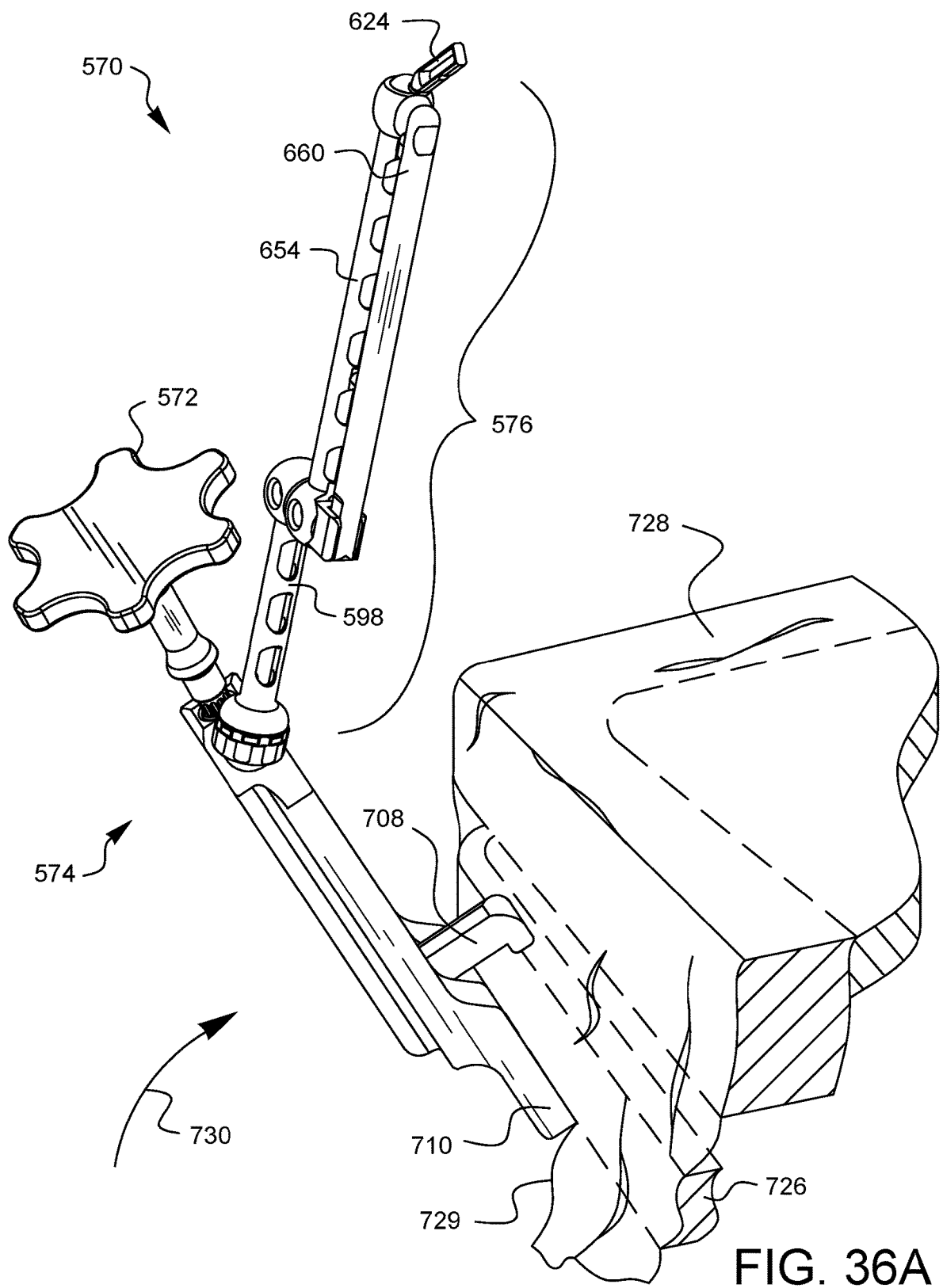
Figure 36B:
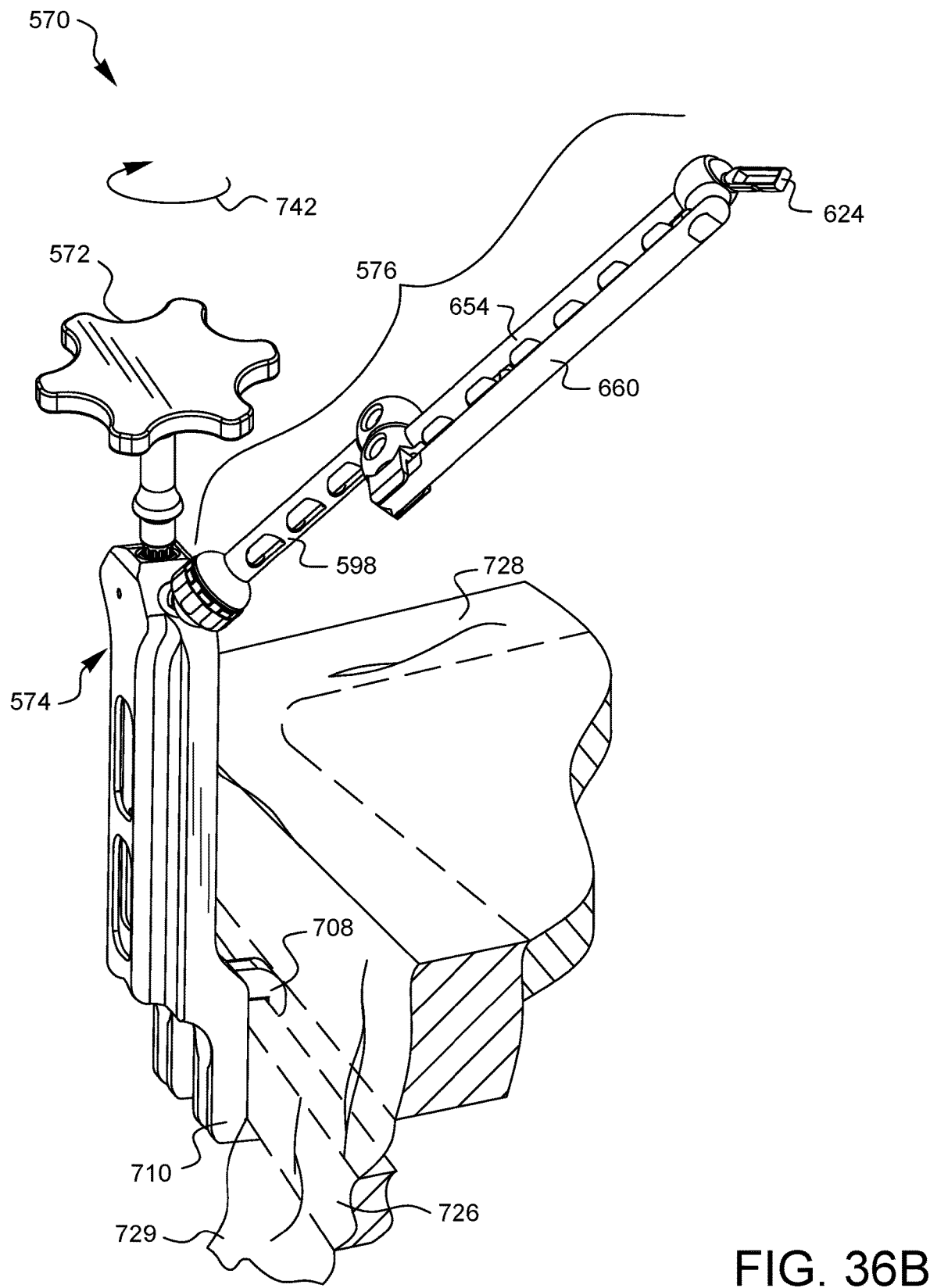

FIGS. 36A-36B are perspective views of the surgical equipment holder of FIG. 29 being attached to a surgical table.

Figure 37A:
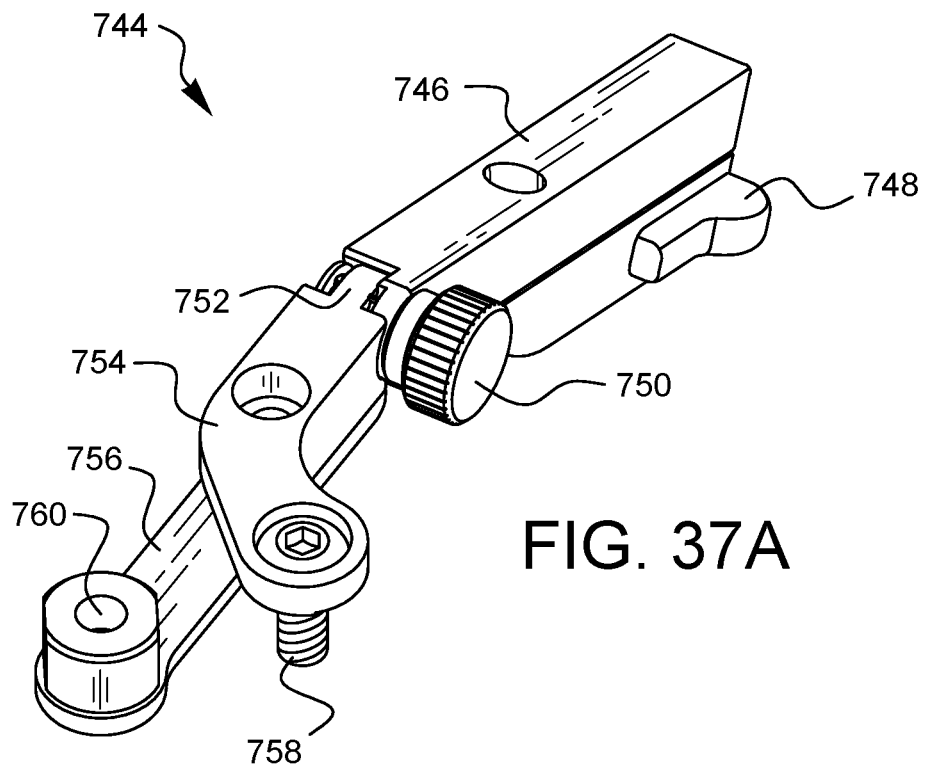
Figure 37B:
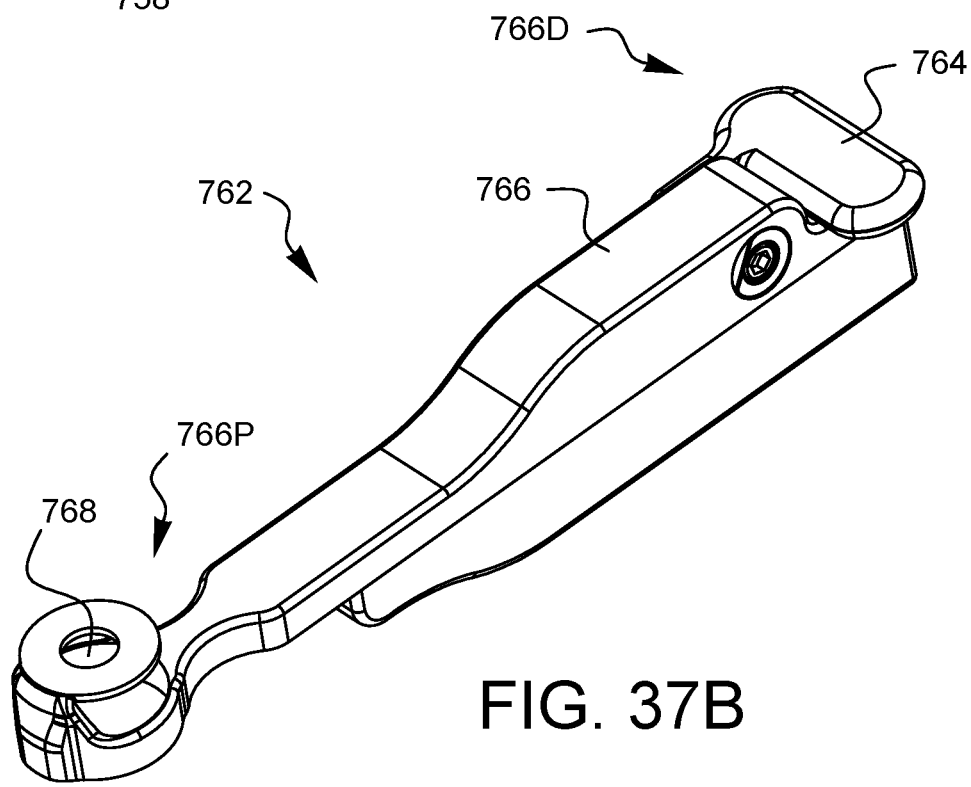

FIGS. 37A-37B are perspective views of other embodiments of instrument adapters for use with the surgical equipment holder of FIG. 29.

Figure 38:
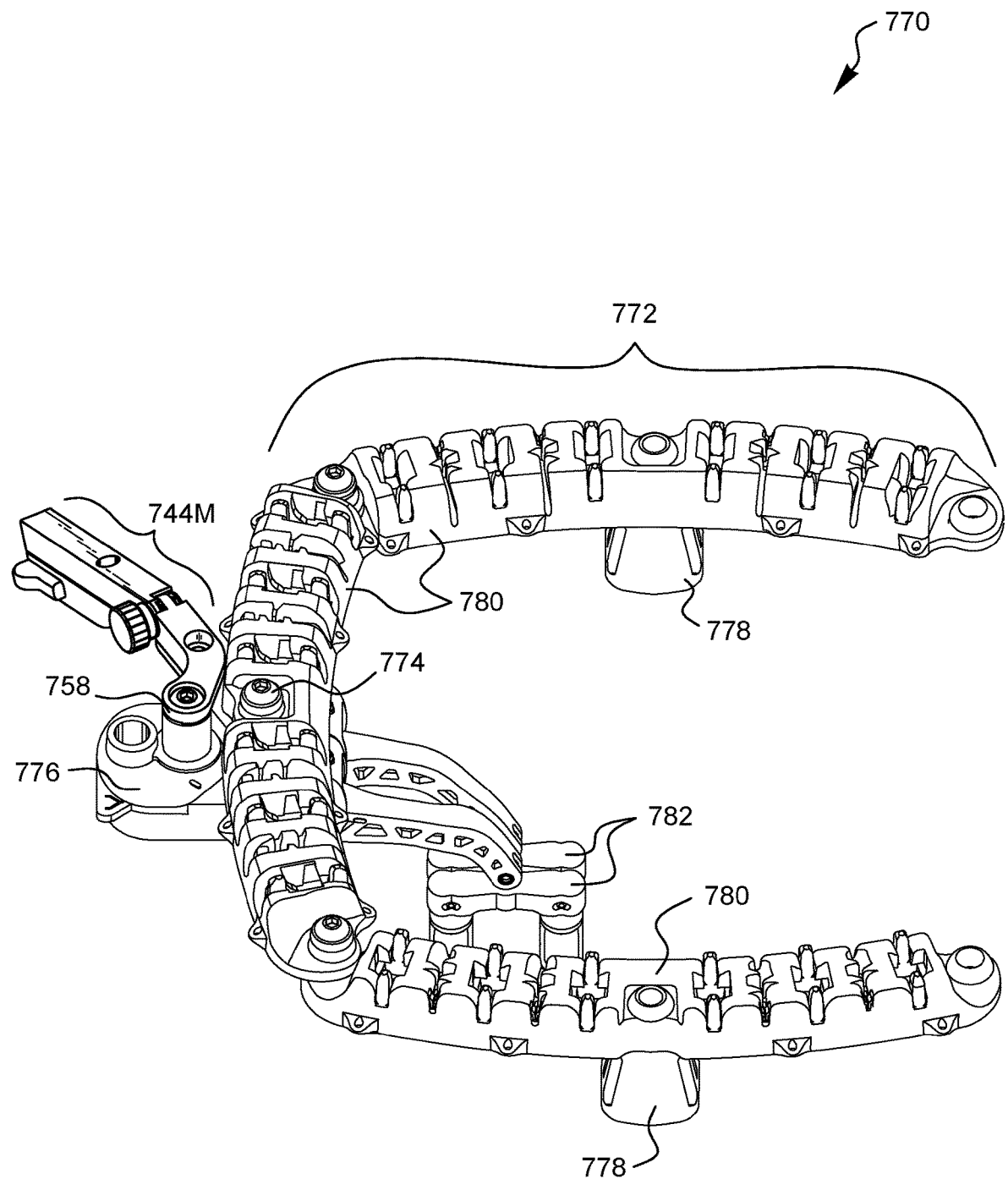

FIG. 38 is a perspective view of a suture management system and a rib retractor for use with the surgical equipment holder of FIG. 29.

Figure 39:
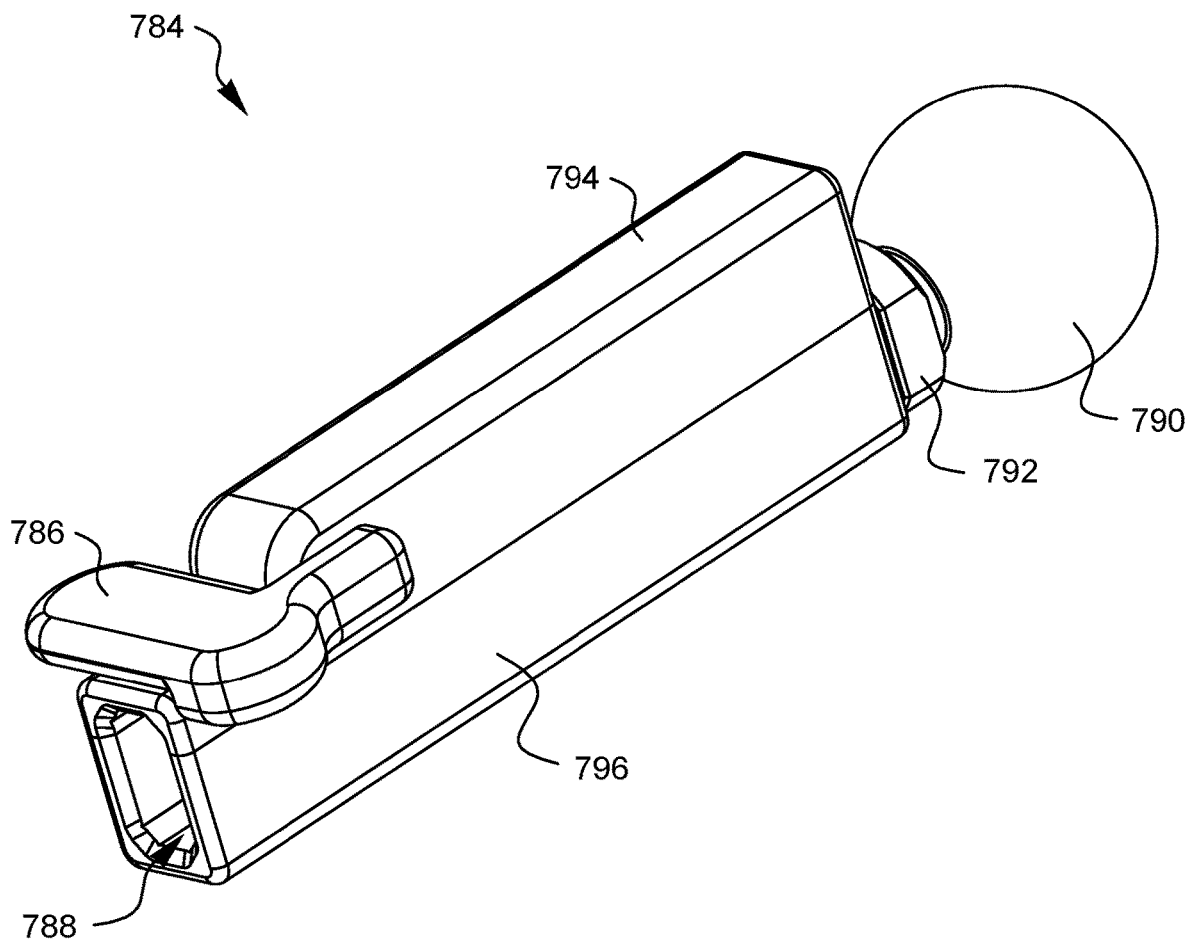

FIG. 39 is a perspective view of a display mount adapter for use with the surgical equipment holder of FIG. 29.

Figure 40A:
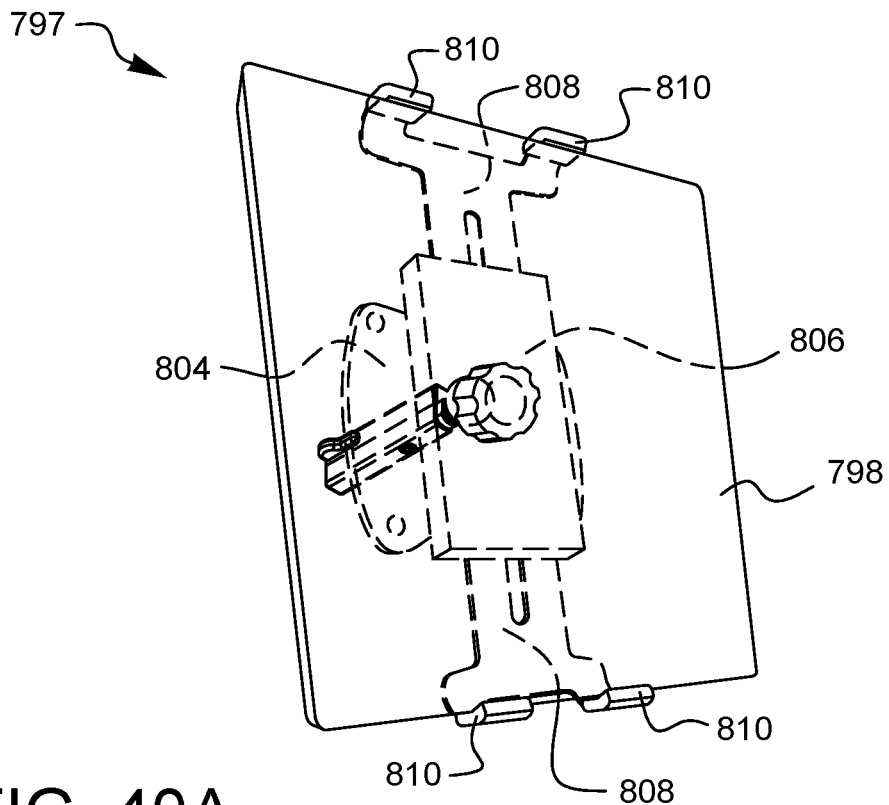
Figure 40B:
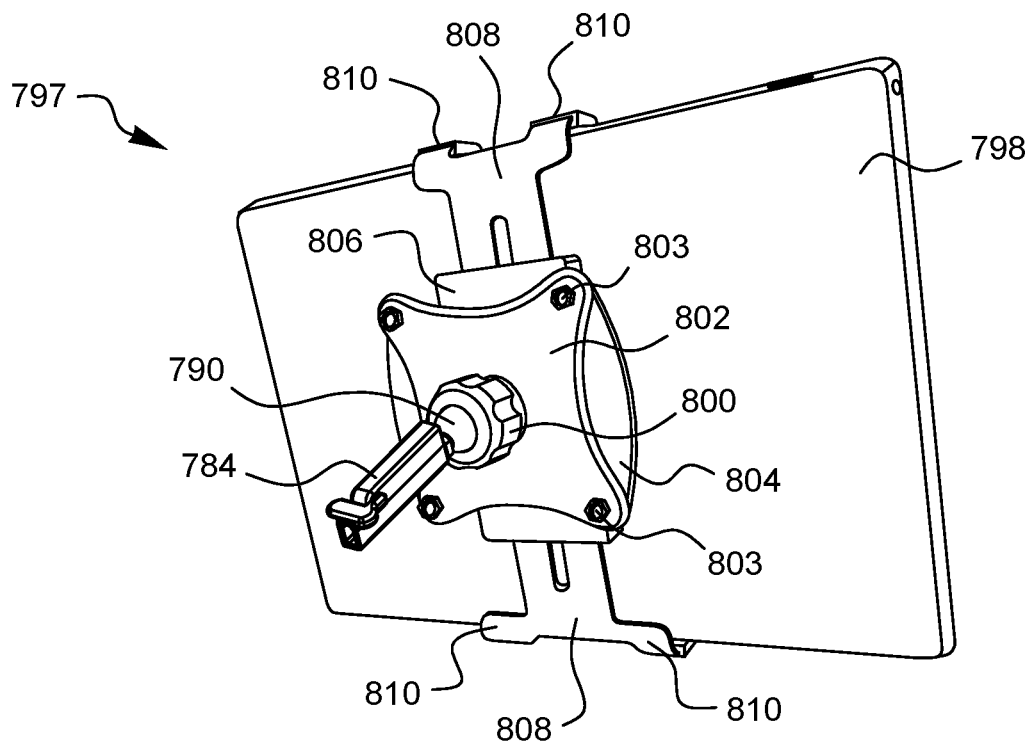

FIG. 40A-B are perspective views of a display attached to the display mount adapter of FIG. 39.

Figure 41:
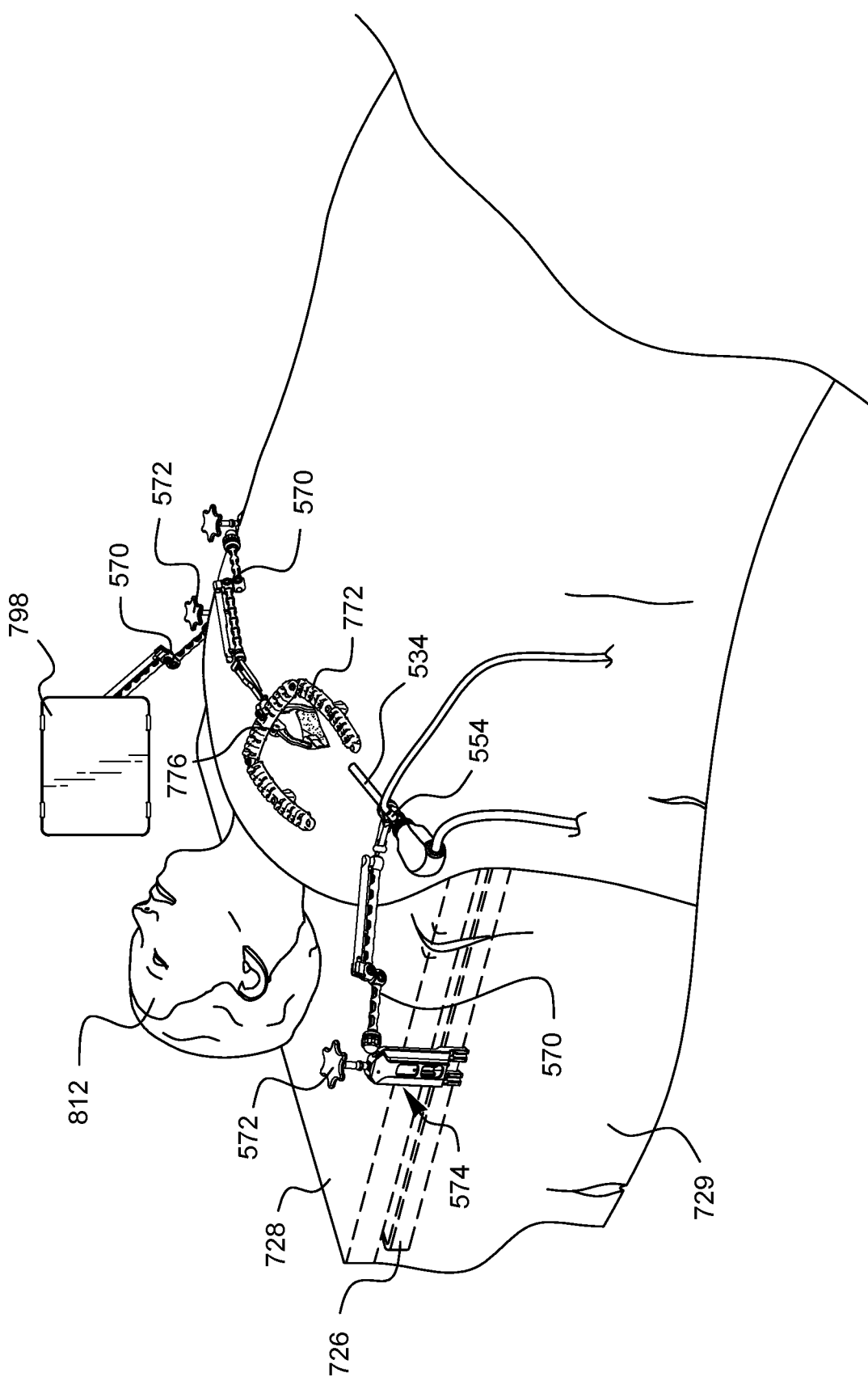

FIG. 41 is a perspective view of three surgical equipment holders of FIG. 29 attached to a surgical table with different adapters and equipment attached thereto.

DETAILED DESCRIPTION

Figure 1:
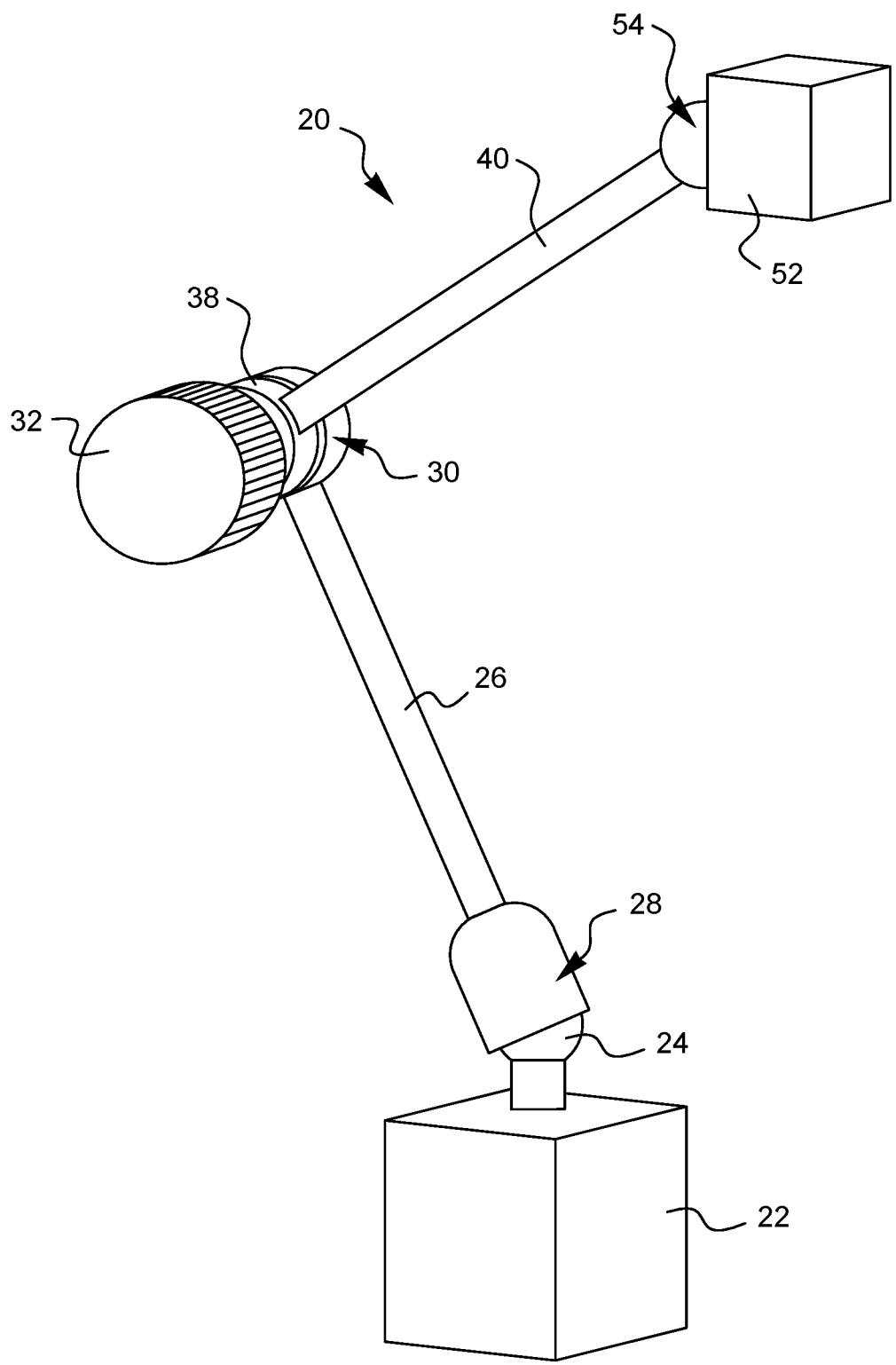
FIG. 1 is a schematic illustration of a prior art equipment holder.
Figure 2:
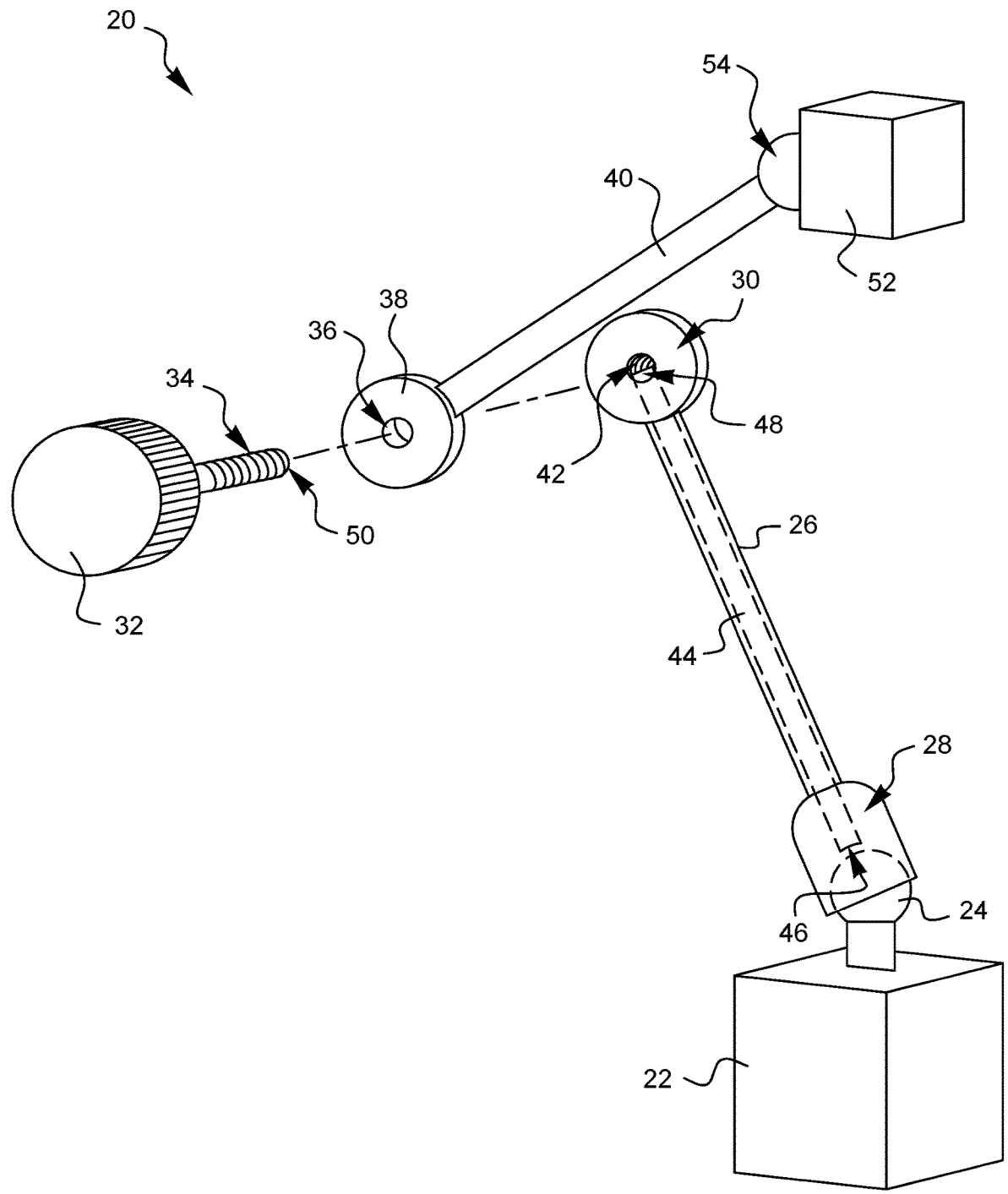
FIG. 2 is a partially exploded perspective view of the prior art equipment holder of FIG. 1.

FIG. 3A illustrates an improved embodiment of a surgical equipment holder 56. Shown is a first arm 58 and a second arm 60. The first arm 58 has a rod 62 slideable therein, the rod 62 having a tapered end 64 on one end. The other end of rod 62 is not visible in this view, but it is configured to interface with a ball connector like the ball connector 24 of the device in FIG. 1. This ball connector could be coupled to a base. The second arm 60 has a rod 66 slideable therein, the rod 66 having a tapered end 68 on one end. The other end of rod 66 is not visible in this view, but it is configured to interface with another ball connector. This ball connector could be coupled to an end effector. A lever 70 is aligned with one of the arms, in this embodiment, with the second arm 60, with the majority of the lever 70 biased away from the arm 60 by a spring element 72. Although a specific style of spring is shown in the example of FIG. 3A for the spring element 72, it should be understood that those skilled in the art are familiar with a wide variety of springs that could be used in place of the illustrated spring element 72.

The lever 70 is coupled to a wedge 74. When the lever 70 is in the position shown in FIG. 3A, the wedge 74 is pressed against tapered end 68 of rod 66 in the second arm 60. This will hold the ball connector (not shown) at the other end of the second arm 60 in position. When the lever 70 is squeezed into the position shown in FIG. 3B, the wedge 74 is pulled away from tapered end 68 of rod 66 in the second arm 60. This will allow the ball connector (not shown) at the other end of the second arm 60 to be moved relative to the second arm 60.

Lever 70 is also coupled to a post 76 which passes through an opening in wedge 74. A wedge 78 is coupled to the post 76. When the lever 70 is in the position shown in FIG. 3A (a locked position), the wedge 78 is pulled up against tapered end 64 of rod 62 in the first arm 58. This will hold the ball connector (not shown) at the other end of the first arm 58 in position. When the lever 70 is squeezed into the position shown in FIG. 3B (an unlocked position), the post 76 is pushed down with the lever, causing the wedge 78 to push away from the tapered end 64 of rod 62 in the first arm 58. This will allow the ball connector (not shown) at the other end of the first arm 58 to be moved relative to the base (also not shown).

Furthermore, when lever 70 is in the position shown in FIG. 3A, a clamping end 80 of the lever 70 is pressed against the end of the second arm 60 while the post 76 and wedge 78 also help to create a clamping force which holds the position of the first arm 58 relative to the second arm 60. When the lever is squeezed into the position shown in FIG. 3B, the clamping end 80 of the lever 70 is lifted from the second arm while the post 76 and wedge 78 release a clamping force, thereby allowing the first and second arms 58, 60 to be moved relative to each other. As a result, it can be seen that this one control feature, lever 70, may be squeezed with a single hand to simultaneously defeat three different locking points. This allows the surgeon to hold the lever with one hand (squeezing the lever) while the other hand positions the scope held by the end effector. During positioning, all degrees of freedom are available to the surgeon and the scope should be very easy to position. Once the desired scope position is established, the surgeon simply releases the lever 70 and all three locking points are again locked into position (for example: 1) the position of the first arm relative to its ball connector, 2) the position of the first arm relative to the second arm, and 3) the position of the second arm relative to its ball connector.) In the prior art devices, this would have taken at least two people and four hands to accomplish, so this embodiment offers clear advantages over the prior art.

Figure 4:
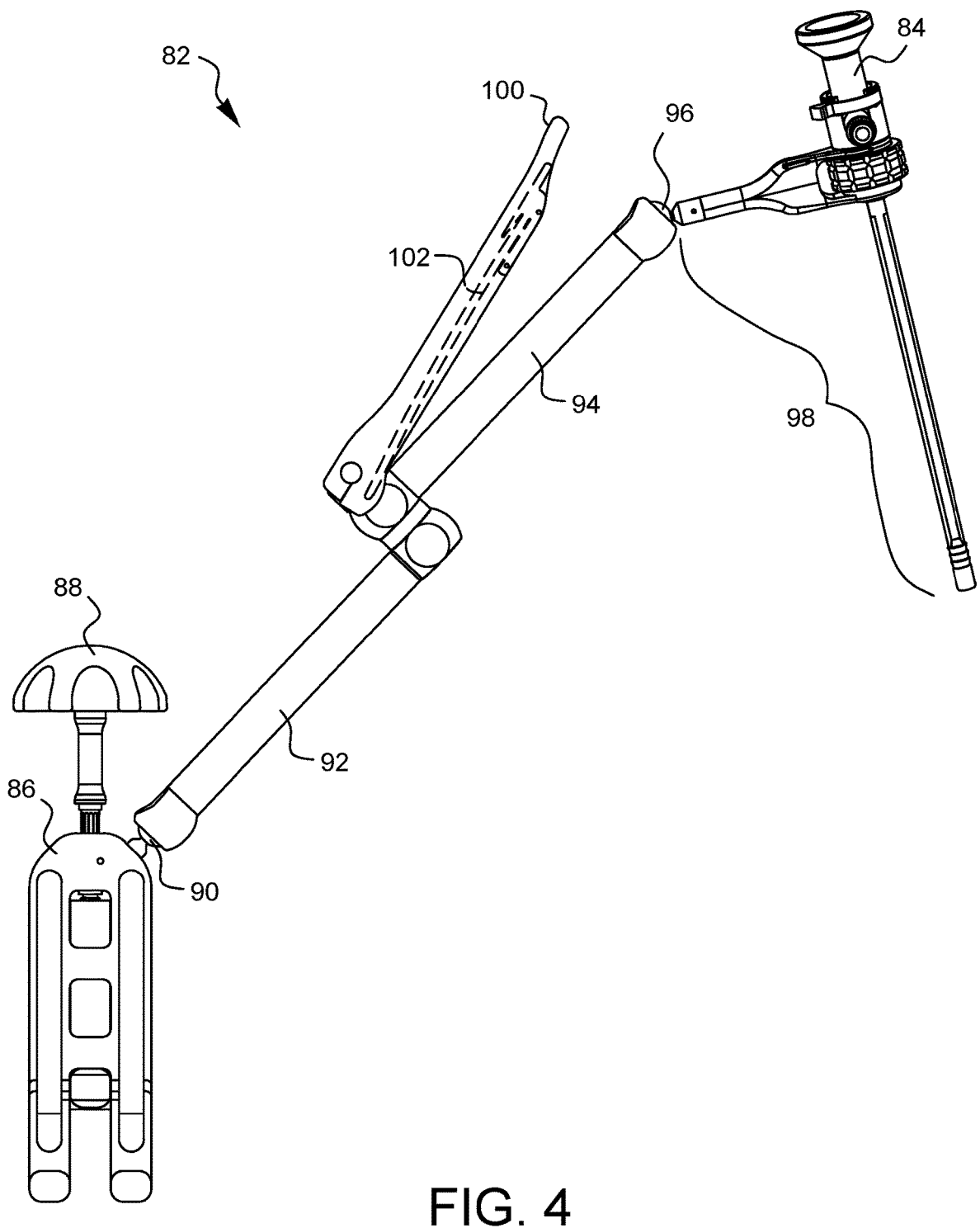
FIG. 4 is a side view of an embodiment of a surgical equipment holder, here shown holding an endoscope.

FIG. 4 illustrates another embodiment of a surgical equipment holder 82, here shown holding one embodiment of an endoscope 84. The surgical equipment holder 82 has a base 86 which is configured in this embodiment to clamp onto the side of a surgical table. A removable key 88 is provided for adjustment of a screw in the base which raises or lowers one of the clamp arms of the base. Other embodiments may use other kinds of removable keys, bases, and clamp bases are known to those skilled in the art. The base 86 has a ball connector 90, similar to the base ball connectors discussed above. Shown is a first arm 92 and a second arm 94. The first arm 92 has a rod slideable therein having a tapered end (not visible in this view). The slideable rod (not visible in this view) within the first arm 92 is configured to interface with the ball connector 90. Similarly, the second arm 94 has a rod slideable therein having a tapered end (not visible in this view). The slideable rod (not visible in this view) within the second arm 94 is configured to interface with a second ball connector 96 which is coupled to an end effector 98. In this embodiment the end effector 98 is configured to hold and position the endoscope 84. A lever 100 is aligned with one of the arms, in this embodiment, with the second arm 94. The majority of the lever 100 is biased away from the second arm 94 by a spring element 102. Although a specific style of spring is shown in the example of FIG. 4, it should be understood that those skilled in the art are familiar with a wide variety of springs that could be used in place of the illustrated spring element 102.

Figure 5A:
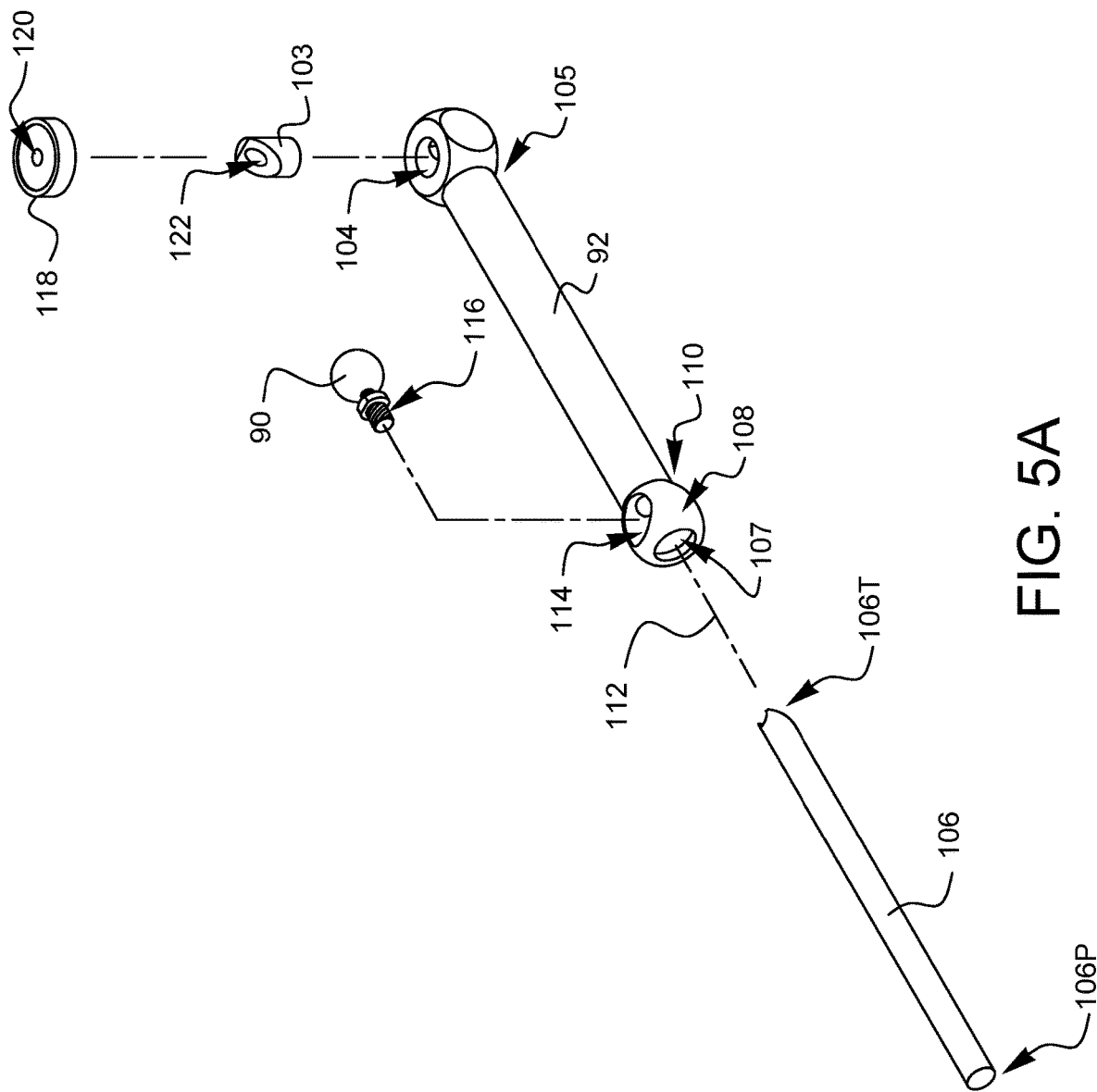

FIGS. 5A-5D are a series of exploded views which show how the surgical equipment holder 82 of FIG. 4 is put together. For simplicity, only the ball connector 90 of the base 86 is shown. As mentioned previously, there are a variety of base configurations which could be used and which are known to those skilled in the art. Regardless of the type of base used, the main requirement is that it have a ball connector 90. As shown in FIG. 5A, wedge 103 is placed into a receiver 104 in the distal end 105 of the first arm 92. A first rod 106 is slid into an opening 107 in a socket 108 and into the hollow interior of the first arm 92. The socket 108 is on a proximal end 110 of the first arm 92, and the opening 107 is aligned with a longitudinal axis 112 of the first arm 92. The rod 106 has a tapered end 106T which can be pressed against the wedge 103 to hold the wedge 103 in the receiver 104. The ball connector 90 is inserted through a second opening 114 in the socket 108. The second opening 114 is larger than the first opening 107, and in fact is large enough to allow the entire ball connector 90 to pass into the socket 108. An attachment portion 116 of the ball connector 90 is passed out of the first opening 107 as the ball connector 90 is inserted through the second opening 114. The first opening 107 is sized to prevent the entire portion of the ball connector 90 from passing through the first opening 107. The proximal end of the rod 106P rides against the ball connector 90 and helps to hold it in the socket 108. A spacer 118 has a hole 120 which aligns with another hole 122 in wedge 103. These two holes 120, 122 are not necessarily the same size. The attachment portion 116 of ball connector 90 may be attached to a base (not shown).

Figure 5B:
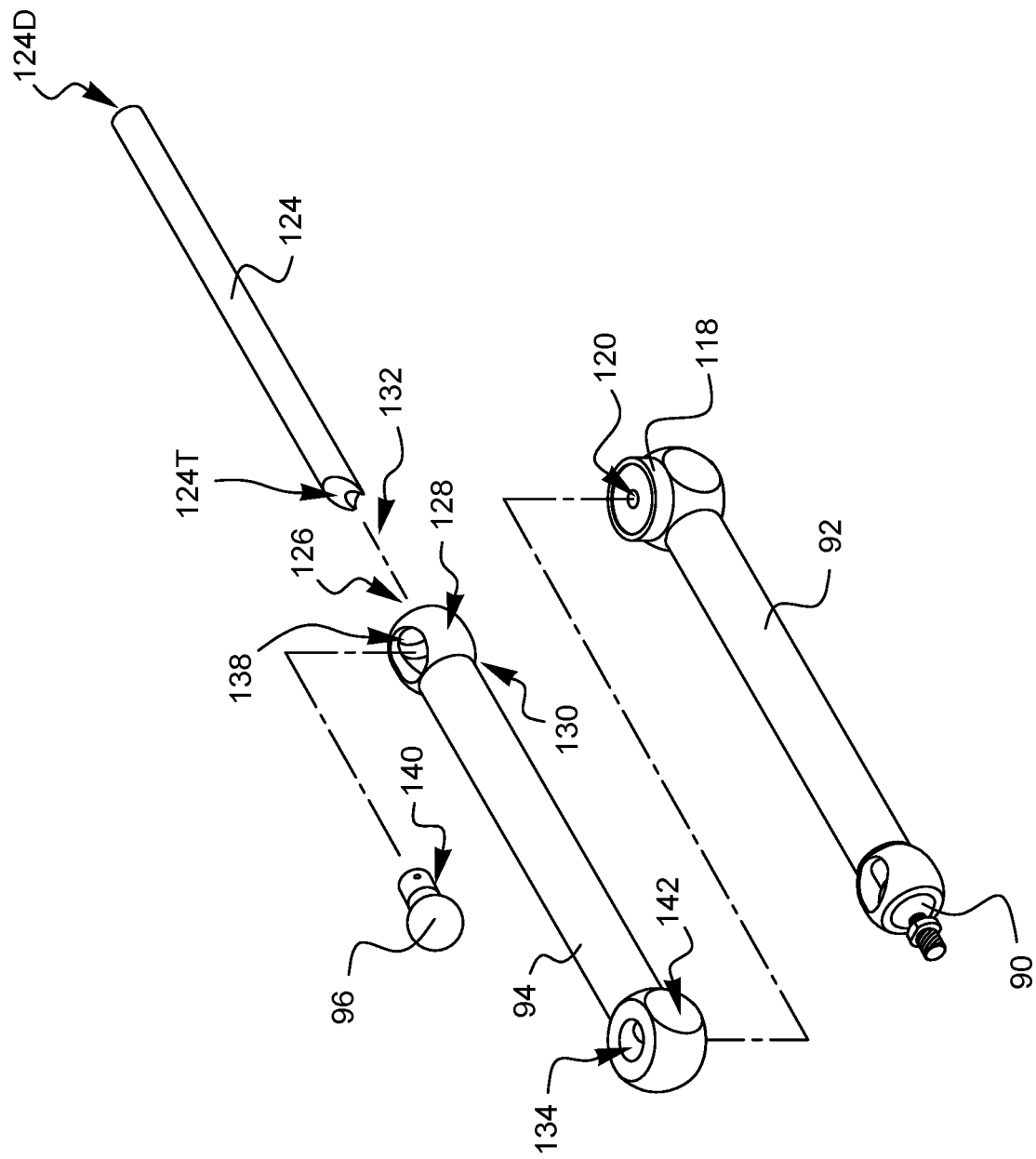

As shown in FIG. 5B, a second rod 124 is slid into an opening 126 in a socket 128 and into the hollow interior of the second arm 94. The socket 128 is on a distal end 130 of the second arm 94, and the first opening 126 is aligned with a longitudinal axis 132 of the second arm 94. The second rod 124 has a tapered end 124T which will be accessible in the receiver 134. A ball connector 96 is inserted through a second opening 138 in the socket 128. The second opening 138 is larger than the first opening 126, and in fact is large enough to allow the entire ball connector 96 to pass into the socket 128. An attachment portion 140 of the ball connector 96 is passed out of the first opening 126 as the ball connector 96 is inserted through the opening 138. The hole of the first opening 126 is sized to prevent the entire portion of the ball connector 96 from passing through the first opening 126. The distal end of the rod 124D rides against the ball connector 96 and helps to hold it in the socket 128. The opening of the receiver 134 in the proximal end 142 of the second arm 94 passes all the way through the second arm 94 and may be aligned with the spacer 118 and the hole 120 therein.

As shown in FIG. 5C, a hinge acceptor 144 is coupled to a post 146 which may be passed through a clearance hole 148 in a lever block 150. A wedge 152 extends outward from the lever block 150, and the lower end of the post 146L extends through the clearance hole 148 in the lever block 150 and through and below the wedge 152. The subassembled hinge acceptor 144, post 146, and lever block 150 with wedge 152 are moved together and the lower end of the post 146L and the wedge 152 are inserted into the receiver 134 so that the lower end of the post 146L is coupled to the hole 122 in wedge 103 (not visible in this view) and so that the wedge 152 sits against the tapered end 124T of the second rod 124.

A spring 154 is aligned into a notch 156 in the lever block 150 and attached to a lever 158 by pins 160 which are passed through corresponding holes 162 in the lever 158 and 164 in the spring 154. A proximal end 166 of the lever 158 is placed over the hinge acceptor 144 and the lever block 150. A first hole 168 in the lever 158 is aligned with a tapped hole 170 in the hinge acceptor 144. A first pivot screw 172 is passed through the first hole 168 and threaded into the tapped hole 170. A second pivot screw 174 is likewise threaded into similar, mirror-imaged holes on the other side of the lever 158 and hinge acceptor 144 (those mirrored holes are not visible in this view).

Another hole 176 in the lever 158 is aligned with a hole 178 in the lever block 150, a hole 180 in the hinge acceptor 144, a further hole 182 in the lever block 150, and a mirrored hole (not visible in this view) in the opposite side of the lever 158. A pin 184 is placed through all of these holes to provide another pivot axis.

Figure 5D:
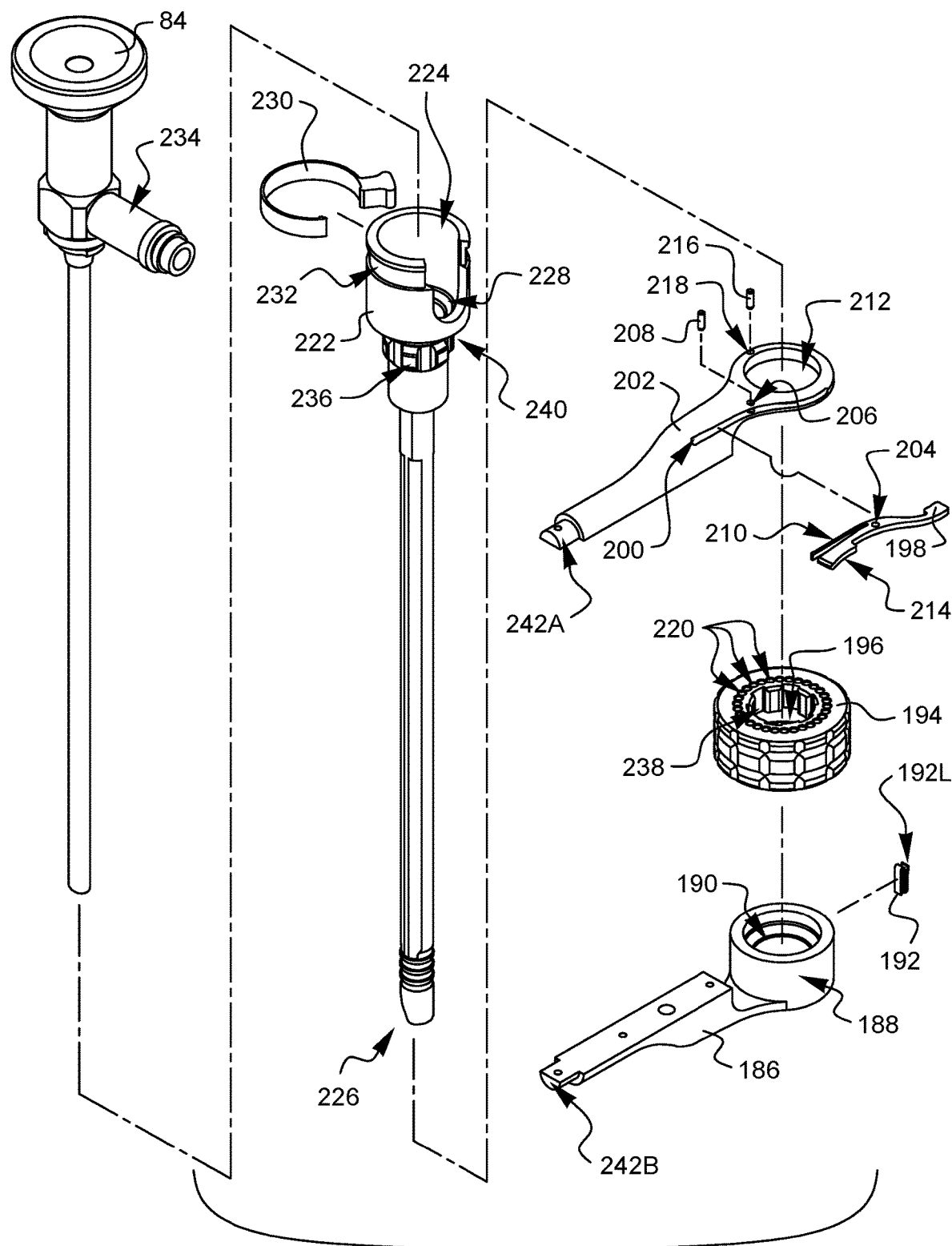

FIG. 5D shows an exploded view of the adapter or end effector 98 which is then coupled to the second ball connector 96 (not shown in this view). A lower yoke 186 has a circular post 188 that defines an opening 190. There is a recess (not visible in this view) on the outside of the post 188 sized to accept a spring latch 192. The spring latch 192 has a latch 192L which extends past the outer surface of the post 188 when the spring latch 192 is in its recess. A cannula rotation dial 194 is placed over the post 188. A groove runs around the inner circumference of the cannula rotation dial. Only a small portion of this groove is visible in FIG. 5D. The Latch 192L of the spring latch 192 engages this groove and helps to hold the cannula rotation dial 194 in place. Since the latch 192L can ride in the groove 196 which passes all the way around the inside of the rotation dial 194, the cannula rotation dial 194 may be rotated freely in this position, however axial movement of the dial is resisted by the latch 192L. A cannula latch 198 is aligned in a slot 200 of upper yoke 202 such that pivot point 204 can be pinned in alignment with hole 206 in upper yoke 202 by pin 208. The cannula latch 198 has a spring 210 which pushes the latch 198 into an opening 212 defined by the upper yoke 202. The cannula latch 198 also has a release 214 which may be pressed, causing the latch to pivot about pin 208 and withdraw from the opening 212. When pressure is removed from release 214, the cannula latch 198 pushes back into the opening 212.

An anti-rotation pin 216 is inserted into hole 218 in the upper yoke 202. The anti-rotation pin 216 extends down past the underside of the upper yoke 202. The upper yoke 202 is then coupled to the lower yoke 186. While the inner groove 196 of the cannula rotation dial 194 is pushed towards the lower yoke 186 and not engaged with the latch 192L, the cannula rotation dial 194 may be rotated freely. When it is desired to lock the rotation dial 194, the rotation dial 194 may be moved axially towards the upper yoke 202. In so doing, one of a plurality of pin receivers 220 positioned around the rotation dial 194 will engage the anti-rotation pin 216 extending down from the upper yoke 202. At approximately the same time, the latch 192L engages the inner groove 196 on the inside of the cannula rotation dial 194, helping to prevent axial movement of the dial which would then allow the rotation dial 194 to rotate again. As long as the rotation dial 194 is left in this position, the rotation dial 194 will hold. To rotate the rotation dial 194 again, the rotation dial 194 would need to be moved axially towards the lower yoke 186 so that the anti-rotation pin 216 disengages from the pin receiver 220.

A scope port cannula 222 is provided. The scope port cannula 222 has a proximal opening 224 in communication with a distal opening 226. The proximal opening 224 may also include a notch 228 to accommodate a light source attachment for an endoscope. A retainer ring 230 snaps onto a retainer groove 232 of the scope port cannula. The retainer ring 230 is rotatable from 1) an orientation that would allow the light source attachment 234 of an endoscope 84 to be placed into the notch 228 when the endoscope 84 is inserted into the scope port cannula 222 to 2) an orientation that would prevent the endoscope 84 from being able to be removed from the scope port cannula 222. The notch 228 also serves to maintain a known rotational position between the endoscope 84 and the scope port cannula 222. The scope port cannula 222 also has one or more keyed teeth 236 on an outer portion of the cannula 222. In use, the distal end of the scope port cannula 222 is inserted into the opening 212 of the upper yoke, through the cannula rotation dial 194, and through the opening 190 in the lower yoke 186 until the one or more keyed teeth 236 on the cannula 222 engage one or more corresponding key features 238 on the inside of the cannula rotation dial 194. The latch 198 engages a groove 240 on the cannula 222, preventing undesired removal of the scope port cannula 222, but allowing the scope port cannula 222 to be rotated as desired by the cannula rotation dial 194 (via the intermeshed keys 236 and corresponding key features 238) when the cannula rotation dial 194 is not engaging the anti-rotation pin 216 as described above.

When the upper yoke 202 and the lower yoke 186 are coupled together, corresponding attachment ends 242A, 242B form a stub which may be coupled to the attachment portion 140 of ball connector 96 discussed above.

Figure 5E:
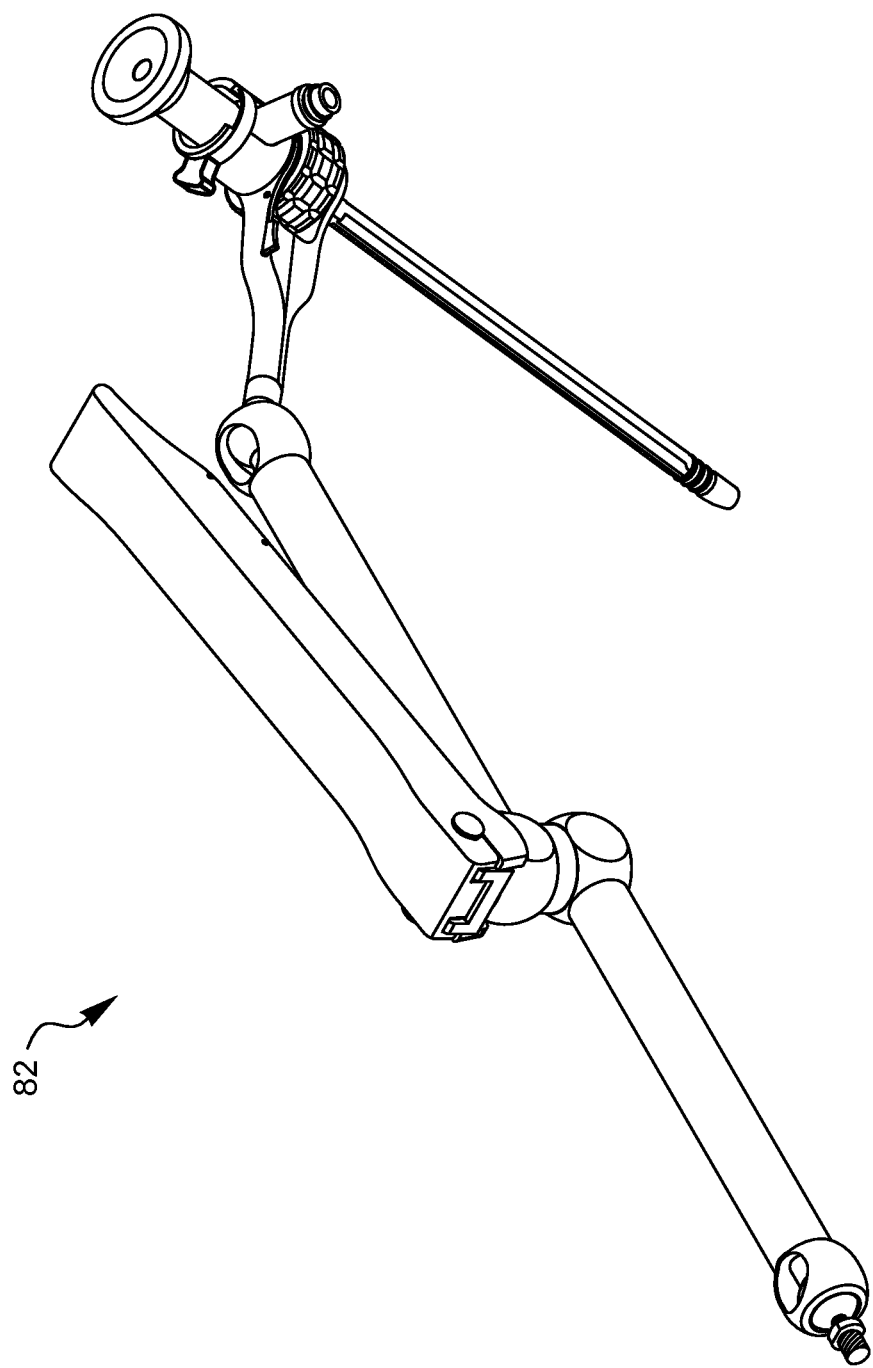
FIG. 5E is a perspective view of the assembled surgical equipment holder from FIGS. 5A-5D with an endoscope installed therein.

FIG. 5E illustrates the assembled surgical equipment holder 82 from FIGS. 5A-5D with an endoscope installed therein. A base is not shown for the reasons discussed above, but could easily be attached.

Figure 6B:
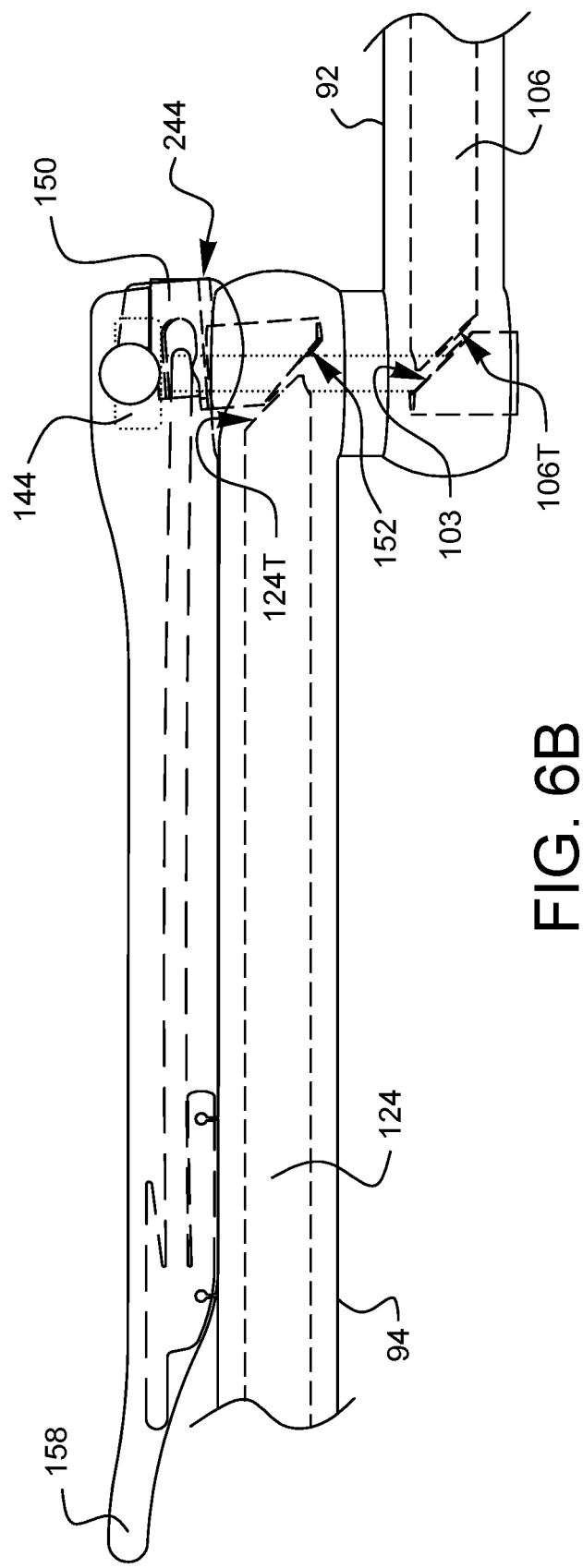

FIGS. 6A and 6B illustrate operation of the lever 158. Lever 158 is coupled via hinge acceptor 144 to a post 146 which passes through an opening in wedge 152. A wedge 103 is also coupled to the post 146. When the lever 158 is in the position shown in FIG. 6A (a locked position), the wedge 103 is pulled up against tapered end 106T of rod 106 in the first arm 92. This will hold the ball connector (not shown) at the other end of the first arm 92 in position. Similarly, in the position of FIG. 6A, the wedge 152 is pressed down against tapered end 124T of rod 124 in the second arm 94. This will hold the ball connector (not shown) at the other end of the second arm 94 in position. When the lever 158 is squeezed into the position shown in FIG. 6B (a released or unlocked position), the post 146 is pushed down with the lever, causing the wedge 103 to push away from the tapered end 106T of rod 106 in the first arm 92. This will allow the ball connector (not shown) at the other end of the first arm 92 to be moved relative to the first arm 92. The squeezed lever of FIG. 6B also rotates the lever block 150 up enough to release the pressure of wedge 152 from tapered end 124T. This will allow the ball connector (not shown) at the other end of the second arm 94 to be moved relative to the second arm.

Furthermore, when lever 158 is in the position shown in FIG. 6A, a clamping end 244 of the lever 158 is pressed against the end of the second arm 94 while the post 146 and wedge 103 also help to create a clamping force which holds the position of the first arm 92 relative to the second arm 94. When the lever 158 is squeezed into the position shown in FIG. 6B, the clamping end 244 of the lever 158 is lifted from the second arm while the post 146 and wedge 103 release a clamping force, thereby allowing the first and second arms 92, 94 to be moved relative to each other. As a result, it can be seen that this one control feature (lever 158) may be squeezed with a single hand to simultaneously defeat three different locking points. This allows the surgeon to hold the lever with one hand (squeezing the lever) while the other hand positions the scope held by the end effector. During positioning, all degrees of freedom are available to the surgeon and the scope should be very easy to position. Once the desired scope position is established, the surgeon simply releases the lever 158 and all three locking points are again locked into position (for example: 1) the position of the first arm relative to its ball connector, 2) the position of the first arm relative to the second arm, and 3) the position of the second arm relative to its ball connector.) In devices like the prior art device of FIG. 1, this would have taken at least two people and four hands to accomplish simultaneously, so this embodiment offers clear advantages over the prior art.

Figure 7:
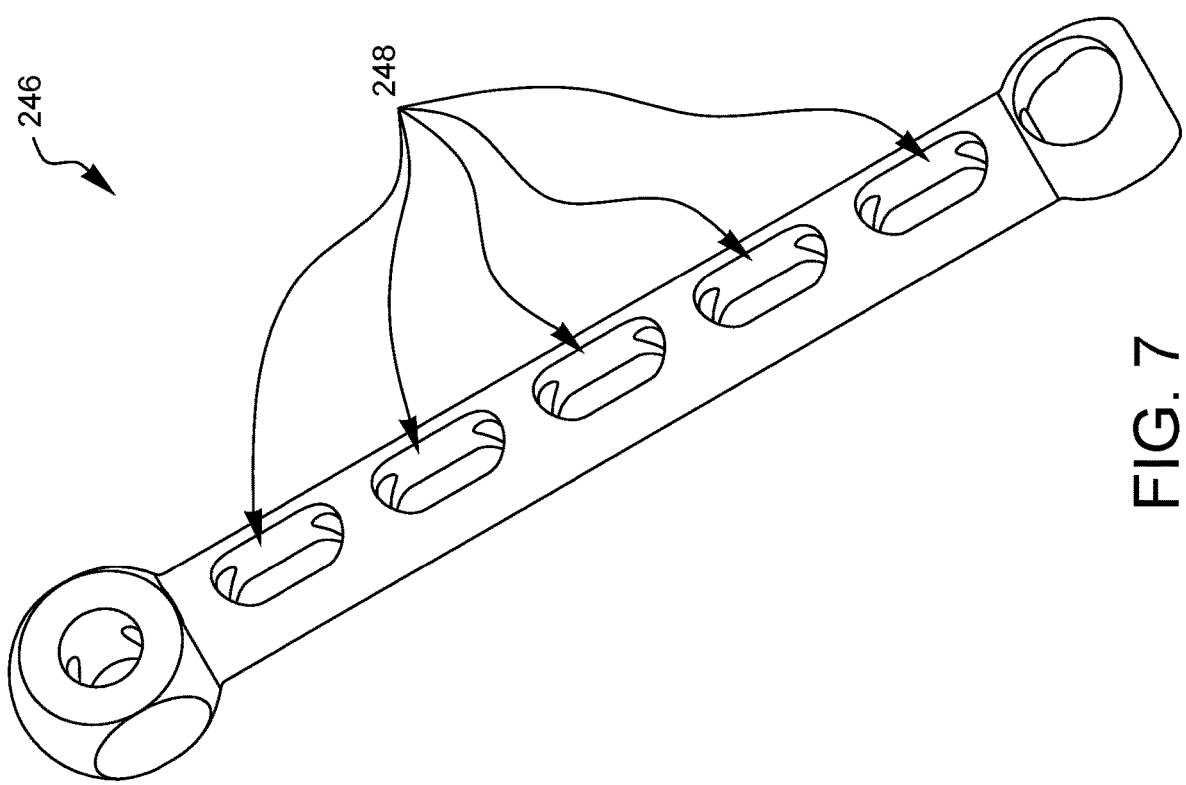
FIG. 7 is a perspective view of an embodiment of an arm which can be used in the surgical device holder.

FIG. 7 is a perspective view of another embodiment of an arm 246 which can be used in a surgical device holder. Arm 246 is similar to the arms discussed above, but has the addition of one or more slots 248 along the arm. The slots 248 will not impact the operation of a rod which needs to slide therein, but they would enable the arm to be cleaned more easily after a surgical procedure has been completed where the surgical device holder was used. Another advantage of a slotted arm would be weight reduction of the assembled arm while retaining its required function and structural integrity.

Figure 8:
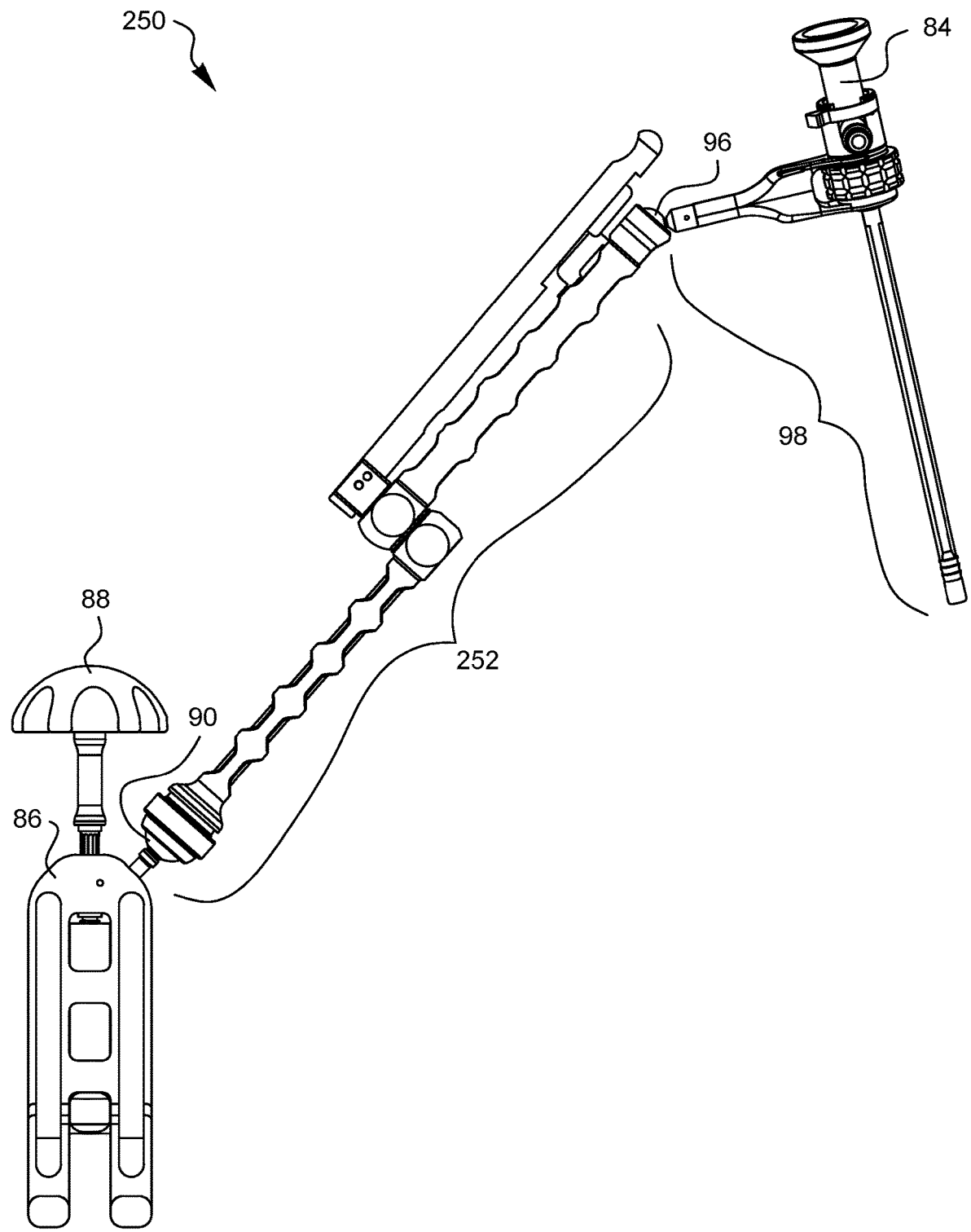
FIG. 8 is a side view of another embodiment of a surgical equipment holder

FIG. 8 illustrates a further embodiment of a surgical equipment holder 250. Like the embodiment of FIG. 4, the surgical equipment holder 250 has a base 86 configured to receive a removeable key 88, the details of which have been discussed above. A ball connector 90 may be coupled to the base 86 as described above. Also, like the embodiment of FIG. 4, the surgical equipment holder 250 has a second ball connector 96 which is coupled to an end effector 98, the details of which were also described above. In this embodiment the end effector 98 is configured to hold and position the endoscope 84. The ball connectors 90 and 96 are coupled to adjustable arms 252. The adjustable arms of this embodiment are further detailed in FIGS. 9A-9F and FIG. 10.

Figure 9A:
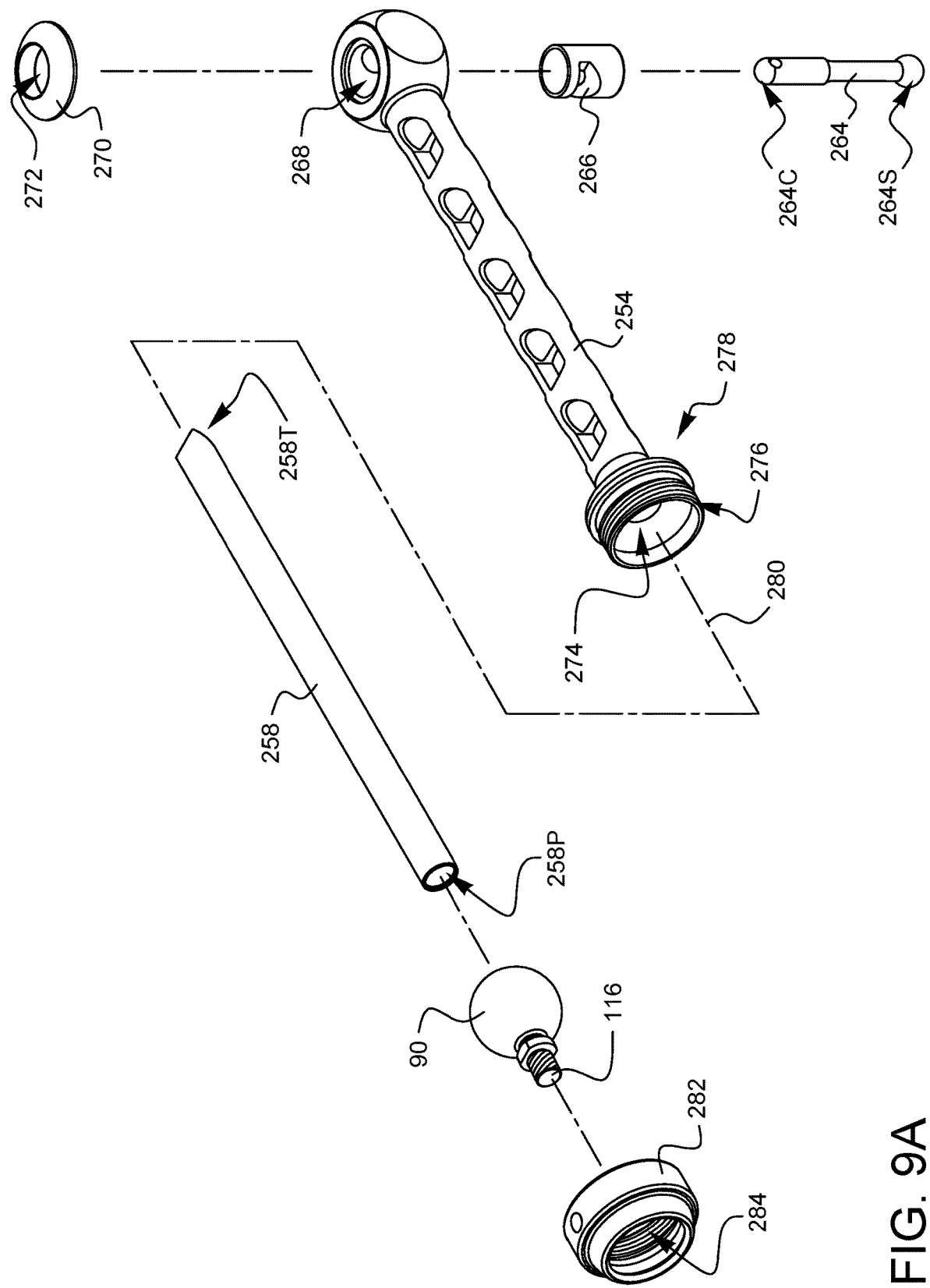

FIGS. 9A-9F are a series of exploded views which show how the adjustable arms 252 are put together. As shown in FIG. 9A, a tension rod 264 having a connection end 264C and a stop end 264S is passed with the connection end 264C first through a first wedge 266. The stop end 264S of the tension rod 264 is sized to prevent the tension rod 264 from passing all the way through the wedge 266. In this embodiment, the stop end 264S is rounded or even spherical in nature. The assembled tension rod 264 and wedge 266 may be passed up through a hole (not visible in this view) on the underside of a receiver 268 in the first arm 254. The connection end 264C of the tension rod 264 will stick up out of the receiver 268. A spacing washer 270 may be placed over the connection end 264C protruding from the receiver 268. In this embodiment, the spacing washer 270 may have a convex outward surface which ideally shares an assembled center point which is approximately coincident with the center of the spherical stop end 264S. The opening in the spacing washer is sized to allow the tension rod 264 to pivot and therefore the first arm 254 to pivot relative to the second arm in more than a single plane without changing the relative spacing between parts joined by the tension rod. The first rod 258 is slid into an opening 274 in a socket 276 and into the hollow interior of the first arm 254. The socket 276 is on a proximal end 278 of the first arm 254, and the opening 274 is aligned with a longitudinal axis 280 of the first arm 254. The rod 258 has a tapered end 258T which can be pressed against the wedge 266 to hold the wedge 266 in the receiver 268. The ball connector 90 is placed into the socket 276 against the proximal end 258P of the rod 258, and a retainer 282 is attached over the ball connector 90 to the socket 276 in order to hold the ball connector 90 in the socket 276. The proximal end 258P of the rod, which rests against the ball connector 90, may be concave so that the circumferential edge of the rod's proximal end 258P is what actually contacts the ball connecter 90. The retainer 282 has an opening 284 through which the attachment portion 116 may protrude. As with previous embodiments, the attachment portion may be attached to a base (not shown).

Figure 9B:
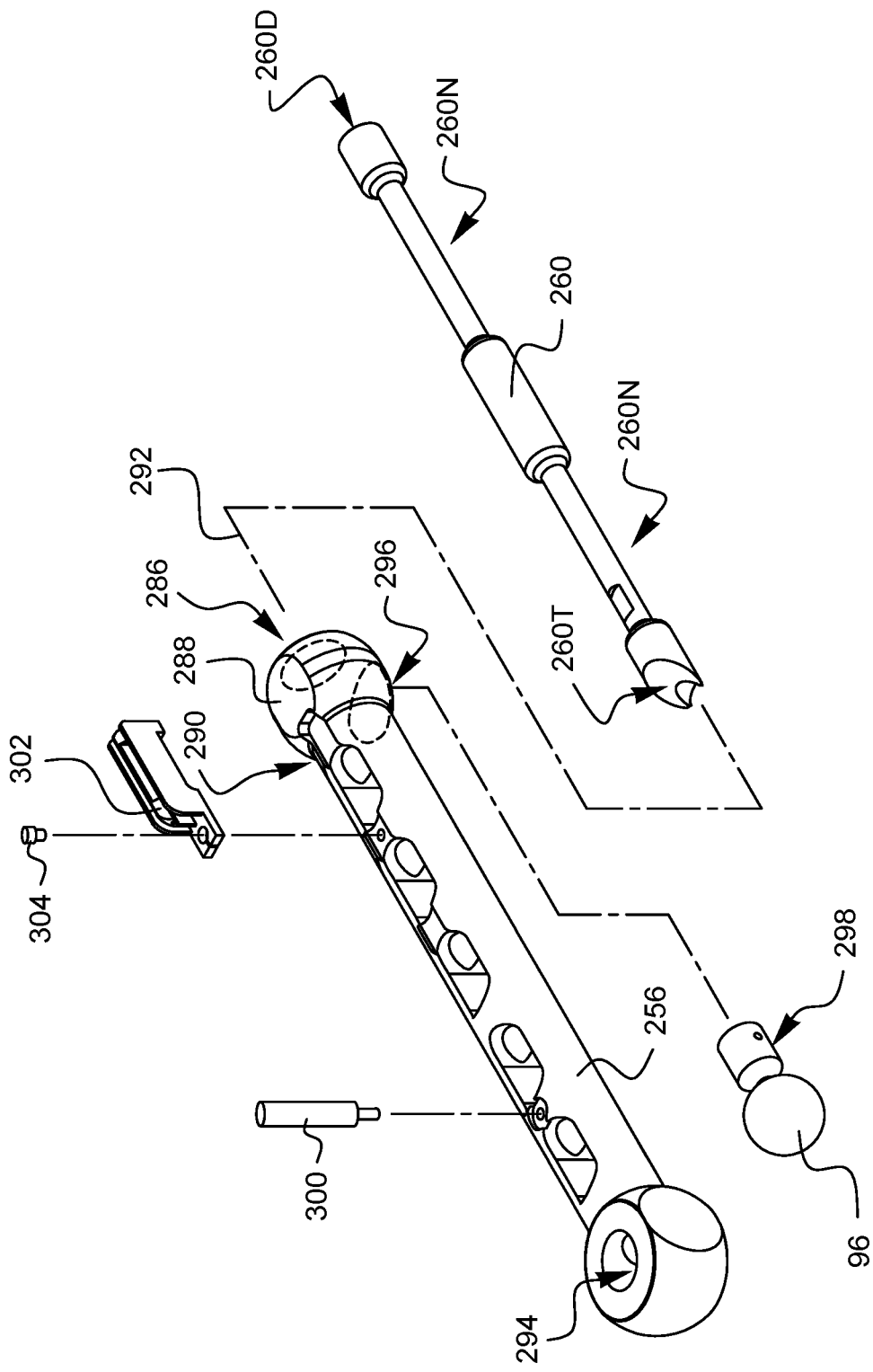

As shown in FIG. 9B, the second rod 260 is slid into an opening 286 in a socket 288 and into the hollow interior of the second arm 256. The socket 288 is on a distal end 290 of the second arm 256 and the opening 286 is aligned with a longitudinal axis 292 of the second arm 256. In this embodiment, the rod 260 has some narrower portions 260N which provide weight relieve the overall apparatus. The rod 260 also has a tapered end 260T which will be accessible in a receiver 294 of the second arm 256. A ball connector 96 is inserted through a second opening 296 in the socket 288. The second opening 296 is larger than the first opening 286, and is large enough to allow the entire ball connector 96 to pass into the socket 288 while the attachment portion 298 passes out of the first opening 286. The first opening 286 is sized to prevent the entire portion of the ball connector 96 from passing through the first opening 286. The distal end of the rod 260D rides against the ball connector 96 and helps to hold it in the socket 288. A lever alignment guide 300 may also be coupled to the second arm 256. Further, a lever catch 302 may be coupled to the second arm 256, for example, with a pin 304 or other attachment technique known to those skilled in the art.

Figure 9C:
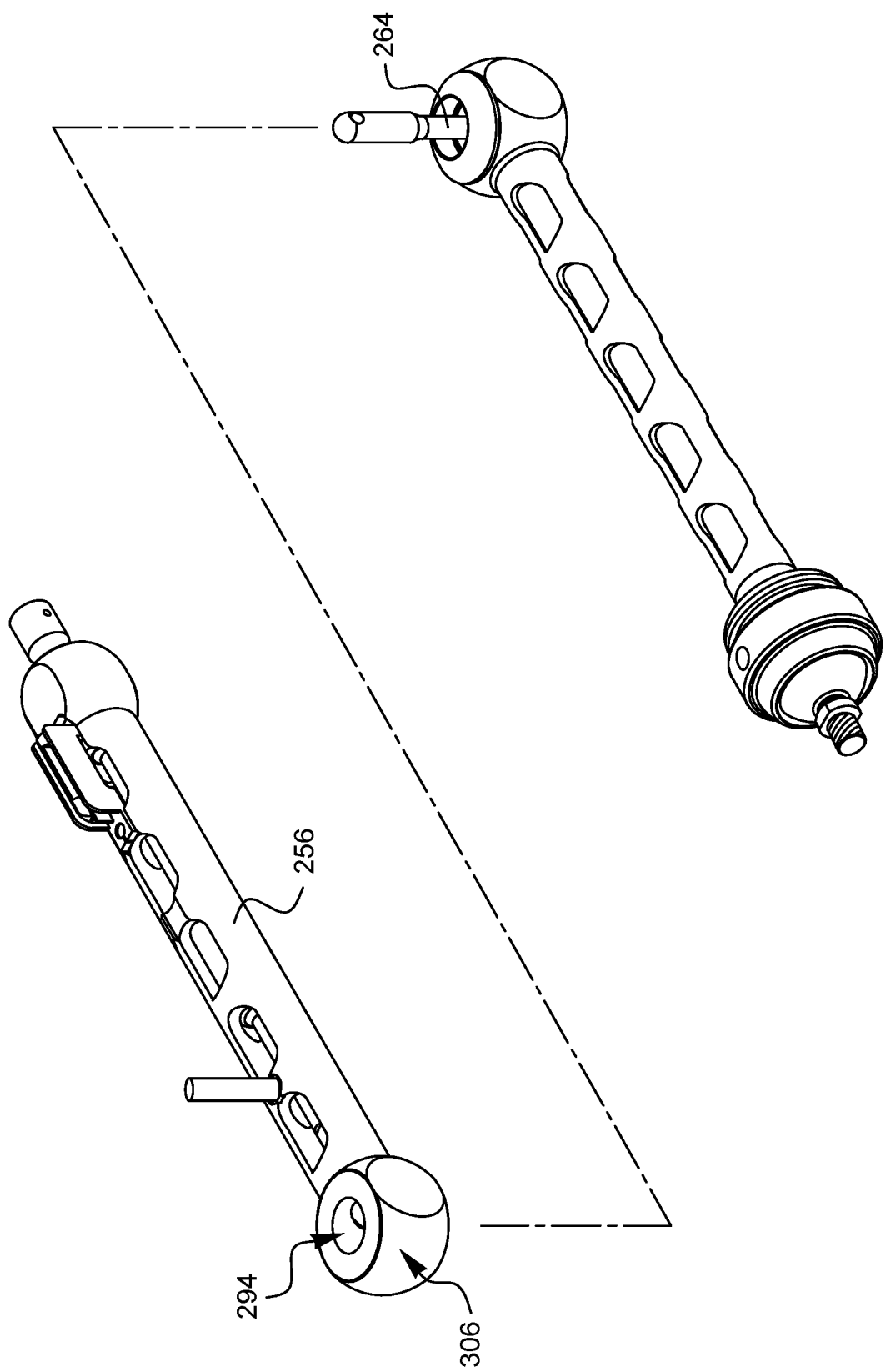
Figure 9D:
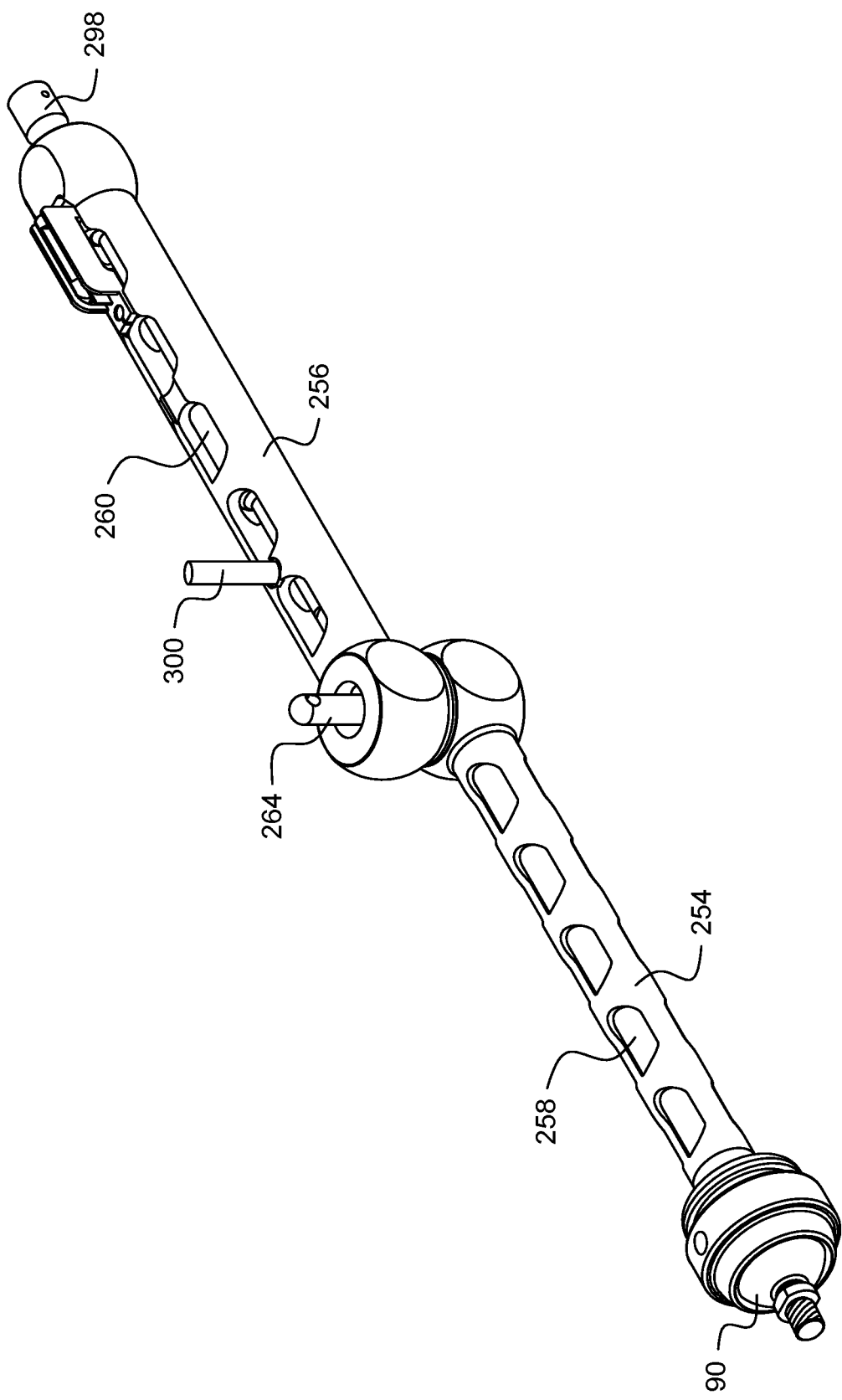

As shown in FIG. 9C, the receiver opening 294 (which goes all the way through the receiver 306 of the second arm 256) may be aligned with the tension rod 264. FIG. 9D illustrates the resultant assembly of items from FIG. 9C.

Figure 9E:
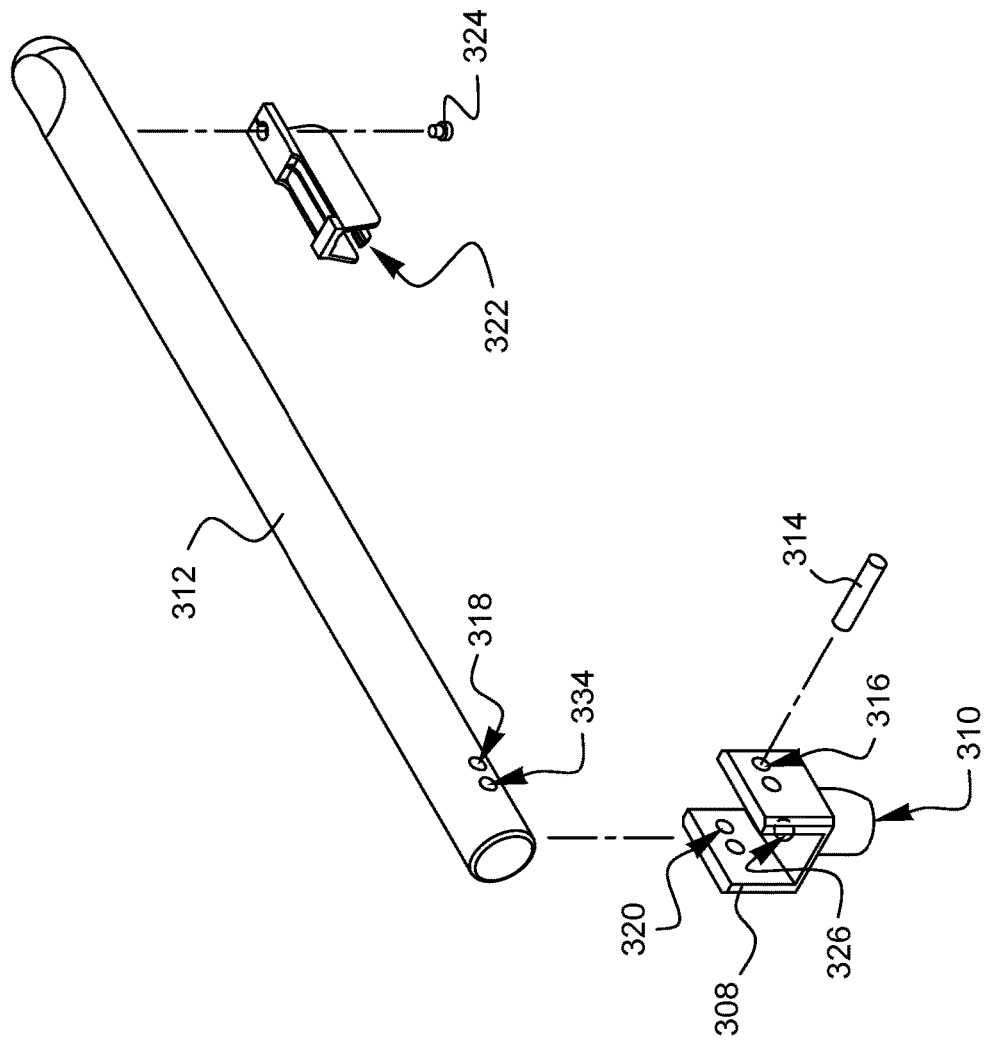

FIG. 9E illustrates another sub-assembly surrounding a lever block 308 which has a wedge 310. A lever 312 is pivotably coupled to the lever block 308 by a lever pivot pin 314 inserted through hole 316 in the lever block 308, hole 318 in the lever 312, and hole 320 in the lever block 308. A lever latch 322 is coupled to the lever 312, for example by pin 324 or by other suitable methods known to those skilled in the art.

As shown in FIG. 9F, the lever arm assembly of FIG. 9E can be brought together with the assembly of FIG. 9D. As can be seen partially in FIG. 9E, the lever block 308 and wedge 310 have a channel 326 which passes therethrough. Referring to FIG. 9F, this channel 326 allows the wedge 310 to be passed over the tension rod 264 so that the wedge 310 sits against the tapered end 260T (not visible in this view) of the second rod 260. A tension clearance opening 328 in the bottom of the lever 312 allows the connection end 264C to pass into the lever 312. The lever 312 may be aligned so that a tension pivot pin 330 may be passed through pass-through hole 332 in the lever block 308 and into hole 334 (visible in FIG. 9E), through hole 336 in the tension rod 264, and into an aligned hole (not visible in this view) in lever 312 which corresponds to hole 334. Once installed, the tension pivot pin 330 does not interfere with the lever block 308, but it does allow the tension rod 264 to pivot with respect to the lever 312.

Figure 10:
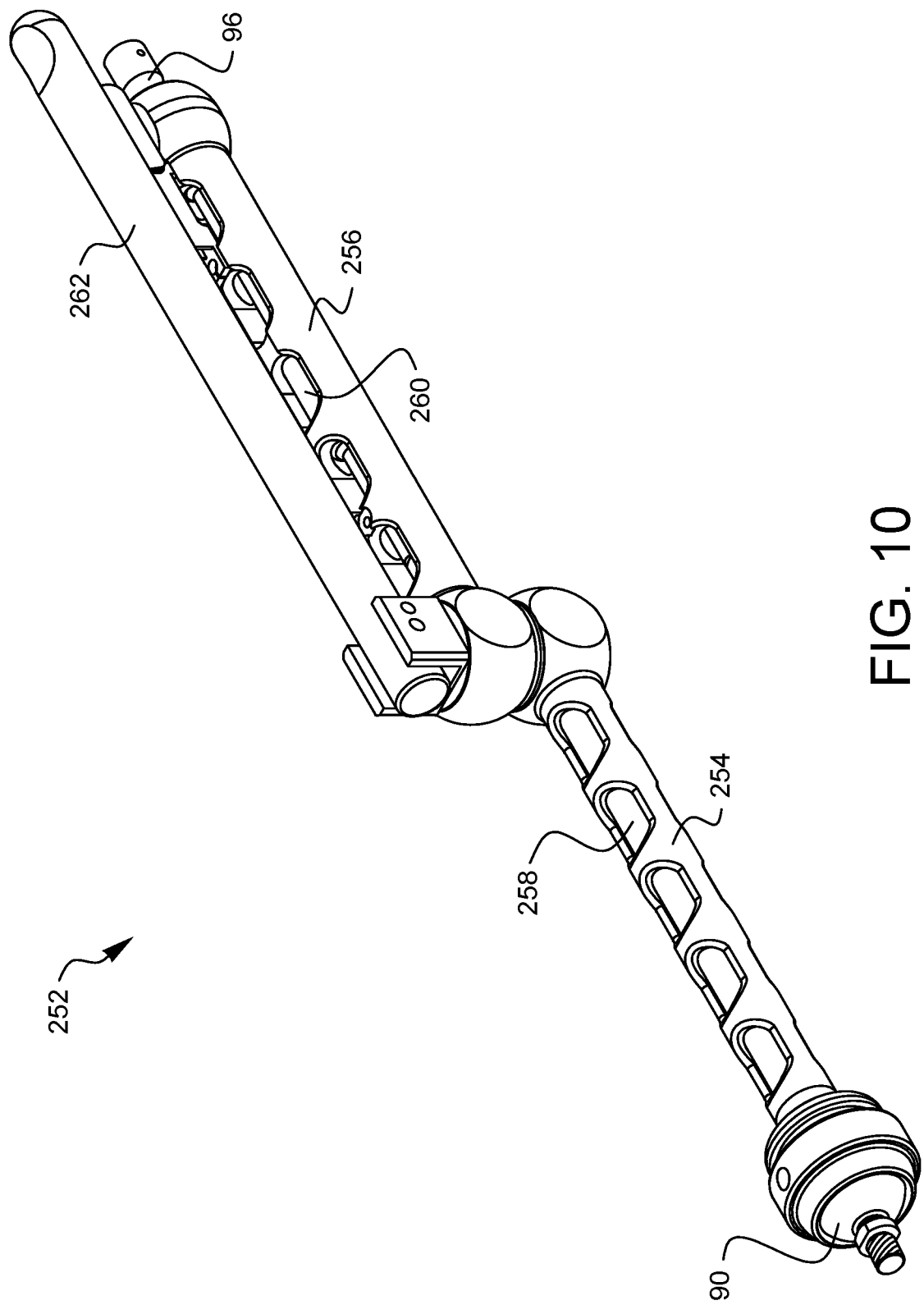
FIG. 10 is a perspective view of the assembled adjustable arms of the surgical equipment holder of FIG. 8.

The assembled adjustable arms 252 are shown in FIG. 10, coupled to the ball connectors 90, 96. Shown are a first arm 254 and a second arm 256. The first arm 254 has a rod 258 slideable therein having a tapered end (the tapered end is not visible in this view). The slideable first rod 258 within the first arm 254 is configured to interface with the first ball connector 90. Similarly, the second arm 256 has a rod 260 slideable therein having a tapered end (the tapered end is not visible in this view). The slideable second rod 260 within the second arm 256 is configured to interface with the second ball connector 96. A lever 262 is aligned with one of the arms, in this embodiment, with the second arm 256.

Figure 11A:
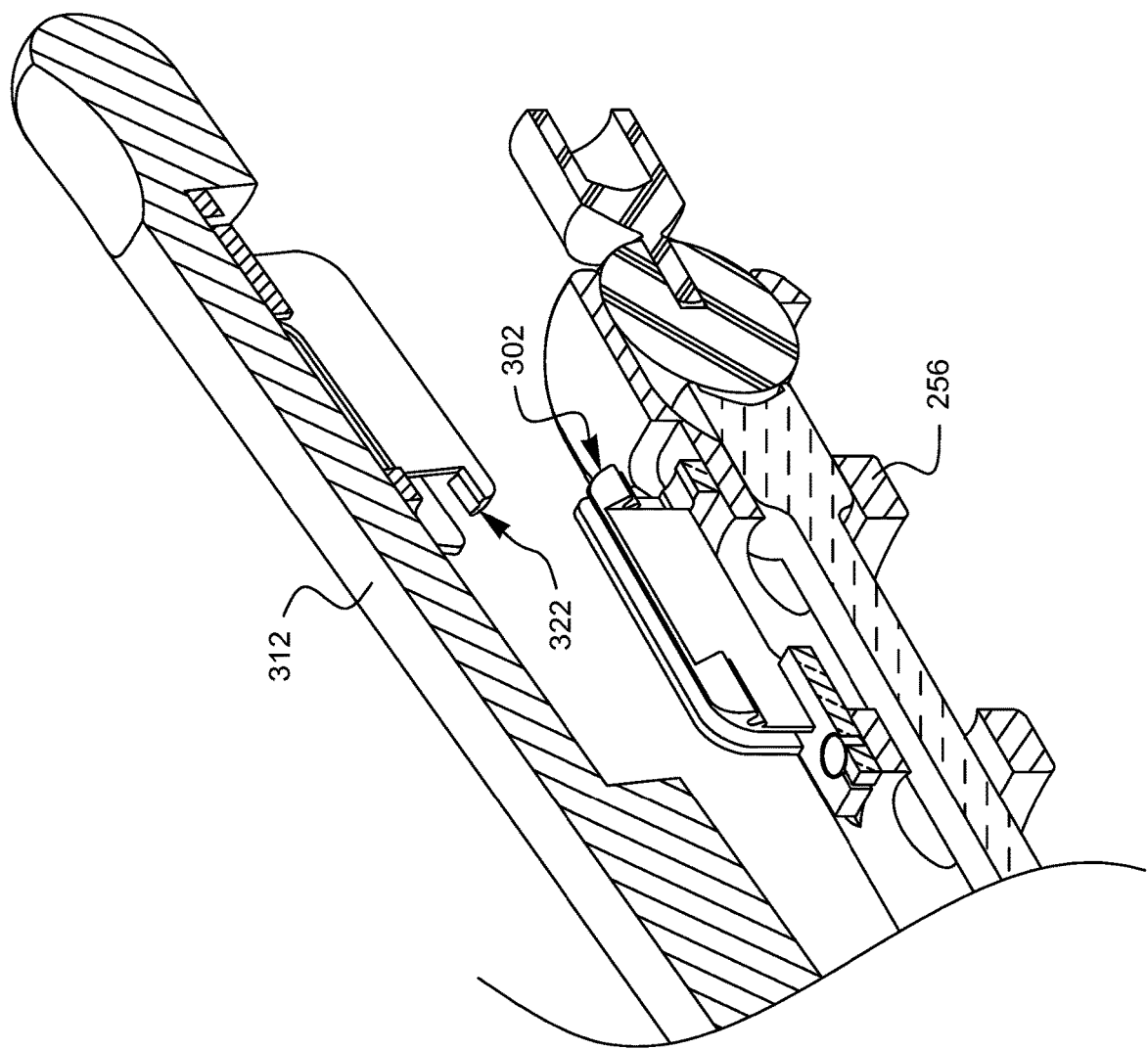
FIGS. 11A-11D are partial cross-sectional views demonstrating operation of one embodiment of a lever latch and catch system for the surgical equipment holder of FIG. 8.
Figure 11B:
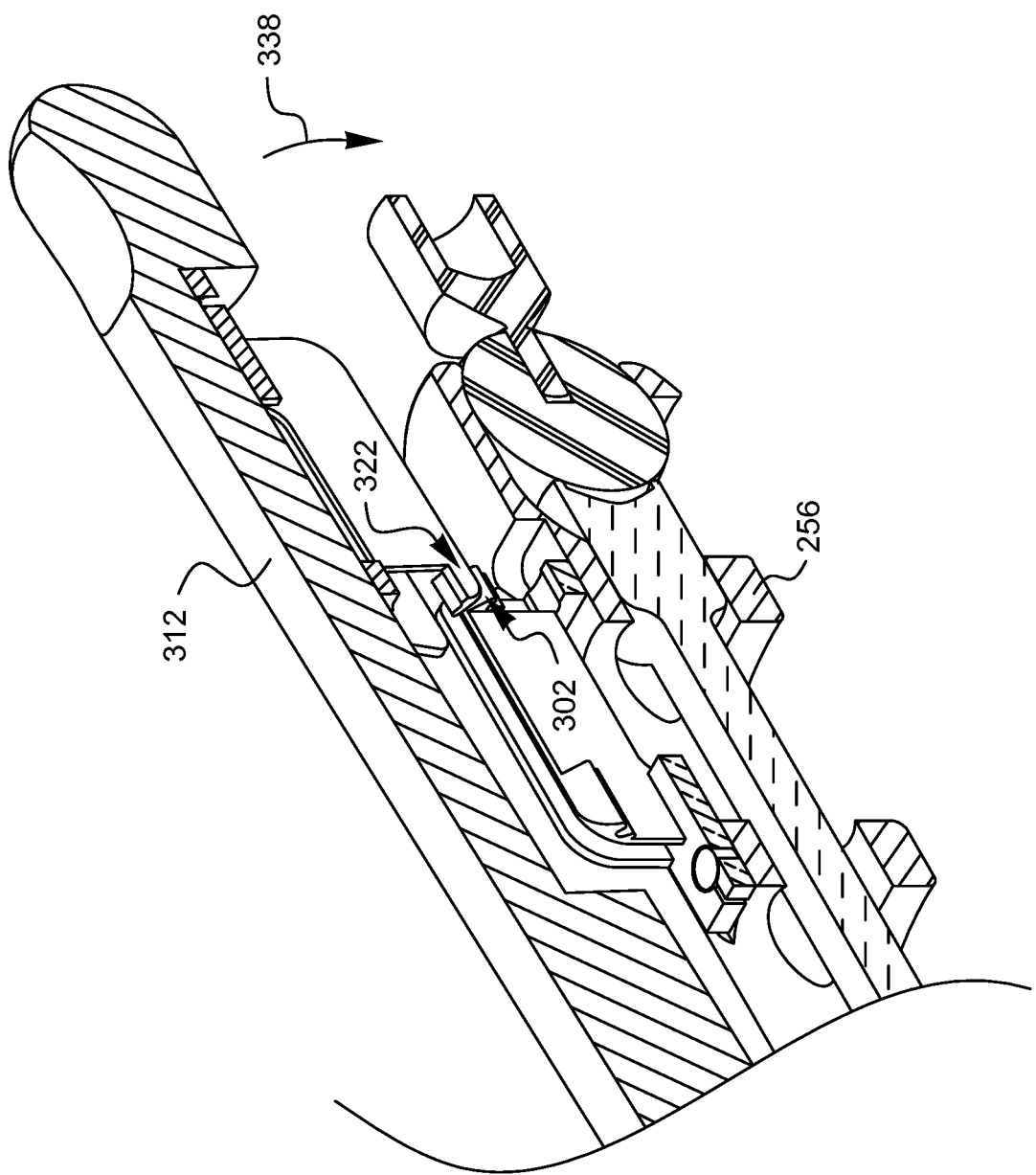
Figure 11C:
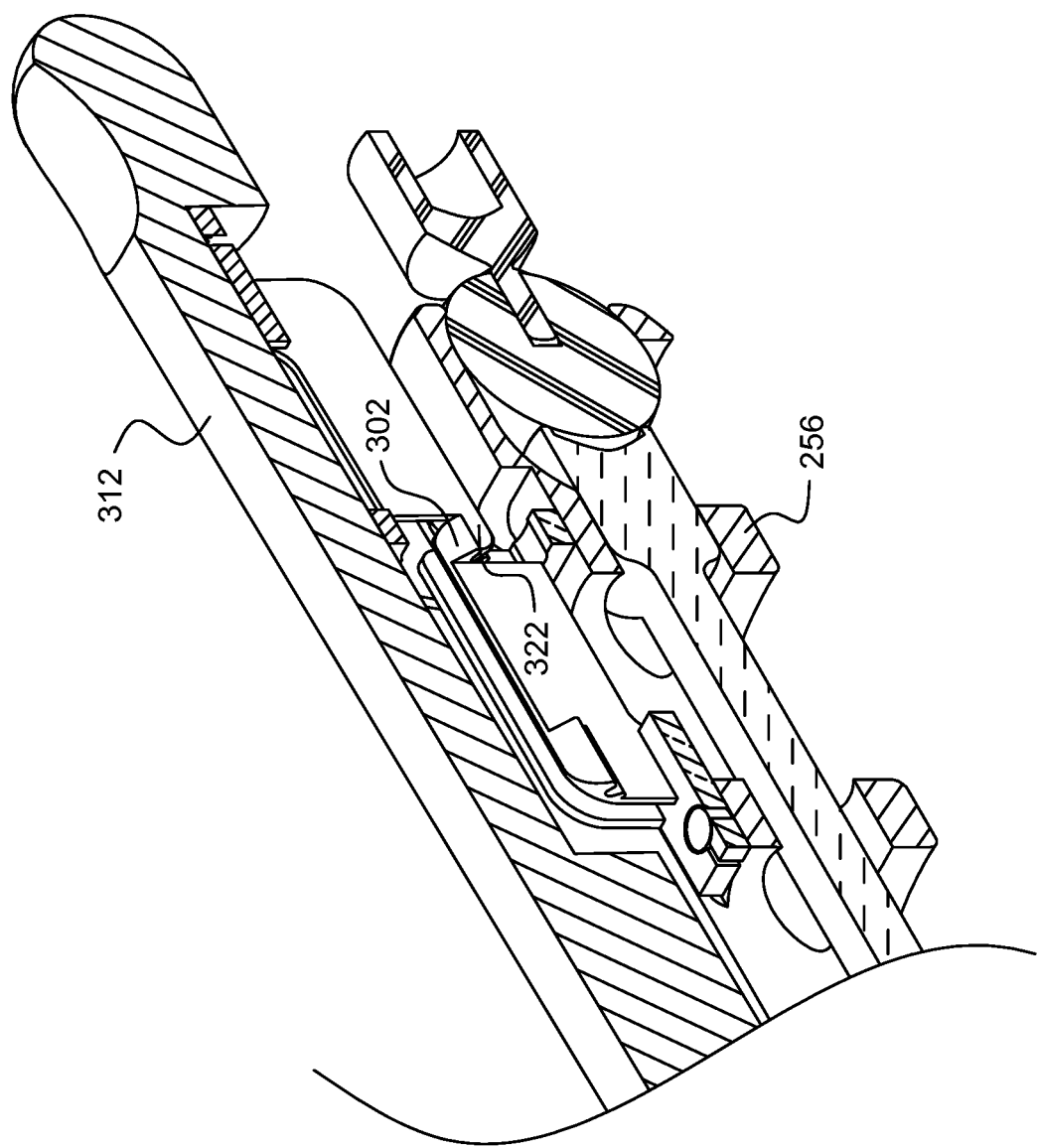
Figure 11D:
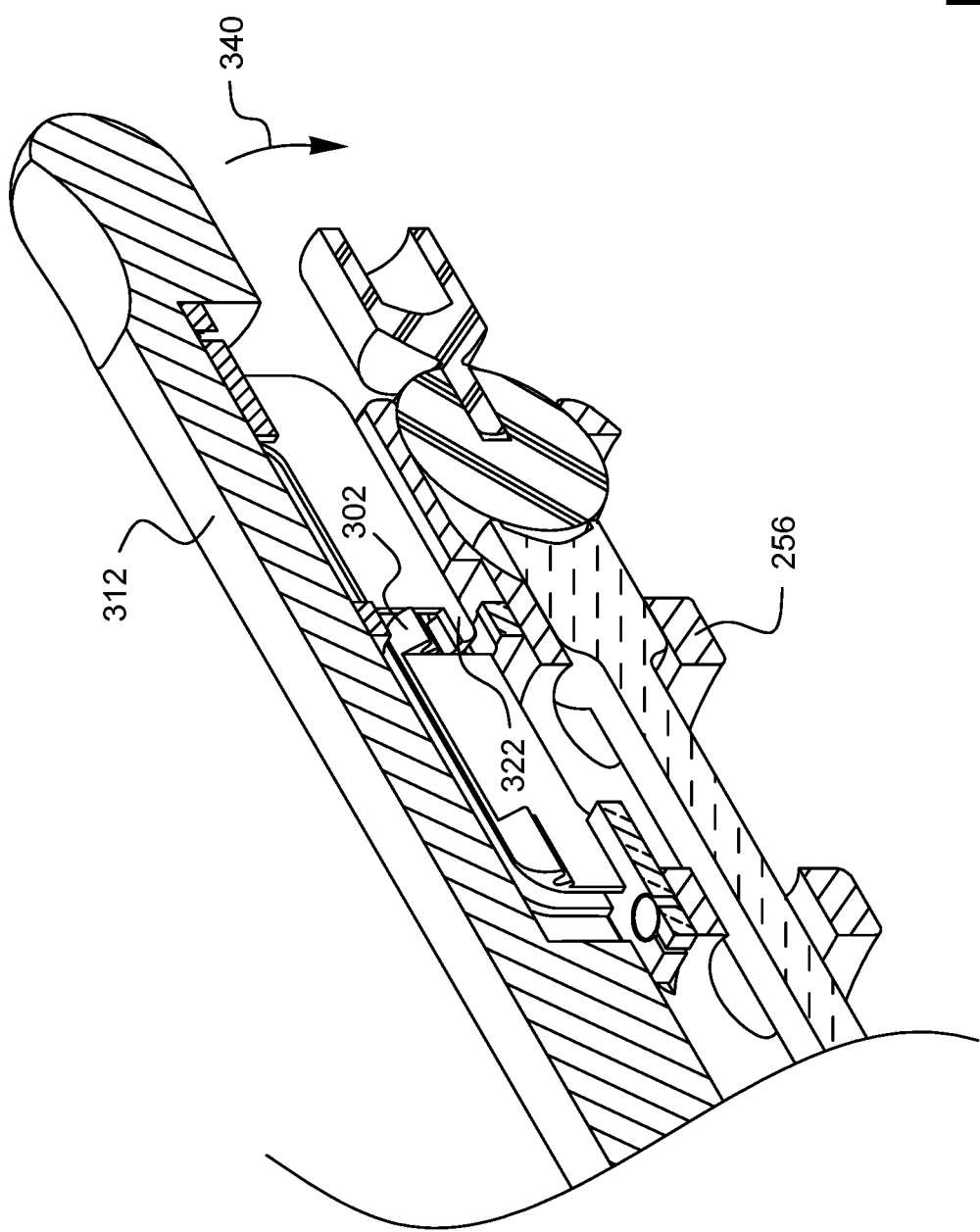

When installed, the tension rod 264 is sized such that the longer portion of lever 312 is pivoted up (away from the second arm 256). As illustrated in the partial cross-sectional view of FIG. 11A, this leaves the lever latch 322 separated from the lever catch 302 in the unlocked position. As illustrated in FIG. 11B, the lever 312 may be compressed or squeezed towards 338 the second arm 256 such that the lever latch 322 makes contact with the lever catch 302. With just a bit more squeezing, the lever latch 322 rides over the lever catch 302 and as the compression is released, the latch 322 and catch 302 are engaged as illustrated in FIG. 11C. In this state, the lever latch 322 and the lever catch 302 are slightly deflected from their normal position, and the lever 312 is held in a compressed state (locked position), which causes the tension rod (not visible in this view) to be under tension. The differences of what happens when the tension rod 264 is not under tension (FIGS. 12A-B) verses when it is under tension (FIGS. 13A-B) will be discussed later in this specification. In order to release the tension, the lever 312 is further squeezed towards 340 the second arm 256 as illustrated in FIG. 11D. This causes the lever latch 322 and the lever catch 302 to clear each other, allowing them to spring back to a non-deflected position. In this non-deflected position, while the lever catch 302 is above the lever latch 322, the latch 322 and catch 302 will not grab onto each other. Instead, when a squeezing force is released from the lever 312, the tension on the tension rod 264 (not visible in this view) will cause the lever 312 to return to the unlocked position of FIG. 11A again. In this way, the latch 322 and catch 302 mechanism enables the adjustable arms 252 to be in an untensioned (unlocked) state (FIG. 12A) or held in a tensioned (locked) state (FIG. 13A). The desired positioning and engagement of either the locked or unlocked state can be selected by the operator using only one hand.

Figure 12A:
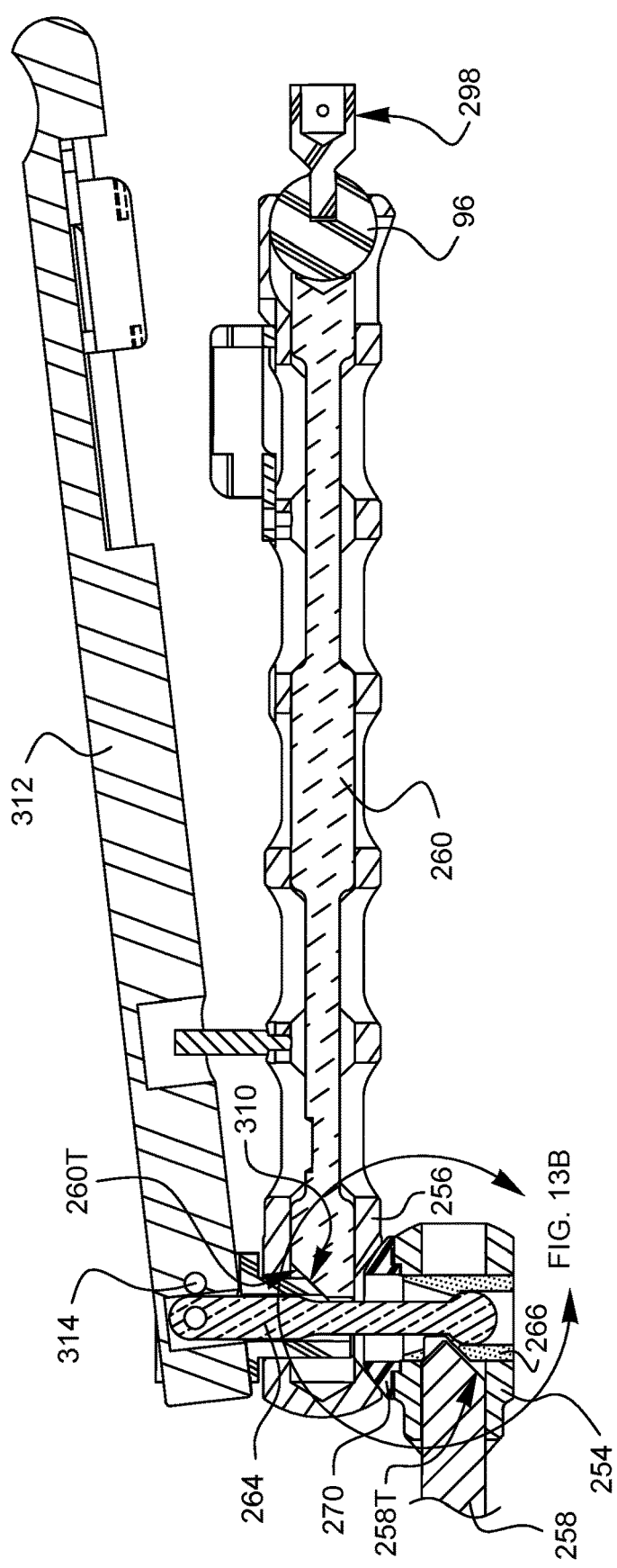
FIG. 12A is a side cross-sectional view of a portion of the surgical equipment holder of FIG. 8 with the lever in an unlocked position.
Figure 12B:
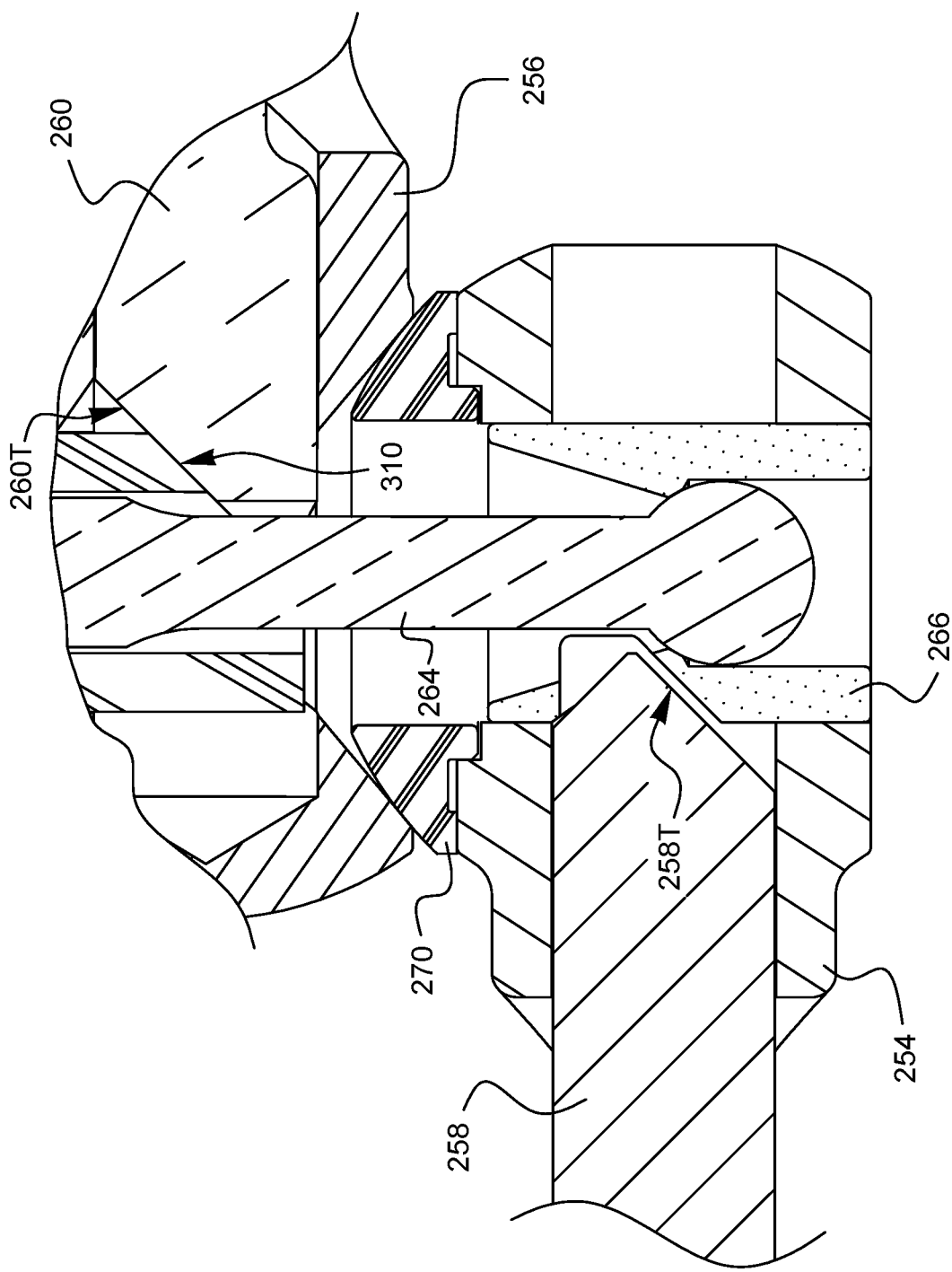
FIG. 12B is an enlarged side cross-sectional view of a portion of a middle joint interface between the first and second arms of the surgical equipment holder of FIG. 12A an unlocked state.

FIG. 12A is a partial cross-sectional view of a portion of the adjustable arms. In the state of FIG. 12A, the tension rod 264 is untensioned. The lever 312 is pivotable about lever pivot pin 314, and in the position of FIG. 12A, lever 312 has pushed the attached tension rod 264 downward (in the orientation shown). This allows wedge 266 to slightly disengage tapered end 258T of rod 258, thereby relaxing the grip of the rod 258 on ball connector 90 (not shown in this view). In this position, lever 312 is not pushing down on wedge 310, so pressure between wedge 310 and tapered end 260T is also reduced, thereby relaxing the grip of the rod 260 on ball connector 96. There is also less compression of the spacing washer 270 between the first and second arms 254, 256, thereby allowing the first arm 254 to be pivoted with respect to the second arm 256. In this embodiment, since the spacing washer 270 is curved, the arms 254, 256 may be pivoted relative to each other in the same plane or in different planes. This provides the ability for an operator to position the arms and an end effector coupled to the ball connector 96 easily in any desired position. A more detailed cross-sectional view of the unlocked or open state of this embodiment is shown in FIG. 12B.

Figure 12C:
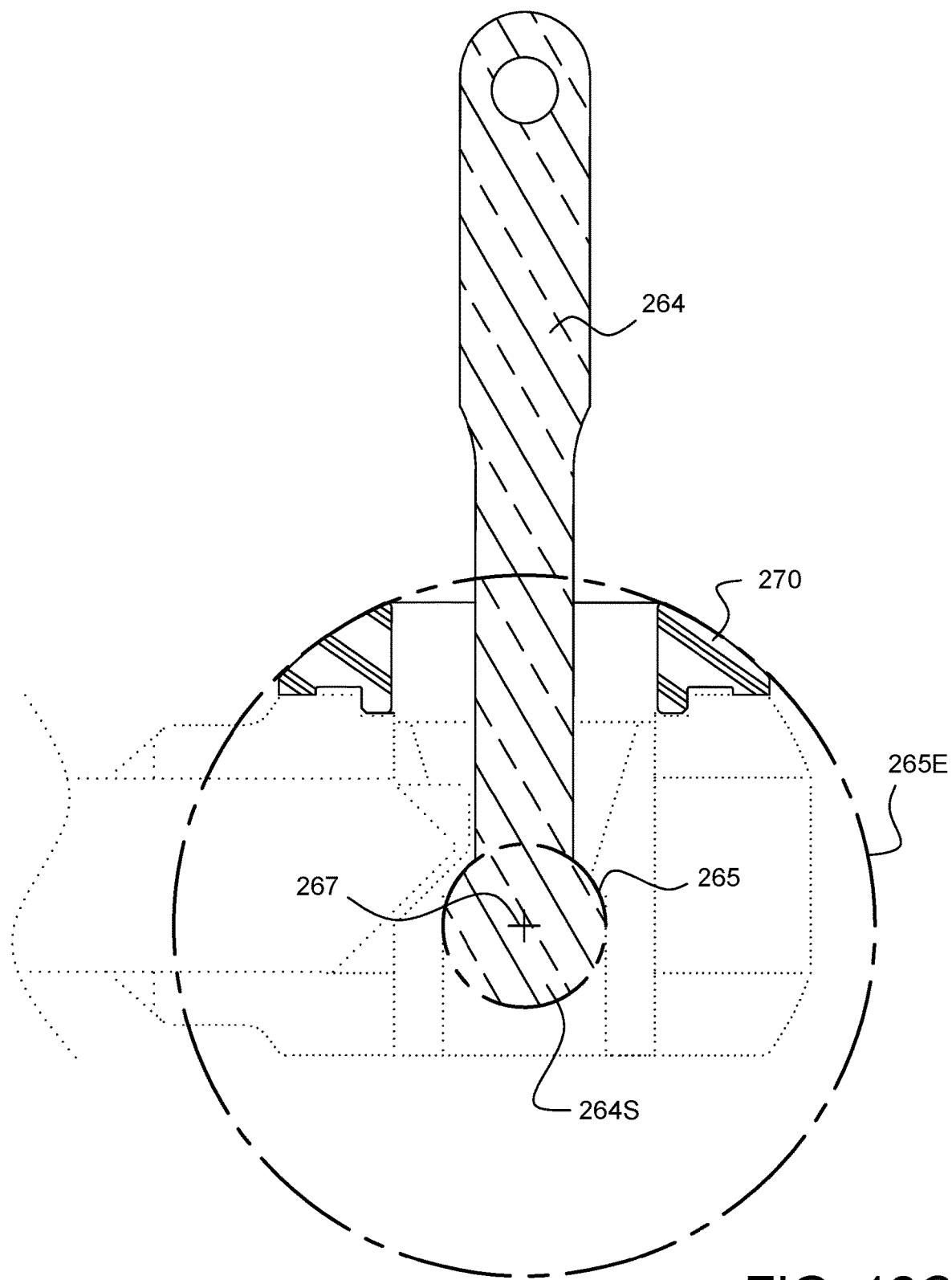
FIG. 12C is a further focused side cross-sectional view of a portion of the middle joint interface from FIG. 12B highlighting an aspect of the spatial relationship between a tension rod stop end and a spacing washer.

FIG. 12C shows a further detailed cross-sectional view of the tension rod 264, detailing its position within the receiver 268 of the first arm 254 and relative to the spacing washer 270 as shown in FIG. 10A. This view illustrates an aspect of the spatial relationship between the stop end 264S of the tension rod 264 and the spacing washer 270. The size of the interior concentric circle 265 in FIG. 12C is the same size as a circle corresponding to the spherical portion of the tension rod stop end 264S, while the size of the exterior concentric circle 265E matches an arc corresponding to the convex outward surface of the spacing washer 270. Furthermore, the spacing washer shares an assembled center point 267 which is approximately coincident with the center of the spherical stop end of the tension rod. The nature of this geometrical and spatial relationship between the tension rod stop end 264S and the spacing washer 270 allows for a consistent application of force when lever 312 is squeezed to engage the locked position of the surgical equipment holder 250 (FIGS. 13A and 13B) regardless of the relative angle or position of the first arm 254 to the second arm 256.

Figure 13B:
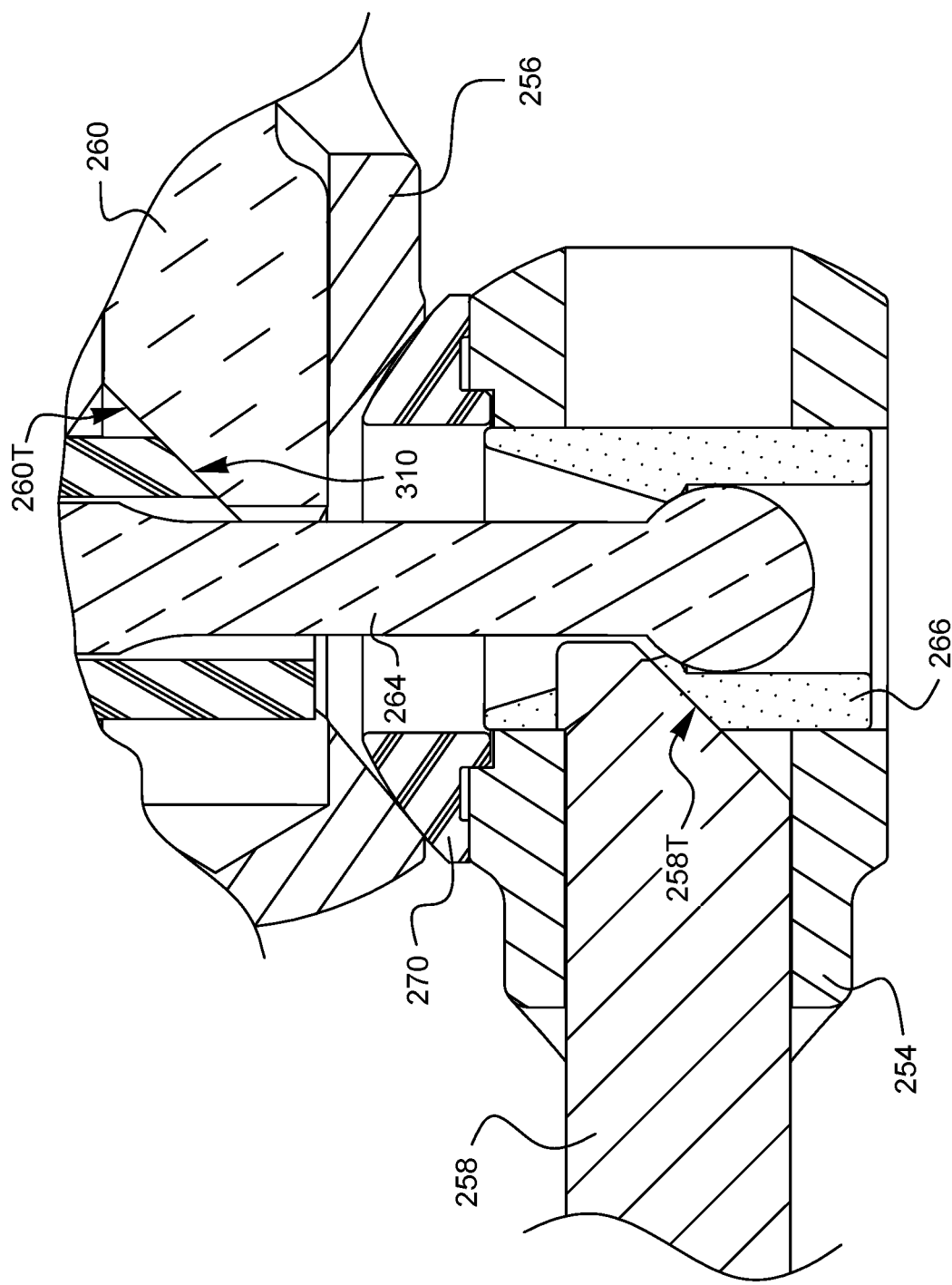

When a desired position is established, the lever 312 can be squeezed into the tensioned (locked) state illustrated in the partial cross-sectional view of FIG. 13A. Again, the lever 312 has been pivoted about lever pivot pin 314, and in the position of FIG. 13A, lever 312 has pulled the tension rod 264 upward and caused it to be placed under tension. The stop end 264S of tension rod 264 pulls the wedge 266 up against tapered end 258T. This pushes rod 258 proximally against the ball connector 90, locking the position of the first arm 254 relative to the ball connector 90 and ultimately the base (not shown in this view). In the position of FIG. 13A, lever 312 is pushing down on wedge 310, thereby creating pressure between the wedge 310 and the tapered end 260T of the second rod 260. This pushes the rod 260 against the ball connector 96, thereby fixing the position of any end effector (not shown in this view) coupled to the ball connector 96 relative to the second arm 256. In the position of FIG. 13A, the first and second arms 254, 256 clamp onto the spacing washer 270, thereby also locking the first arm 254 relative to the second arm 256. A more detailed cross-sectional view of the locked state of this embodiment is shown in FIG. 13B. This one lever 312 can effectively lock the end effector relative to the base with just a single hand squeezing the lever 312. When the lever is squeezed again, with a single hand, three different joints (the ball connector 90, the interface between the first and second arms, and the ball connector 96) are released together, leaving the other hand free to position and end effector. This is a highly efficient improvement over the prior art. It also offers more degrees of freedom compared to the prior art while still only needing a single squeeze to lock or unlock the entire apparatus.

FIG. 14 illustrates a third embodiment of a surgical equipment holder 342. Like the embodiments of FIG. 4 and FIG. 8, the surgical equipment holder 342 has a base 86 configured to receive a removable key 88. A ball connector 90 may be coupled to the base 86 as described previously. The surgical equipment holder 342 has a second ball connector 366 which is coupled to an end effector 345 which is configured to be releasably held onto a quick connect port (not shown in this view) on the end of the ball connector 366. In this embodiment the end effector 345 is configured to hold and position a scope port cannula 222, which holds an endoscope 84. The ball connectors 90 and 366 are coupled to adjustable arms 344. The assembly of the adjustable arms of this embodiment are further detailed in FIGS. 15A-15F.

FIGS. 15A-15F are a series of exploded views which show how the adjustable arms 344 shown in FIG. 15 are put together. As shown in FIG. 15A, a tension rod 354 having a connection end 354C and a stop end 354S is passed with the connection end 354C first through a first wedge 266. The stop end 354S of the tension rod 354 is sized to prevent the tension rod 354 from passing all the way through the wedge 266. In this embodiment, the stop end 354S is rounded or even spherical in nature. The assembled tension rod 354 and wedge 266 may be passed up through a hole on the underside of a receiver 268 in the first arm 254. The connection end 354C of the tension rod 354 will stick up out of the receiver 268. A spacing washer 270 may be placed over the connection end 354C protruding from the receiver 268. In this embodiment, and as previously discussed, the spacing washer 270 may have a convex outward surface 271 which ideally shares an assembled center point which is approximately coincident with the center of the spherical stop end 354S. The opening in the spacing washer 270 is sized to allow the tension rod 354 to pivot and therefore the first arm 254 to pivot relative to the second arm 256 in more than a single plane without changing the relative spacing between parts joined by the tension rod 354. The first rod 355 is slid into an opening 274 in a socket 276 and into the hollow interior of the first arm 254. The socket is on a proximal end 278 of the first arm 254, and the opening 274 is aligned with a longitudinal axis 280 of the first arm 254. The rod 355 has a tapered end 355T which can be pressed against the wedge 266 to hold the wedge 266 in the receiver 268. The rod 355 also has a narrow middle section 355N, which is configured to reduce weight and provide spacing between the inner diameter of the first arm 254 and outer diameter of the rod 355 for improved cleaning and sterilization. The socket stop 350 is threaded onto the socket 276, although alternate means of attachment may be used. The ball connector 90 is placed into the socket 276 against the proximal end 355P of the rod 355, and a retainer 346 is attached over the ball connector 90 to the socket stop 350 in order to hold the ball connector 90 in the socket 276. In this embodiment, retainer 346 holds the ball connector 90 against socket stop 350, so the ball can pivot within socket 276. The socket stop 350 is tightened onto the threaded socket 276 during assembly and setup of the adjustable arms 344 to provide a desired amount of unlocked tension between the ball connector 90, the first rod 355, and the wedge 266. The retainer 346 is secured to the socket stop 350 with several set screws 348 fastened into the threaded holes 351 in the socket stop 350. The adjustability of the socket stop 350 relative to the socket 276 can further provide an adjustable amount of ease of movement between the first arm 254 and the second arm 254 when the adjustable arms 344 are in locked or unlocked position. The retainer 346 has an opening 349 through which the attachment portion 116 may protrude. As with previous embodiments, the attachment portion 116 may be attached to a base (not shown).

As shown in FIG. 15B, a second rod 364 is slid into an opening 286 in a socket 288 and into the hollow interior of the second arm 256. The socket 288 is on a distal end 290 of the second arm 256 and the opening 286 is aligned with a longitudinal axis 292 of the second arm 256. The rod 364 has a tapered end 364T which will be accessible in a receiver 306 of the second arm 256. A quick connect port 392 having a ball connector 366 and attachment portion is provided. The attachment portion 390 is configured to have a gap 390G along the center and a hole 396 though which a pin 394 is inserted and fixed via welding, press fitting, or other methods known to those skilled in the art. The pin 394 spans the gap 390G in the attachment portion 390. The quick connect port 392 is inserted through a second opening 296 in the socket 288. The second opening 296 is larger than the first opening 286, and is large enough to allow the entire ball connector 366 to pass into the socket 288 while the attachment portion 390 passes out of the first opening 286. The first opening 286 is sized to prevent the entire portion of the ball connector 366 from passing through the first opening 286. The distal end of the rod 364D rides against the ball connector 366 and helps to hold it in the socket 288.

A lever alignment guide 356 is also coupled to the second arm 256. Further, a lever catch 358 is coupled to the second arm 256, within a catch shield 360, by fastening to the second arm 256 with screws 362. The catch 358 and catch shield 360 could be fastened to the second arm 256 in other ways, for example, with a pin or other attachment technique known to those skilled in the art. The catch shield 360 covers both sides of the catch 358 in order to reduce the likelihood that gloves, clothing, or skin could become caught in the catch 358 during operation of the surgical equipment holder 342.

As shown in FIG. 15C, the receiver opening 294 (which goes all the way through the receiver 306 of the second arm 256) may be aligned with the tension rod 354. FIG. 15D illustrates the resultant assembly of items from FIG. 15C. A lever block 368 has a wedge 370 and a channel 371 which passes therethrough. This channel 371 allows the wedge 370 to be passed over the tension rod 354 so that the wedge 370 sits against the tapered end 364T (not visible in this view) of the second rod 354. A tension clearance opening 387 in the bottom of the proximal end 352P of the lever 352 allows the connection end 354C to pass into the lever 352.

FIG. 15E is an exploded perspective view of a further sub-assembly of the surgical equipment holder 342 of FIG. 14. A lever latch shield 376 and a latch 374 are coupled to the lever 352 by screws 378, but may be attached by other suitable methods known to those skilled in the art. The lever latch shield 376 and the catch shield work in concert to help prevent gloves, clothing, or skin from becoming caught in the latch 374 and catch 358 mechanism during operation of the surgical equipment holder 342. The latch 374 and catch 358 mechanism of this embodiment functions similarly to the latch 322 and catch 302 described with regard to FIGS. 11A-11D. The lever 352 of this embodiment further includes a cleaning release 380 into which a spring 381 is partially inserted. The spring 381 followed by the release 380 are inserted into a matching slot 383 on a proximal end 352P of the lever 352. The cleaning release 380 is pressed inward to compress the spring 381 so that the proximal end 352P of the lever 352 can be set into the lever block 368 over the tension rod 354. The cleaning release 380 is then released, causing the spring 381 to push a post 385 on the cleaning release 380 into a slot 375 on the lever block. While post 385 is in slot 375, the lever 352 of the assembled device can be moved between unlocked and locked positions and vice versa. To move the lever 352 into a cleaning position, the cleaning release 380 is pushed to further compress the spring 381 and allow post 385 to hop from slot 375 to recess 377, when the arm is opened farther away from the arm 256 than it normally would be in an unlocked position. The operation of the cleaning release 380 will be described further in FIGS. 16A-16C.

The lever 352 may be aligned so that a tension pivot pin 386 may be passed through pass-through hole 372T in the lever block 368 and then through hole 382 in the lever 352, through hole 354H in the tension rod 354, and into a hole mirroring hole 382 on the away facing side of the lever 352. When assembled, pin 386 does not engage the lever block 368, but it does pivotably couple the proximal end 352P of the lever 352 to the tension rod 354. The lever 352 is pivotably coupled to the lever block 368 by a lever pivot pin 388 inserted through hole 372L in the lever block 368, hole 384 in the lever 352, and hole 373L in the lever block 368. This coupling also serves the purpose of coupling the arm subassembly shown in FIG. 15D to the lever 352.

FIG. 15F is a fully assembled view of the adjustable arms 344 with the lever 352 in a locked position.

FIGS. 16A-16C display the lever 352 in several operating positions highlighting the enhanced cleanability of the embodiment of the surgical equipment holder 342 shown in FIG. 14. FIG. 16A shows the lever 352 in the closed or locked position. The mechanism of the locking and unlocking positions and their relative influence on the joint elements of the various equipment holders has been discussed previously, for example in FIGS. 11A-11D, 12A-12C and 13A-13B.

FIG. 16B shows the lever 352 in the open or unlocked position. While the lever 352 is somewhat open relative to the position of the second arm 256, there may be restricted access to the second arm 256 and the second rod 364 within for thorough cleaning after a surgical procedure or operation. The post on the cleaning release 380 is constrained within slot 375 on the lever block 368 during the normal locking and unlocking operations of the surgical equipment holder 342. The cleaning release 380 located on the proximal end 352P of the lever 352 can be moved in direction 379 to compress the spring 381 and allow post 385 on the cleaning release 380 to hop from slot 375 to recess 377 when the lever is lifted farther to a cleaning position shown in FIG. 16C. This provides improved access and enhanced cleaning of the surgical instrument holder 342. This mechanism has been described relative to the assembly steps detailed with regard to FIG. 15E.

FIG. 17 is an exploded view showing the assembly of an instrument adapter 402 for a scope port cannula 222 similar the one described in FIG. 5D.

A lower yoke 404 has a circular post 406 that defines an opening 458. There is a recess (not visible in this view) on the outside of the post 406 sized to accept a spring latch 480. The spring latch 408 has a latch 480L which extends past the outer surface of the post 406 when the spring latch 408 is in its recess. A cannula rotation dial 424 is placed over the post 406. A groove 428 runs around the inner circumference of the cannula rotation dial 424. The latch 480L of the spring latch 480 engages this groove and helps to hold the cannula rotation dial 424 in place. Since the latch 480L can ride in the groove 428 which passes all the way around the inside of the rotation dial 424, the cannula rotation dial 424 may be rotated freely in this position, however axial movement of the dial is resisted by the latch 480L.

An adapter release 414 is aligned to a recess 448 of lower yoke 404 such that pivot point 416 can be held in alignment with hole 412 in lower yoke 404 by screw 410 when instrument adapter 402 is assembled. A screw 410 is passed through a hole 412 in the lower yoke 404, through the pivot point 416 on the adapter release 414, then into a corresponding threaded hole 436 on upper yoke 434. A restrictor pin 462 that rides in slot 418 on the adapter release 414 is placed in a hole 466 on the lower yoke 404, passing through slot 418 of the adapter release 414, and then is held in a corresponding hole 464 on the upper yoke 434 when the instrument adapter 402 is assembled. The adapter release 414 has a spring 422 and a latch 420 configured to releasably hold the instrument adapter 402 onto the attachment portion 390 of a surgical equipment holder 342, as will be described later in more detail.

A cannula latch 450 is aligned in a slot 438 of upper yoke 434 such that pivot point 454 can be pinned in alignment with hole 440 in upper yoke 434 by pin 444. The cannula latch 450 has a spring 456 which pushes the latch 450 into an opening 460 defined by the upper yoke 434. The cannula latch 450 also has a release 452 which may be pressed, causing the latch to pivot about pin 444 and withdraw from the opening 460. When pressure is removed from release 452, the cannula latch 450 pushes back into the opening 460.

An anti-rotation pin 446 is inserted into hole 442 in the upper yoke 434. The anti-rotation pin 446 extends down past the underside of the upper yoke 434. The upper yoke 434 is then coupled to the lower yoke 404 as described above with screw 410. While the inner groove 428 of the cannula rotation dial 424 is pushed towards the lower yoke 404 and not engaged with the latch 480L, the cannula rotation dial 424 may be rotated freely. When it is desired to lock the rotation dial 424, the rotation dial 424 may be moved axially towards the upper yoke 434. In so doing, one of a plurality of pin receivers 430 (not shown in this view, but similar receivers 220 are visible in FIG. 5D) positioned around the rotation dial 424 will engage the anti-rotation pin 446 extending down from the upper yoke 434. At approximately the same time, the latch 480L engages the inner groove 428 on the inside of the cannula rotation dial 424, helping to prevent axial movement of the dial which would then allow the rotation dial 424 to rotate again. As long as the rotation dial 424 is left in this position, the rotation dial 424 will hold. To rotate the rotation dial 424 again, the rotation dial 424 would need to be moved axially towards the lower yoke 404 so that the anti-rotation pin 446 disengages from the pin receiver 430. This operation is further detailed in FIGS. 28A and 28B for another embodiment of a cannula adapter.

FIG. 18A is a perspective view of the assembled instrument adapter 402 of FIG. 17. FIG. 18B is a perspective view of the end of the adjustable arms 344 of FIG. 15F, illustrating instrument adapter 402 in alignment for connection with the attachment portion 390 of the surgical equipment holder 342 of FIG. 14. The instrument adapter 402 is connected to the surgical equipment holder 342 by moving the instrument adapter 402 in a direction 468 along a longitudinal axis 470 towards the adjustable arms 344 and aligning the attachment portion 390 with the adapter channel 432 and inserting the attachment portion 390 into the adapter channel 432 until the pin 394 engages the adapter release latch (not shown in this view, but described previously and also in the following FIG. 19). While this embodiment shows an instrument adapter 402 for a scope port cannula 222, other instrument adapters may be attached to the surgical equipment holder 342 in a similar manner. The components in this embodiment which allow the adapter 402 to be removably coupled to the arms 344 are a mount. In this example, the mount includes an upper yoke 434, a lower yoke 404, a cannula latch 450, a rotation dial 424, an adapter release 414 and a channel 432. It may also include a quick connect port 392 having a ball connector 366 and an attachment portion 390 having a pin 394, a set of adjustable arms 344 including a lever 352, and a base 86 with a removable key 88 if the system is taken as a whole. Other types of mounts are disclosed in this specification, and these embodiments and their equivalents are intended to be covered within the scope of the claims.

FIG. 19 is a cross-sectional top view of the instrument adapter of FIG. 18B, showing the mount of the instrument adapter 402 to the attachment portion 390. When the attachment portion 390, connected to the second ball connector 366, is inserted into the adapter channel 432, the pin 394 engages with a leading edge 420L of the adapter release latch 420. The release latch 420 rides up the pin 394 while pivoting around pivot point 416. As the attachment portion 390 is further inserted into the adapter channel 432, the attachment portion pin 394 passes beyond the leading edge 420L to a notch 420N in the latch 420. The spring 422 maintains pressure on the adapter release 414 such that the latch's notch 420N continues to engage the pin 394, thereby holding the adapter 402 to the attachment portion 390. To remove the attachment portion 390 from the adapter channel 432 and thus remove the instrument adapter 402 from the attachment portion 390, the adapter release 414 is depressed, causing the notch 420N of latch 420 to pivot clear of attachment portion pin 394. In this state, the adapter 402 can be pulled off of the attachment portion 390. After the latch 420 is clear of the attachment portion 390, the adapter release 414 can be released. Spring 422 will pivot the latch 420 again, but restrictor pin 462 will keep the leading edge 420L of latch 420 aligned, where it will advantageously contact the attachment portion pin 394 on the next insertion.

FIG. 20 is an exploded view of an improved embodiment of an instrument adapter 472. A lower yoke 474 has a circular post 476 that defines an opening 482. There is a recess 478 on the outside of either side of the post 476 sized to accept a spring latch 480 in each recess 478. Only one recess is fully visible in this view. Each spring latch 480 has a latch 480L which extends past the outer surface of the post 476 when the spring latch 480 is in its recess 478. A cannula rotation dial 488 is placed over the post 476. The inner surface of the cannula rotation dial 488 has several keyed features 489 and a groove 492 running around the inner circumference of the cannula rotation dial 488. Only a small portion of the groove 492 and the keyed features are visible in FIG. 20. The latch 480L of each spring latch 480 engages this groove 492 and helps to resist unintentional movement of the cannula rotation dial 488. Since either latch 480L can ride in the groove 492 which passes all the way around the inside of the rotation dial 488, the cannula rotation dial 488 may be rotated freely in this position, however axial movement of the rotation dial 488 is resisted by the latches 480L. A cannula latch 500 is aligned in a slot 516 of upper yoke 502 such that pivot point 498 can be pinned in alignment with hole 508 in upper yoke 502 by pin 514. The cannula latch 500 has a spring 496 which pivots the latch 500 into an opening 510 defined by the upper yoke 502. The cannula latch 500 also has a release 494 which may be pressed, causing the latch 500 to pivot about pin 514 and withdraw from the opening 510. When pressure is removed from release 494, the spring 496 pivots the cannula latch 500 back into the opening 510. A cam 520 having a flat face 520F and a keyway 524A is inserted into a recess 517A in the upper yoke 502. A corresponding key 524 on an attachment lever 526 is passed through hole 517 and into engagement with the keyway 524A. The attachment lever 526 can be pivoted to rotate the cam 520 inside the adapter 472 between locked and unlocked positions. Operation of the attachment lever 526 will be discussed later in this specification.

An anti-rotation pin 512 is inserted into hole 506 in the upper yoke 502. The anti-rotation pin 512 extends down past the underside of the upper yoke 502. The upper yoke 502 is then coupled to the lower yoke 474 with a screw 484 passed through a hole 486 in the lower yoke 474 and into a corresponding threaded hole 518 in the upper yoke 502. In other embodiments, the upper yoke 502 may be fastened to the lower yoke 474 using other techniques, such as, but not limited to welding or press fitting. While the inner groove 492 of the cannula rotation dial 488 is pushed towards the lower yoke 474 and therefore the inner groove 492 is not engaged with the latches 480L, the cannula rotation dial 488 may be rotated freely. When it is desired to lock the rotation dial 488, the rotation dial 488 may be moved axially towards the upper yoke 502. In so doing, one of a plurality of pin receivers 490 positioned around the rotation dial 488 will engage the anti-rotation pin 512 extending down from the upper yoke 502. At approximately the same time, the latches 480L engage the inner groove 492 on the inside of the cannula rotation dial 488, helping to prevent axial movement of the dial which would then allow the rotation dial 488 to rotate again. As long as the rotation dial 488 is left in this position, the rotation dial 488 will hold. To rotate the rotation dial 488 again, the rotation dial 488 would need to be moved axially towards the lower yoke 474 so that the anti-rotation pin 512 disengages from the pin receiver 490.

FIG. 21 is a perspective view of the assembled instrument adapter of FIG. 20. When the upper yoke 502 and the lower yoke 474 are coupled together, an adapter channel 528 is formed. An attachment portion of a surgical equipment holder may be configured to fit within the adapter channel 528. One example of a suitable attachment portion 624 is shown in FIG. 30C and the cross-sectional views of FIGS. 22A and 22B.

FIGS. 22A and 22B are partial cross-sectional views of the instrument adapter of FIG. 21 in an unlocked and locked state, respectively, relative to an attachment portion 624 which has been inserted into the adapter channel 528. In FIG. 22A, the attachment lever 526 is in a position that has rotated the cam 520 into a position aligning cam face 520F with channel 528 to allow the attachment portion 624 of a surgical equipment holder to be inserted into the adapter channel 528 of instrument adapter 472. FIG. 22B shows the lever 526 in a position that rotated 533 the cam 520 into a recess 532 on attachment portion 624, thereby causing the adapter 472 to be locked onto the attachment portion 624. In this embodiment, the attachment portion 624 has a recess 532 on opposite sides of the attachment portion 624 so that the adapter 472 may be attached in more than one orientation.

FIG. 23 is a perspective view showing the orientation of a cannula 534 which can be inserted into the instrument adapter 472 of FIG. 21. The instrument adapter 472 is configured to receive the cannula 534 into opening 510. The cannula 534 has a proximal opening 535 in communication with a distal opening 536. The cannula 534 also defines a notch 541 in communication with proximal opening 535 to accommodate a light source attachment for an endoscope, an obturator depth stop, or features from other instrumentation which may be inserted into the cannula. A retainer ring 538 snaps onto a retainer groove 539 of the cannula 534. The retainer ring 538 is rotatable using a retainer ring handle 540 between one position where the notch 541 is accessible from the proximal opening 535 and another position where the notch 541 is not accessible from the proximal opening. The cannula 534 also has one or more keyed teeth 543 on an outer portion of the cannula 534. In use, the distal end 537 of the cannula 534 is inserted into the opening 510 of the instrument adapter 472, along axis 544 through the cannula rotation dial 488 until the one or more keyed teeth 543 engage one or more corresponding key features 489 on the inside of the cannula rotation dial 488. The cannula latch 500 (not visible in this view, but discussed with regard to FIG. 20) engages a groove 542 on the cannula 534, preventing undesired axial movement of the cannula 534 relative to the adapter 472, but allowing the cannula 534 to be rotated as desired by the cannula rotation dial 488 (via the intermeshed keyed teeth 543 and corresponding key features 489) when the cannula rotation dial 488 is not engaging the restrictor pin 512 as will be detailed in regard to FIGS. 28A and 28B.

FIG. 24A is a top elevational view of the cannula 534 inserted into the instrument adapter 472 and cannula This view illustrates several longitudinal protrusions 547 and recesses 548 that define a keyed opening 548A that is intended to keep a viewing scope (not shown in this view) that has been passed into the cannula 534 from coming into contact with the recesses 548. The recesses 548 provide further areas where unwanted fluid may accumulate without contacting or fouling a scope lens when used with an endoscope. In some embodiments, the recesses 548 may include a hydrophilic coating to draw fluid away from a scope inserted into the cannula. The protrusions 547 may be substantially longitudinal protrusions, but they do not necessarily need to extend all the way through the cannula 534.

FIG. 24B is a perspective view showing an obturator 552 which can be inserted into the cannula 534. and instrument adapter of FIG. 23. The distal end 552D of the obturator 552 is configured to be inserted into the cannula opening 535. The obturator 552 also has a depth stop 553 at the proximal end 552P and several keyed features 551 at the distal end 552D. The keyed features 551 are configured to correspond to the protrusions 547 and recesses 548 illustrated in FIG. 24A and align the insertion of the obturator 552 into the adapter combination 546 such that insertion of the obturator 552 along a vertical axis 550 aligns the depth stop 553 with the notch 541 on the cannula 534.

FIG. 25 is a side view of the top of the obturator 552 of FIG. 24B inserted into the cannula 534 and instrument adapter 472 of FIG. 23. The retainer ring 539 has been rotated into a closed position such that when inserted, the depth stop 553 on the obturator 552 comes to rest on the closed cannula retainer ring 539. This limits the obturator 552 to a first insertion depth in the cannula 534. The area near the distal end 552D of the obturator 552 which would not extend from the distal opening 536 of the cannula 534 when the obturator depth stop 553 rests against the ring 539 may be covered with a cleaning material such as an absorbent lace or cover. If the retainer ring 539 is opened, then the obturator depth stop 553 can be inserted into the notch 541 to a deeper insertion depth, enabling the cleaning material (not shown in this view) to extend out of the distal opening 536 of the cannula 534 to help wipe away debris and/or fluids which may interfere with a scope that would later be placed into the cannula 534 after the obturator 552 is removed.

FIG. 26 is a perspective view showing an endoscope 554 having a proximal end 554P and a distal end 554D which is configured to be inserted into cannula opening 535. The endoscope 554 also has a light port 555 near the proximal end 554P configured to deliver light to the endoscope 554. The scope's light port 555 advantageously fits into the notch 541 on the cannula 534 so that the endoscope 554 will rotate with the cannula 534 when the adapter's rotation dial 488 is rotated.

FIG. 27 is perspective view of endoscope 554 inserted and locked into the cannula 534 as held by instrument adapter 472. Several pin receivers 490 are visible on the top of the rotation dial 488. These receivers 490 will be discussed more with regard to FIGS. 28A and 28B, but they may be seen more easily here. This view also demonstrates the assembled endoscope end effector 556 having the distal end 554D of the endoscope protruding out from the distal opening 536 of the cannula 534. The retainer ring 539 is shown in a locked or closed position, which prevents the endoscope from being able to be removed from the cannula 534, as described in regard to FIG. 23.

FIGS. 28A-28B are schematic views detailing the rotational dial 488 function of the instrument adapter 472. The endoscope 554 is inserted in the cannula 534 as discussed above. The cannula rotation dial 488 as shown in FIG. 28A has been moved axially towards 557 the lower yoke 474 of the instrument adapter 472, exposing the anti-rotation pin 512 in the instrument adapter 472. In this position, the cannula rotation dial 488 may be rotated freely. As shown in FIG. 28B, when it is desired to lock the rotation dial 488, and therefore prevent the endoscope 554 from being rotated, the rotation dial 488 may be moved axially towards 558 the upper yoke 502 of the instrument adapter 472. In so doing, one of a plurality of pin receivers 490 (not shown in this view, but visible in FIG. 27) positioned around the rotation dial 488 will engage the anti-rotation pin 512 extending down from the upper yoke 502. At approximately the same time, the latches 480L (not visible in this view) engage the inner groove 492 (also not visible in this view) on the inside of the cannula rotation dial 488, helping to prevent axial movement of the dial 488 so the rotation dial 488 is kept from rotating by the pin 512. To rotate the rotation dial 488 again, the rotation dial 488 would need to be moved axially towards 557 the lower yoke 474 so that the anti-rotation pin 512 disengages from the pin receiver 490.

FIG. 29 schematically illustrates a further embodiment of a surgical equipment holder 570. Like the embodiments of FIG. 4, FIG. 8 and FIG. 14, the surgical equipment holder 570 has a base 574 configured to receive a removeable key 572. A ball connector 586 is coupled to the base 574, forming a base joint 580B between the base 574 and a first arm 598. A second arm 654 is coupled to the first arm 598 and a lever 660 at a middle joint 580M. As in previous embodiments described, the surgical equipment holder 570 has a second ball connector 622 coupled to the end of the second arm 654, which is coupled to an adapter 578 at an end joint 580E. In this embodiment the adapter 578 is configured to hold and position a cannula 534 for receiving an endoscope 554. The ball connectors 586 and 622 are coupled to adjustable arms 576 at the ends. The adjustable arms 576 of this embodiment are pivotable about the base joint 580B, middle joint 580M, and the end joint 580E when the lever 660 is in the unlocked or released position. The lever 660 as shown in FIG. 29 is in a locked position. An additional advantage of this embodiment is that while the adjustable arms 576 are not pivotable about the base joint 580B and the middle joint 580M when the lever 660 is in the locked or closed position, the adapter 578 is tightened yet still pivotable for fine-tune adjustment of the adapter 578 about the end joint 580E. The adjustable arms 576 of this embodiment and their assembly and operation are further detailed in FIGS. 30A-30F AND FIGS. 31A-31B, 32A-32B, and 33A-33B.

FIGS. 30A-30F are a series of exploded perspective views which show how the adjustable arms 576 are put together. As shown in FIG. 30A, a tension rod 608 having a connection end 608C and a stop end 608S is passed with the connection end 608C first through a wedge 606. The stop end 608S of the tension rod 608 is sized to prevent the tension rod 608 from passing all the way through the wedge 606. In this embodiment, the stop end 608S is rounded or even spherical in nature. The assembled tension rod 608 and wedge 606 may be passed up through a hole 604 on a receiver 600 at the distal end 598D of the first arm 598. The connection end 608C of the tension rod 608 will protrude from the receiver 600. A spacing washer 602 is placed over the connection end 608C protruding from the receiver 600. In this embodiment, the spacing washer 602 has a convex outward surface 603 which ideally shares an assembled center point that is approximately coincident with the center of the spherical stop end 608S. The opening in the spacing washer 602 is sized to allow the tension rod 608 to pivot and therefore the first arm 598 to pivot relative to the second arm 654 in more than a single plane without changing the relative spacing between parts joined by the tension rod 608. A first rod 594 is slid into an opening 596 in a socket 610 and into the hollow interior of the first arm 598. The socket 610 is threaded and is on a proximal end 598P of the first arm 598, and the opening 596 is aligned with a longitudinal axis 590 of the first arm 598. The rod 594 has a tapered end 594T which can be pressed against the wedge 606 to hold the wedge 606 in the receiver 600. There is a flange 592 at the proximal end 594P of the first rod. The rod 594 also has a narrower portion 594N which provides weight relief and improved cleaning capability for the overall apparatus. The threaded socket 610 is configured to receive a ring nut 588, a ball connector 586 and a retainer 582. The jam nut 588 is threaded onto the socket 610, which limits the extent to which the retainer 582 can be tightened. The ball connector 586 is placed into the socket 610 against the flange 592 fixed to the proximal end 594P of the rod 594, and the retainer 582 is attached over the ball connector 586 to the socket 610 in order to hold the ball connector 586 in the socket 610. The ring nut 588 and retainer 582 are counter rotated against each other to hold the ball connector 586 against the flange 592, so that the ball can pivot within socket 610 with a desired amount of pressure of the ball connector 586 against the rod 594. The adjustability of the jam nut 588 and the retainer 582 provide an adjustable amount of ease of movement between the first arm 598 and the second arm 654 when the adjustable arms 576 are in the unlocked position. The retainer 582 has an opening 583 through which an attachment portion 584 may protrude. As with previous embodiments, the attachment portion 584 may be attached to a base (not shown in this view).

FIG. 30B shows a second rod 612 and a preassembly step before it is inserted into the second arm 654 (described in regard to FIG. 30C). The second rod 612 has a tapered end 612T which is configured with a hole 612H to receive a limiter pin 646, shown later in FIG. 30C. The second rod 612 is configured on the distal end 612D to receive along a longitudinal axis 620 a stack of disc springs 614, a stack of shims 616, and a rodcap 618 before the final assembly of the second arm 654. The stack of disc springs 614, stack of shims 616, and rodcap 618 are loosely held in place during the subsequent assembly steps shown in FIGS. 30C-30F, but may be fastened to the second rod 612 by other methods, such as, but not limited to staking or welding.

As shown in FIG. 30C, the fully assembled second rod 612 of FIG. 30B is slid into opening 628 located at the distal end 630 of the second arm 654, and into the hollow interior of the second arm 654. The opening 628 is aligned with a longitudinal axis 634 of the second arm 654. The tapered end 612T of the second rod 612 slides far enough into the second arm 654 such that a quick connect port 625 having a ball connector 622 and an attachment portion 624, can be placed into hole 626 in the bottom of the distal end 630 of the second arm 654 and out of opening 628. While hole 626 is large enough to allow the ball connector 622 portion to pass through, opening 628 is small enough to restrict the second ball connector 622 from passing completely through. The distal end 612D of the tapered rod 612 is now moved towards the distal end 630 of the second arm 654 to align a hole 647 on the arm 654 with the hole 612H in the tapered end 612T of the second rod 612. Pin 646 is then inserted into hole 647 and then through to hole 612H in the tapered end 612T of the second rod 612. Hole 647 holds the pin 646 in the arm 654, however, the diameter of hole 612H is larger than the diameter of pin 646, such that movement of the tapered rod 612 relative to longitudinal axis 634 is possible within the constraints of hole 612H. This will be further described in more detail with regard to FIGS. 31A-31B. As shown in FIG. 30C, the distal end 612D of the second rod 612 rides against the ball connector 622 and helps to hold it in the distal end 630. A lever alignment guide 648 is coupled to the second arm using a screw 652 to fasten the lever alignment guide 648 through hole 650 in the second arm 654. A catch 656, coupled to a catch shield 658 is also attached to the second arm 654 using another screw 652 to fasten the catch shield 658 through hole 651. While screws are used in this embodiment, other fastening methods may be used. A lever block 642 having a wedge 640 is placed into a hole 643 in the second arm 654 along axis 645, where the wedge 640 is configured to ride against the tapered end 612T of the second rod 612. The lever block 642 also has a channel 644 configured to receive the connection end 608C of the tension rod 608, which will protrude above the lever block 642 prior to final assembly of the adjustable arms 576, as shown in FIG. 30D.

FIG. 30D illustrates the further subassembly step of how the lever 660 is attached to the adjustable arms 576 of the surgical equipment holder 570 of FIG. 29. A latch 670 is attached to the lever 660 with a screw 672. A ball-spring element 662 is inserted into hole 664 in the lever 660. The lever 660 will be pivotably coupled to the lever block 642 by a lever pivot pin 667 and its mirrored pin on the side facing away. The lever 660 is then placed over the connection end 608C of the tension rod 608 protruding from the channel 644 in the lever block 642. The mirror of lever pivot pin 667 on the opposite side is held in a recess 671 in the lever block 642 and the visible pin 667 will be held in a corresponding recess in a lever block plate 674 (not shown in this view). An opening 665 located on the underside of lever 660 near hole 664 and hole 668 is configured to fit the connection end 608C of the tension rod 608. The tension pivot pin 666 is inserted through hole 668 in lever 660, through a hole 608H in the connection end 608C in the tension rod 608 and held against a back 673 of the lever block plate 642. Once installed, the tension pivot pin 666 allows the tension rod 608 to pivot with respect to the lever 660.

FIG. 30E is a perspective view showing the final assembly step of the lever 660. A lever block plate 674 is attached with screws 676 to hold the lever 660 in place and cover the lever pivot pin 667, the tension pivot pin 666, and the ball-spring element 662. The lever block 642 and the inside of the block plate 674 has a guide slot 642S configured to allow the ends of the ball-spring element 662 to freely travel in guide slot 642S during locking and unlocking of the lever 660. To move the lever 660 further away from the second arm 654 to a cleaning position, a minimal force set by the ball-spring element 662 must be overcome to cause the ball spring element 662 to compress and to hop to a cleaning position recess 669 located on the back plate 673 and on the inside of block plate 674 of the lever block 642. While ball spring element is in cleaning position recess 669, the lever 660 is opened farther away from the second arm 654 than it normally would be in an unlocked position.

FIG. 30F illustrates the resultant arm assembly 576 of items from FIG. 30A-30E with the lever 660 in the locked position. The mechanism of the locking and unlocking positions and their relative influence on the joint elements of the various equipment holders has been discussed previously, for example in FIGS. 11A-11D, 12A-12C and 13A-13B. The embodiment of FIG. 30F works similarly. FIGS. 31A-31B are cross-sectional views of a portion of the middle joint 580M from FIG. 30F comparing the position of the lever 660, the tension rod 608 and the tapered end 612T of the second rod 612 when the locking mechanism between the lever 660 and the second arm 654 is in both the unlocked and locked positions, respectively.

FIG. 31A is a cross-sectional view of the middle joint 580M of adjustable arms 576 when the position of the lever 660 relative to the second arm 654 is in the unlocked or released position. In the state of FIG. 31A, the tension rod 608 is untensioned. The lever 660 pivots about lever pivot pin 667, and in the position of FIG. 31A, tension pivot pin 666 is pushing tension rod 608 downward. This allows wedge 606 to slightly disengage tapered end 594T of rod 594, thereby relaxing the grip of the rod 594 on ball connector 586 (not shown in this view). In this position, lever 660 is not pushing down on wedge 640, so pressure between wedge 640 and tapered end 612T is also reduced, thereby relaxing the grip of the rod 612 on ball connector 622. There is also less compression of the spacing washer 602 between the first and second arms 598, 654, thereby allowing the first arm 598 to be pivoted with respect to the second arm 654. In this embodiment, since the spacing washer 602 is curved, the arms 598, 654 may be pivoted relative to each other in the same plane or in different planes. This provides the ability for an operator to position the arms and an end effector coupled to the ball connector 622 easily in any desired position. In this unlocked position, the second rod 612 moves in a direction 684 such that the limiter pin 646 is against the distal end 612D side of hole 612H in the second rod 612 and reduces the compressive force of the stack of disc springs 614 from the end of rod 612 (not shown in this view, but described further in regard to FIG. 32B).

FIG. 31B is a cross-sectional view of the middle joint 580M of adjustable arms 576 when the position of the lever 660 relative to the second arm 654 is in the locked or closed position. When a desired position for the adapter 578 and adjustable arms 576 is established, the lever 660 can be squeezed into the locked state illustrated in the partial cross-sectional view of FIG. 31B. Again, the lever 660 pivots about lever pivot pin 667 and in the position of FIG.

31B, the tension pivot pin 666 pulls the tension rod 608 upward causing the tension rod 608 to be placed under tension. The stop end 608S of tension rod 608 pulls the wedge 606 up against tapered end 594T. This pushes rod 594 proximally against the ball connector 586, locking the position of the first arm 598 relative to the ball connector 586 and ultimately the base 574 (not shown in this view). In the position of FIG. 31B, lever 660 is pushing down on wedge 640, thereby creating pressure between the wedge 640 and the tapered end 612T of the second rod 612. In this locked position, the second rod 612 is pushed against the ball connector 622 in direction 680, and the limiting pin 646 is against the tapered end 612T side of the rod 612. The second rod 612 is also pushed towards the second ball connector 622 to fix the position of the adapter 578 (not shown in this view) relative to the second arm 654, but movement is not restricted with the same amount of force as in previous embodiments. This restricting function of the limiting pin 646, in combination with the stack of disc springs 614 on the opposite end of the second rod 612 (shown in FIGS. 32A-32B and 33A-33B) results in a reduced amount of pressure on the second arm 654 components relative to the pressure on the first arm 598 components and allows some fine adjustment of the adapter 578 (not shown in FIG. 31B) when the first and second arms 598, 654 are locked relative to one another. This one lever 660 can effectively lock the adapter 578 relative to the base with just a single hand squeezing the lever 660, while still allowing for some fine adjustment of the adapter 578 relative to the second arm. When the lever is squeezed again, with a single hand, three different joints (the base joint 580B, the middle joint 580M interface between the first and second arms, and the end joint 580E) are released together, leaving the other hand free to position and adapter 578. This is a highly efficient improvement over the prior art. It also offers more degrees of freedom compared to the prior art while still only needing a single squeeze to lock or unlock the entire apparatus.

FIGS. 32A-32B illustrate the position of the stack of disc springs 614 when the lever 660 is in the unlocked position. FIG. 32A is a partial cross-sectional side view of adjustable arms 576 showing the lever 660 in the open or unlocked position. In FIG. 32B, an enlarged partial cross-sectional side view of the state of the stack of disc springs 614 is shown for the unlocked position. When the lever 660 is in the unlocked position, the second rod 612 is not pressed towards the end joint 580E, and therefore the rodcap 618 and distal end 612D of the second rod 612 is not pressing the disc springs 614 towards the rodcap 618, which allows the stack of disc springs 614 to freely rest in a relaxed state. This allows a free movement of second ball connector 622, and the adapter 578 attached to surgical equipment holder 570 to be freely movable relative to the second arm 654.

FIGS. 33A-33B illustrate the position of the stack of disc springs 614 when the lever 660 is in the locked position. FIG. 33A is a partial cross-sectional side view of adjustable arms 576 showing the lever 660 in the closed or locked position. In FIG. 33B, an enlarged partial cross-sectional sideview of the state of the stack of disc springs 614 is shown. When the lever 660 is in the locked position, the second rod 612 is pressed towards the end joint 580E, and therefore the rod 612 pushes distally in direction 680 against the disc springs 614. The disc springs 614 press against the rodcap 618, pushing the rodcap 618 against the ball connector 622. In this state, the stack of disc springs 614 are in a compressed state. This compressed state of the disc spring washers restricts movement of the second ball connector 622, but the movement of the second ball connector 622 is not as restricted as in embodiments that do not include a stack of disc springs 614. This provides the advantage of allowing some finely adjustable movement of any adapter 578 attached to the second ball connector 622 relative to the second arm 654 while the surgical equipment holder 570 is in the locked state. The ease of fine adjustment can be determined by the disc springs 614. Stiffer springs will require more force for fine adjustment, while softer springs 614 allow for a fine adjustment with less force. Once moved, the adapter 578 will remain in the position desired by the operator. The stiffness of the individual disc spring washers in the stack of disc springs 614 may be configured to provide the desired amount of force in this locked position and allow limited relative movement between the adapter 578 and the base 574 when the lever 660 on the adjustable arms 576 are in the locked position.

FIG. 34 is a right side view of an embodiment of a base for use with the surgical equipment holders of FIG. 4, FIG. 8, FIG. 14, FIG. 18, and FIG. 29. The base 574 has a base body 704 and a removable key 572. The removable key has gears 712 that interface with a screw drive 714 in the base body 704 which actuate a screw thread within an upper clamp shaft 708S (not shown in this view) to raise and lower an upper clamp jaw 708 relative to a pair of lower clamp jaws 710, which are coupled to the base body 704. A stop pin 706 is attached to the upper clamp jaw 708 such that the stop pin 706 interacts with an interference feature (shown in FIG. 35A) to limit the travel of the screw drive 716 along the base body 704.

FIG. 35A-F show front, right side, left side, rear, top, and bottom views, respectively, of the base of FIG. 34. As illustrated in the top view of FIG. 35A, the base 574 has an upper jaw shaft 708S which is coupled to the upper clamp jaw 708 and mounted onto the screw thread (not shown in this view). The upper clamp jaw 708 and upper jaw shaft 708S are configured to slidably travel towards and away from the lower clamp jaws 710. The gears 712 of the removable key 572, shown in FIG. 34, are inserted into the screw drive 714 (shown in FIG. 35E) to turn the screw thread thereby raising and lowering the upper clamp jaw 708 relative to the lower clamp jaws 710 coupled to the base body 704. The base has an interference feature 718 that limits the travel of the upper jaw 708 thereby limiting the extent the jaws 708, 710 can open. The interference feature also contacts the stop pin 706, limiting the extent to which the jaws 708, 710 can be closed. FIGS. 35B and 35C illustrate an arm mount 722 on both the right and left side of the base body 704, respectively, where a set of adjustable arms 576 are attached. The base 574 is clamped to an accessory rail of a surgical table. t While a screw type clamp is used in this embodiment, other methods of clamping or attaching of a base may be used with the surgical equipment holders described herein.

FIGS. 36A-36B are perspective views of the surgical equipment holder 570 of FIG. 29 coupled to base 574 shown in FIG. 34 and FIGS. 35A-F being attached to a surgical table 728. FIG. 36A illustrates how the base 574 for the surgical equipment holder 570 as described in regard to FIG. 29 is attached to an accessory rail 726 of a surgical table 728, which is covered in a surgical drape 729. The lower clamp jaw 710 is hooked under the accessory rail 726 and pivoted in a direction towards 730 the surgical table 728 until the upper clamp jaw 708 is aligned vertically with the lower clamp jaw 710 and is also in a position to hook onto the accessory rail 726. The embodiment shown in FIG. 36A has adjustable arms 576 as described in regard to FIG. 29, having a first arm 598, a second arm 654, a lever 660 and an attachment portion 624 or adapter 578 (not shown in this view) for the connection and positioning of various adapters and surgical equipment useful in surgical procedures. An advantage of utilizing this base 574 with this surgical equipment holder 570 is that it can be clamped directly over the surgical drape 729 and onto the accessory rail 726 without having to remove or reposition the drape 729. This is an improvement over other methods of instrument holders and similar devices. Once the upper clamp jaw 708 and lower clamp jaws 710 are placed in the desired horizontal location on the accessory rail 726, the removable key 572 is turned in a clockwise direction 742 to engage a screw thread 716 to move the upper clamp jaw 708 closer to the lower clamp jaw 710 such that the base 574 and therefore the entire surgical equipment holder 570 is firmly attached to the accessory rail as shown in FIG. 36B. Once base is clamped, the knob or key 572 can be set aside in a sterile location until needed for removal of the surgical instrument holder 570. While this embodiment of a clamping base is shown in the preceding figures, other methods for clamping or attaching a base 574 to an accessory rail 726 on a surgical table 728.

FIGS. 37A-37B are perspective views of other embodiments of instrument adapters 744, 762 for use with the surgical equipment holder of FIG. 29. FIG. 37A shows an adapter 744 comprised of a body 746 having a channel (not shown in this view) which can be slidably engaged onto a quick connect port 625 (not shown here) and locked with a lever 748 similar to the instrument adapter 472 described with regard to FIG. 21. Further positional adjustment can be achieved using such an adapter 744 by using a knob 750 to tighten an articulating hinge 752 once an upper arm 754 and lower arm 756 are adjusted to a desired position. An upper accessory attachment point 758 is located at the end of the upper arm 754 and a lower accessory attachment point 760 is located at the end of the lower arm 756. This type of adapter may be arranged with alternative arrangements of the upper arm 754 and lower arm 756, for example, as shown in the mirror image 744M as illustrated later in FIG. 38. FIG. 37B is an adapter 762 similar to the adapter 744 shown in FIG. 37A. The adapter 762 has a body 766 with a locking lever 764 at a distal end 766D of the adapter 762 and a single accessory attachment point 768 at a proximal end 766P of the adapter 762.

FIG. 38 is a perspective view of a suture management system 772 and a rib retractor 776 for use with the surgical equipment holder 570 of FIG. 29. A suitable suture management system could be the RAM® Ring from LSI Solutions, Inc. of Victor, N.Y. (lsisolutions.com). Adapter 744M, as shown in mirror image as adapter 744 in FIG. 27A, is configured to be connected to a surgical equipment holder 570. A surgical rib retractor 776 is attached to the upper accessory attachment point 758 of adapter 744. A suitable rib retractor could be the 3D™ Retractor from LSI Solutions, Inc. of Victor, N.Y. (lsisolutions.com). The surgical rib retractor 776 has two adjustable arm units 782 each configured to receive a rib and spread the ribs apart to provide more access to a patient's thoracic cavity during a minimally invasive surgical procedure. An apparatus for suture management 772 is attached by a bolt 774 to the lower accessory attachment point 760 (not visible in this view) of adapter 744. This apparatus for suture management 772 includes three segments 780 configured to hold and manage sutures (not shown here) during surgical procedures. A support 778 is connected to each of the segments 780 and are configured to help support the apparatus for suture management 772 during a minimally invasive surgical procedure. The pivotable articulation of the surgical instrument holders described herein combined with the adapters 744, 762 provide a surgical team with a finely adjustable positioning system for precise location of surgical instrumentation around an incision site during a minimally invasive surgical procedure. While mechanical hinges and bolted mechanical connections are shown in these adapters, other types of hinges, fasteners, or attachment methods may be used.

FIG. 39 is a perspective view of a display mount adapter 784 for use with the surgical equipment holder 570 of FIG. 29. The display mount adapter 784 has an upper yoke 794 and lower yoke 796 fastened together using a screw (not shown here). The display mount adapter 784 can be slidably engaged onto a quick connect port 625 (not shown here) and locked with a lever 786 similar to the instrument adapter 472 described with regard to FIG. 21. The upper yoke 794 and lower yoke 796 define a channel 788 configured to receive a quick connect port 625 connected to a surgical equipment holder 570. A display ball connector 790 having a threaded post (not shown here) is attached to the display mount adapter 784 and tightened using a nut 792, although other methods of fastening such as welding, staking, and others may be used.

FIG. 40A-B are perspective views of a display attached to the display mount adapter of FIG. 39. A display adapter 797 has a pivot nut 800 pre-assembled onto the display ball connector 790. This pivot nut 800 is then fastened onto a threaded member (not shown in this view) located on the back of a mount plate and configured to allow the mount plate 802 and thus the entire display 798 to pivot freely on the display ball connector 790 until the pivot nut 800 is tightened. The mount plate 802 is attached to a display mount 804 utilizing several mount bolts 803. The display mount 804 has a display holder 806 having two adjustable display arms 808 terminated in two display grips 810 configured to reliably hold a display 798. The adjustable display arms 808 are also configured to be movable and lockable in opposition to one another to reliably hold a mounted display 798 such as a tablet, device, or monitor. The mounted display 798 is used for viewing the output from an endoscope or other video capture device during a surgical procedure. The use of this display adapter 797 and display 798 with a surgical equipment holder 570 can provide many degrees of freedom for positioning the display 798 in a convenient and desirable location during a minimally invasive surgical procedure.

FIG. 41 is a perspective view of three surgical equipment holders 570 of FIG. 29 attached to a surgical table 728 with different adapters and equipment attached thereto for use during a minimally invasive surgical procedure on a patient 812. One is configured to hold a cannula 534 and endoscope similar to the one described in regard to FIG. 29. Another is configured to hold an apparatus for suture management 772 and surgical rib retractor 776 as illustrated in FIG. 38. The third is configured to hold a display mount adapter 784 and a display 798 as described in regard to FIGS. 40A and 40B. The three surgical equipment holders 570 are attached to the accessory rail 726 of a surgical table 728, where the base 574 of each surgical equipment holder 570 clamps each respective equipment holder 570 over the surgical drapes 729.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

The invention claimed is:

1. A surgical equipment holder, comprising:
a first arm pivotable relative to a base;
a second arm pivotably coupled to the first arm;
an end effector pivotable relative to the second arm;
a lever movable between a locked position and an unlocked position;
a tension rod in communication with the first arm, the second arm and the lever, the tension rod including a spherical stop end; and
a spacing washer comprised of a convex outward surface, wherein the spacing washer shares an assembled center point which is approximately coincident with a center of the spherical stop end of the tension rod,
the lever being configured such that:
  a) that the first arm does not pivot relative to the base, the second arm does not pivot relative to the first arm when the lever is in the locked position; and
  b) the first arm may be pivoted relative to the base, the second arm may be pivoted relative to the first arm, and the end effector may be pivoted relative to the second arm when the lever is in the unlocked position.

2. The surgical equipment holder of claim 1, wherein the end effector does not pivot relative to the second arm when the lever is in the locked position.

3. The surgical equipment holder of claim 1, wherein the end effector may be pivoted relative to the second arm when the lever is in the locked position.

4. The surgical equipment holder of claim 1 further comprising a spring coupled to the lever.

5. The surgical equipment holder of claim 4 wherein the lever is configured to be in an unlocked position when the lever is squeezed towards the second arm.

6. The surgical equipment holder of claim 4 wherein the lever is configured to be in a locked position when the lever is not squeezed.

7. The surgical equipment holder of claim 1 wherein the spherical stop end of the tension rod is configured to apply pressure onto a wedge in the first arm.

8. The surgical equipment holder of claim 1 further comprising a locking mechanism comprised of a latch coupled to the lever and a catch coupled to the second arm.

9. The surgical equipment holder of claim 8 configured to engage the locking mechanism by moving the lever towards the second arm.

10. The surgical equipment holder of claim 8 configured to disengage the locking mechanism by moving the lever towards the second arm when in the locked position.

11. The surgical equipment holder of claim 8, further comprising a lever block comprising a wedge pivotably coupled to the lever.

12. The surgical equipment holder of claim 1, wherein the first arm and second arm are further comprised of one or more slots configured to provide access for cleaning.

13. The surgical equipment holder of claim 1, wherein the lever is movable to a cleaning position by actuation of a spring element.

14. The surgical equipment holder of claim 1, wherein the first arm further comprises a jam nut.

15. The surgical equipment holder of claim 1, the base further comprising a removable key, an upper jaw, and a lower jaw.

16. The surgical equipment holder of claim 15, wherein the base is clampable to an accessory rail of a surgical table.

17. The surgical equipment holder of claim 1 further comprising an instrument adapter coupled to the end effector.

18. The surgical equipment holder of claim 17, further comprising a rotation dial.

19. The surgical equipment holder of claim 17, further comprising a latching mechanism comprised of a latch and a spring.

20. The surgical equipment holder of claim 17, further comprising a locking mechanism comprised of a lever and a cam.

21. The surgical equipment holder of claim 17 further comprising a scope port cannula coupled to the instrument adapter.

22. A surgical equipment holder, comprising:
a.) a first arm pivotable relative to a base;
b.) a second arm pivotably coupled to the first arm;
c.) an end effector pivotable relative to the second arm; and
d.) a lever movable between a locked position and an unlocked position and configured such that:
  i) that the first arm does not pivot relative to the base, the second arm does not pivot relative to the first arm, and the end effector does not pivot relative to the second arm when the lever is in the locked position; and
  ii) the first arm may be pivoted relative to the base, the second arm may be pivoted relative to the first arm, and the end effector may be pivoted relative to the second arm when the lever is in the unlocked position; and
e.) tension rod having a spherical stop end in communication with the first arm, the second arm and the lever; and
f.) spacing washer having a convex outward surface configured such that the spacing washer shares an assembled center point which is approximately coincident with the center of the spherical stop end of the tension rod; and
g.) a locking mechanism comprised of a latch coupled to the lever and a catch coupled to the second arm, configured such that:
  i.) the locking mechanism is engaged by moving the lever towards the second arm; and
  ii.) the locking mechanism is disengaged by moving the lever towards the second arm when in the locked position.

23. The surgical equipment holder of claim 22 wherein the spherical stop end of the tension rod is configured to apply pressure onto a wedge in the first arm.

24. The surgical equipment holder of claim 1, wherein the lever is movable to a cleaning position by actuation of a spring element.

* * * * *